US008025888B2

(12) United States Patent
Eichmeyer et al.

(10) Patent No.: US 8,025,888 B2
(45) **Date of Patent: *Sep. 27, 2011**

(54) PCV2 IMMUNOGENIC COMPOSITIONS AND METHODS OF PRODUCING SUCH COMPOSITIONS

(75) Inventors: Marc Eichmeyer, Bondurant, IA (US); Greg Nitzel, Mattawan, MI (US); Merrill Schaeffer, St. Joseph, MO (US)

(73) Assignee: Boehringer Ingelheim Vetmedica, Inc., St. Joseph, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 12/137,909

(22) Filed: Jun. 12, 2008

(65) Prior Publication Data

US 2009/0022749 A1 Jan. 22, 2009

Related U.S. Application Data

(60) Division of application No. 11/319,975, filed on Dec. 29, 2005, now Pat. No. 7,700,285, and a continuation-in-part of application No. 11/034,797, filed on Jan. 13, 2005, now Pat. No. 7,833,707.

(60) Provisional application No. 60/640,510, filed on Dec. 30, 2004.

(51) Int. Cl.
*A61K 39/12* (2006.01)

(52) U.S. Cl. ........................................ 424/204.1; 435/5

(58) Field of Classification Search .................. 530/300
See application file for complete search history.

(56) References Cited

U.S. PATENT DOCUMENTS 5,322,774 A 6/1994 Peakman
5,565,205 A 10/1996 Petersen
5,580,557 A 12/1996 Kramer
5,733,555 A 3/1998 Chu
5,885,823 A 3/1999 Knittel
5,925,359 A 7/1999 Van Woensel
5,968,525 A 10/1999 Fitzgerald
6,217,883 B1 4/2001 Allan
6,287,856 B1 9/2001 Poet
6,294,176 B1 9/2001 Cochran
6,368,601 B1 4/2002 Allan
6,391,314 B1 5/2002 Allan
6,497,883 B1 * 12/2002 Bublot et al. ............. 424/204.1
6,517,843 B1 2/2003 Ellis
6,660,272 B2 12/2003 Allan
6,703,023 B1 3/2004 Jestin
6,794,163 B2 9/2004 Liu
6,841,364 B2 1/2005 Yuan
6,846,477 B2 1/2005 Keich
6,943,152 B1 9/2005 Audonnet
6,953,581 B2 10/2005 Allan
7,018,638 B2 3/2006 Chu
7,109,025 B1 * 9/2006 Eloit et al. ................ 435/320.1
7,122,192 B2 10/2006 Allan
7,144,698 B2 12/2006 Wang
7,148,015 B2 12/2006 Jestin
7,169,394 B2 1/2007 Chu
7,172,899 B2 2/2007 Liu
7,179,472 B2 2/2007 Jestin
7,192,594 B2 3/2007 Haines
7,211,379 B2 5/2007 Ellis
7,223,207 B1 5/2007 Basyuk
7,223,407 B2 * 5/2007 Jestin et al. ............... 424/199.1
7,223,594 B2 * 5/2007 Jestin et al. .................. 435/325
7,244,433 B2 7/2007 Jestin
7,258,865 B2 8/2007 Jestin
7,261,898 B2 8/2007 Jestin
7,273,617 B2 9/2007 Yuan
7,276,353 B2 10/2007 Meng
7,279,166 B2 10/2007 Meng
7,297,537 B2 11/2007 Jestin
7,300,785 B2 11/2007 Meerts
7,314,628 B2 1/2008 Jestin et al.
7,323,330 B2 1/2008 Jestin
7,335,361 B2 2/2008 Liao
7,358,075 B2 4/2008 Allibert
7,368,117 B2 5/2008 Fetzer
7,371,395 B2 5/2008 Parisot
7,390,494 B2 6/2008 Jestin
7,405,075 B2 7/2008 Jestin
7,407,803 B2 8/2008 Jestin
(Continued)

FOREIGN PATENT DOCUMENTS

EP 1281760 A1 2/2003

(Continued)

OTHER PUBLICATIONS

Kim et al, The Veterinary Journal, 2003, vol. 166, pp. 251-256.*
Albina et al., An Experimental Model for Post-weaning Multisystemic Wasting Syndrome (PMWS) in Growing Piglets, J. Comp. Path., 2001, vol. 123, 292-303.
Allan et al., Experimental infection of colostrum deprived piglets with porcine circovirus 2 (PCV2) and porcine reproductive and respiratory syndrome virus (PRRSV) potentiates PCV2 replication, Arch. Virol., 2000, 145: 2421-2429.

(Continued)

*Primary Examiner* — Ali R. Salimi
(74) *Attorney, Agent, or Firm* — Michael P. Morris; Julie A. Scott

(57) ABSTRACT

An improved method for recovering the protein expressed by open reading frame 2 from porcine circovirus type 2 is provided. The method generally involves the steps of transfecting recombinant virus containing open reading frame 2 coding sequences into cells contained in growth media, causing the virus to express open reading frame 2, and recovering the expressed protein in the supernate. This recovery should take place beginning approximately 5 days after infection of the cells in order to permit sufficient quantities of recombinant protein to be expressed and secreted from the cell into the growth media. Such methods avoid costly and time-consuming extraction procedures required to separate and recover the recombinant protein from within the cells.

38 Claims, 4 Drawing Sheets

U.S. PATENT DOCUMENTS

| | | |
|---|---|---|
| 7,425,444 B2 | 9/2008 | Jestin |
| 2003/0170270 A1 | 9/2003 | Meng |
| 2004/0062775 A1 | 4/2004 | Jestin |
| 2004/0076635 A1 | 4/2004 | Jestin |
| 2004/0091502 A1 | 5/2004 | Jestin |
| 2004/0132178 A1 | 7/2004 | Haines |
| 2004/0161410 A1 | 8/2004 | Jestin |
| 2004/0253270 A1 | 12/2004 | Meng |
| 2004/0265848 A1 | 12/2004 | Jestin |
| 2005/0008651 A1 | 1/2005 | Jestin |
| 2005/0058653 A1 | 3/2005 | Ellis |
| 2005/0079185 A1 | 4/2005 | Parisot |
| 2005/0084497 A1 | 4/2005 | Jestin |
| 2006/0002952 A1 | 1/2006 | Haines |
| 2006/0029617 A1 | 2/2006 | Charreyre |
| 2006/0115489 A1 | 6/2006 | Birkett |
| 2006/0204522 A1 | 9/2006 | Kroll |
| 2006/0222659 A1 | 10/2006 | Jestin |
| 2006/0233831 A1 | 10/2006 | Parisot |
| 2006/0286123 A1 | 12/2006 | Fetzer |
| 2007/0196879 A1 | 8/2007 | Chabriere et al. |
| 2008/0181910 A1 | 7/2008 | Roof |
| 2008/0233147 A1 | 9/2008 | Jestin |
| 2008/0261887 A1 | 10/2008 | Roof |
| 2008/0279875 A1 | 11/2008 | Roof |
| 2008/0279876 A1 | 11/2008 | Roof |
| 2008/0279889 A1 | 11/2008 | Roof |

FOREIGN PATENT DOCUMENTS

| | | |
|---|---|---|
| EP | 1386617 A1 | 2/2004 |
| WO | 89/06972 A1 | 8/1989 |
| WO | 90/07935 A1 | 7/1990 |
| WO | 91/18627 A1 | 12/1991 |
| WO | 92/03157 A1 | 3/1992 |
| WO | 93/16726 A2 | 9/1993 |
| WO | 95/30437 A1 | 11/1995 |
| WO | 99/18214 A1 | 4/1999 |
| WO | 99/29717 A3 | 6/1999 |
| WO | 99/29871 A3 | 6/1999 |
| WO | 00/47756 | 8/2000 |
| WO | 00/77188 A2 | 12/2000 |
| WO | 01/016330 A3 | 3/2001 |
| WO | 01/17550 A2 | 3/2001 |
| WO | 01/17551 A2 | 3/2001 |
| WO | 01/17556 A1 | 3/2001 |
| WO | 02/49666 A2 | 6/2002 |
| WO | 03/003941 A2 | 1/2003 |
| WO | 2004/058142 A2 | 7/2004 |
| WO | 2004/069184 A2 | 8/2004 |
| WO | 2005/009462 A2 | 2/2005 |
| WO | 2006/072065 A2 | 7/2006 |
| WO | 2006/113372 A2 | 10/2006 |
| WO | 2006/113373 A2 | 10/2006 |
| WO | 2007/028823 A1 | 3/2007 |
| WO | 2007/076520 A2 | 7/2007 |

OTHER PUBLICATIONS

Allan et al., Porcine circoviruses: a review, J. Vet. Diagn. Invest., 2000, 12:3-14.

Allan et al., Reproduction of postweaning multisystemic wasting syndrome in pigs experimentally inoculated with a Swedish porcine circovirus 2 isolate, 2003, 15:553-560.

Bassaganya-Riera et al., Conjugated Linoleic Acid Ameliorates Viral Infectivity in a Pig Model of Virally Induced Immunosuppression, American Society for Nutritional Sciences, 2003, 3204-3214.

Blanchard et al., Protection of swine against post-weaning multisystemic wasting syndrome (PMWS) by porcine circovirus type 2 (PCV2) proteins, Vaccine 21, 2003, 4565-4575.

Boisseson et al., Molecular characterization of Porcine circovirus type 2 isolates from post-weaning multisystemic wasting syndrome-affected and non-affected pigs, J Gen Virol, 2004, 85, 293-304.

Bolin et al., Postweaning multisystemic wasting syndrome induced after experimental inoculation of cesarean-derived, colostrum-deprived piglets with type 2 porcine circovirus, J Vet Diagn Invest, 2001, 13:185-194.

Chae, C., Postweaning multisystemic wasting syndrome: a review of aetiology, diagnosis and pathology, The Veterinary Journal, 2004, 168:41-49.

Cheung et al., Kinetics of porcine circovirus type 2 replication, Arch Virol, 2002, 147:43-58.

Darwich et al., Cytokine profiles of peripheral blood mononuclear cells from pigs with postweaning multisystemic wasting syndrome in response to mitogen, superantigen or recall viral antigens, J Gen Virol, 2003, 84, 3453-3457.

Fenaux et al., A Chimeric Porcine Circovirus (PCV) with the Immunogenic Capsid Gene of the Pathogenic PCV Type 2 (PCV2) Clones into the Genomic Backbone of the Nonpathogenic PCV1 Induces Protective Immunity against PCV2 Infection in Pigs, J Virol, Jun. 2004, vol. 78, No. 12, 6297-6303.

GenBank Accession No. AAC61738, Version AAC61738.1 GI:3661517, Sep. 29, 1998.

Allan et al., Guest Editorial, PCV-2 infection in swine; more than just postweaning multisystemic wasting syndrome, The Veterinary Journal, 2003, 166:222-223.

Inumaru et al., Expression of biologically active recombinant porcine GM-CSF by baculovirus gene expression system, Immunology and Cell Biology, 1998, 76:195-201.

Ju et al., Immunogenicity of a recombinant pseudorabies virus expressing ORF1-ORF2 fusion protein of porcine circovirus type 2, Veterinary Microbiology, 2005, 109:179-190.

Kim et al., Enteritis associated with porcine circovirus 2 in pigs, The Canadian Journal of Veterinary Research, 2004, 68:218-221.

Kim et al., A Comparison of the Lymphocyte Subpopulations of Pigs Experimentally Infected with Porcine Circovirus 2 and/or Parvovirus, The Veterinary Journal, 2003, 165:325-329.

Kim et al., Characterization of the Recombinant Proteins of Porcine Circovirus Type2 Field Isolate Expressed in the Baculovirus System, J Vet Sci, 2002, 3(1), 19-23.

Kyriakis et al., The Effects of Immuno-modulation of the Clinical and Pathological Expression of Postweaning Multisystemic Wasting Syndrome, J Comp Path, 2002, 126:38-46.

Ladekjaer-Mikkelsen et al., Reproduction of postweaning multisystemic wasting syndrome (PMWS) in immunostimulated and non-immunostimulated 3-week-old piglets experimentally infected with porcine circovirus type 2 (PCV2), Veterinary Microbiology, 2002, 89:97-114.

Allan et al., Letters, Immunostimulations, PCV-2 and PMWS, The Veterinary Record, Aug. 5, 2000, 170-171.

Liu et al., Bacterial Expression of an Immunologically Reactive PCV2 ORF2 Fusion Protein, Protein Expression and Purification, 2001, 21:115-120.

Mackinnon, Vaccination Ramification? An Objective Look at How Vaccination Might Affect Post-weaning Multisystemic Wasting Syndrome (PMWS) and Porcine Dermatitis and Nephropathy Syndrome (PDNS), The Pig Journal, 2003, 51:36-63.

Mahe et al., Differential recognition of ORF2 protein from type 1 and type 2 porcine circoviruses and identification of immunorelevant epitopes, J Gen Virol, 2000, 81:1815-1824.

Maranga et al., Virus-Like Particle Production at Low Multiplicities of Infection With the Baculovirus Insect Cell System, Biotechnology and Bioengineering, Aug. 20, 2003, vol. 84, No. 2, 246-253.

McNeilly et al., Evaluation of a porcine circovirus type 2-specific antigen-captive enzyme-linked immunosorbent assay for the diagnosis of postweaning multisystemic wasting syndrome in pigs: comparison with virus isolation, immunohistochemistry, and the polymerase chain reaction, J Vet Diagn Invest, 2002, 14:106-112.

Minion et al., The Genome Sequence of Mycoplasma hyopneumoniae Strain 232, the Agent of Swine Mycoplasmosis, J Bacteriol, Nov. 2004, vol. 186, No. 21, p. 7123-7133.

Morales et al., Serendipitous Discovery and X-Ray Structure of a Human Phosphate Binding Apolipoprotein, Structure, Mar. 2006, 14:601-609.

Nawagitgul et al., Open reading frame 2 of porcine circovirus type 2 encodes a major capsid protein, J Gen Virol, 2000, 81:2281-2287.

Nawagitgul et al., Modified Indirect Porcine Circovirus (PCV) Type 2-Based and Recombinant Capsid Protein (ORF-2)-Based Enzyme-Linked Immunosorbent Assays for Detection of Antibodies to PCV, Clinical and Diagnositc Laboratory Immunology, Jan. 2002, vol. 9, No. 1, p. 33-40.

Okuda, et al., Experimental reproduction of post-weaning multisystemic wasting syndrome in cesarean-derived, colostrum-deprived piglets inoculated with porcine circovirus type 2 (PCV2): investigation of quantitative PCV2 distribution and antibody responses, J Vet Diagn Invest, 2003, 15:107-114.

Olvera et al., Comparison of porcine circovirus type 2 load in serum quantified by a real time PCR in postweaning multisystemic wasting syndrome and porcine dermatitis and nephropathy syndrome naturally affected pigs, Journal of Virological Methods, 2004, 117:75-80.

Opriessnig et al., Porcine Circovirus Type 2 Infection Decreases the Efficacy of a Modified Live Porcine Reproductive and Respiratory Syndrome Virus Vaccine, Clinical and Vaccine Immunology, Aug. 2006, vol. 13, No. 8, p. 923-929.

Quintana et al., Clinical and pathological observations on pigs with postweaning multisystemic wasting syndrome, The Veterinary Record, 2001, 149:357-361.

Rovira et al., Experimental Inoculation of Conventional Pigs with Porcine Reproductive and Respiratory Syndrome Virus and Porcine Circovirus 2, J Virol, Apr. 2002, vol. 76, No. 7, p. 3232-3239.

Rueda et al., Effect of different baculovirus inactivation procedures on the integrity and immunogenicity of porcine parvovirus-like particles, Vaccine, 2001, 19:726-734.

Segales et al., Changes in peripheral blood leukocyte populations in pigs with natural postweaning multisystemic wasting syndrome (PMWS), Veterinary Immunology and Immunopathology, 2001, 81:37-44.

Segales et al., Postweaning multisystemic wasting syndrome (PMWS) in pigs. A review, Veterinary Quarterly, 2002, 24(3):109-124.

Segales et al., Epidemiology of porcine circovirus type 2 infection: what do we know? Pig News and Information, 2003, vol. 24, No. 4, p. 103N-110N.

Sibila et al., Use of a polymerase chain reaction assay and and ELISA to monitor porcine circovirus type 2 infection in pigs from farms with and without postweaning multisystemic wasting syndrome, AJVR, Jan. 2004, vol. 65, No. 1, p. 88-92.

Sorden et al., Development of a polyclonal-antibody-based immunohistochemical method for the detection of type 2 porcine circovirus in formalin-fixed, paraffin-embedded tissue, J Vet Diagn Invest, 1999, 11:528-530.

Vansickle, Circovirus Grips Industry, National Hog Farmer, Jul. 16, 2006.

Vasconcelos et al., Swine and Poultry Pathogens: the Complete Genome Sequences of Two Strains of Mycoplasma hyopneumoniae and a Strain of Mycoplasma synoviae, Journal of Bacteriology, Aug. 2005, vol. 187, No. 16, p. 5568-5577.

Vaccination Guidelines for Swine, VIDO Swine Technical Group—Linking knowledge to practical solutions, Vaccination Guidelines, www.vido.org, Jun. 2004.

Vincent et al., Dendritic Cells Harbor Infectious Porcine Circovirus Type 2 in the Abscence of Apparent Cell Modulation or Replication of the Virus, J Virol, Dec. 2003, vol. 77, No. 24, p. 13288-13300.

Walker, et al., Development and application of a competitive enzyme-linked immunosorbent assay for the detection of serum antibodies to porcine circovirus type 2, J Vet Diagn Invest, 2000, 12:400-405.

Yang, Zong-zhao, A survey on porcine circovirus type 2 infection and phylogenetic analysis of its ORF2 gene in Hangzhou, Zhejiang Province, China, J Zhejiang Univ Sci B. Feb. 2008; 9(2): 148-153.

Does stress-free livestock mean safer food?, http://www.foodnavigator.com/Financial-Industry/Does-stress-free-livestock-mean-safer-food, Jun. 4, 2004.

Liu et al., Characterization of a Previously Unidentified Viral Protein in Porcine Circovirus Type 2-Infected Cells and Its Role in Virus-Induced Apoptosis, J Virol, Jul. 2005, vol. 79, No. 13, p. 8262-8274.

Morris et al., Promoter Influence on Baculovirus-Mediated Gene Expression in Permissive and Nonpermissive Insect Cell Lines, J Virol, Dec. 1992, vol. 66, No. 12, p. 7397-7405.

Morris et al., Characterization of Productive and Non-productve ACMNPV Infection in Selected Insect Cell Lines, Virol 197, 1993, 339-348.

Fan et al., Immunogenicity of Empty Capsids of Porcine Circovius Type 2 Produced in Insect Cells, Veterinary Research Communications, 2007, 31:487-496.

Ponsich, Etude Preliminaire De L'Impact Du Circovac Sur L'infection Par Le PCV2 En Maternite, Nov. 10, 1981.

Kixmoller, et al., Reduction of PMWS-associated clinical signs and co-infections by vaccination against PCV2, Vaccine 26 (2008) 3443-51.

Fachinger, et al., The effect of vaccination against porcine circovirus type 2 in pigs suffering from porcine respiratory disease complex, Vaccine (2008) 26, 1488-99.

Chiou, et al., The Effect of Porcine Circovirus Infection on the Immune Response of Pigs After Vaccination Against Classical Swine Fever and Pseudorabies, Proceedings of the 19th IPVS Congress. Copenhagen, Denmark, 2006, vol. 2.

Charbonneau, Canadian Experiences with Porcine Circovirus Associated Disease. Iowa Pork Congress, 2007.

Allan, et al., PMWS/PCVD: Diagnosis, Disease, and Control: What do we know?, Proceedings of the 19th IPVS Congress. Copenhagen, Denmark, 2006, vol. I, 3-9.

Allan et al., Passive Transfer of Maternal Antibodies to PCV2 Protects Against Development of Post-weaning Multisystemic Wasting Syndrome (PMWS): Experimental Infections and a Field Study, The Pig Journal, 2002, 50, 59-67.

Kamstrup, et al., Immunisation against PCV2 structural protein by DNA vaccination of mice, Vaccine, 2004, 22, 1358-1361.

Kost, et al., Recombinant baculoviruses as mammalian cell gene delivery vectors, Trends in Biology, 2002, 20, 173-180.

Groener, The Biology of Baculoviruses, vol. 1, Biological Properties and Molecular Biology, Chapter 9, Specificity and Safety of Baculoviruses, 1986, 177-202.

* cited by examiner

FIG. 2(a)

```
1. SF+ Master Cell Stock
          ↓
2. SF+ Working Cell Stock
          ↓
Ex-Cell 420 medium → 3. Subculture Psg 20 -58 → Microscopic Examination
          ↓
Ex-Cell 420 medium →
Sterile Filtration → 4. Bioreactor SF+ Culture → Microscopic Examination, Cell count, Cell viability
Ex-Cell 420 medium →
          ↓
5. PCV-2 ORF2 Baculovirus Culture → Microscopic Examination, Cell count, Cell viability
Inoculation with WSV MSV+1 to max MSV+4 →
          ↓
6. Harvest
          ↓
7. Filtration
```

PCV2 IMMUNOGENIC COMPOSITIONS AND METHODS OF PRODUCING SUCH COMPOSITIONS

RELATED APPLICATIONS

This application is a divisional of application Ser. No. 11/319,975, filed Dec. 29, 2005 now U.S. Pat. No. 7,700,285, which claims the benefit of provisional application Ser. No. 60/640,510, filed on Dec. 30, 2004, and application Ser. No. 11/034,797, filed on Jan. 13, 2005 now U.S. Pat. No. 7,833,707, the teachings and contents all of which are hereby incorporated by reference.

SEQUENCE LISTING

This application contains a sequence listing in paper format and in computer readable format, the teachings and content of which are hereby incorporated by reference.

BACKGROUND OF THE INVENTION

1. Field of the Invention

One aspect of the present invention is concerned with the recovery of a protein expressed by open reading frame 2 (ORF2) of porcine circovirus type 2 (PCV2). More particularly, the protein is a recombinant protein expressed by a transfected virus containing recombinant coding sequences for porcine circovirus type 2, open reading frame 2. Still more particularly, the transfected virus is permitted to infect cells in growth media and the protein expressed by open reading frame 2 is recovered in the supernate, rather than from inside the cells. Even more particularly, the method involves the steps of amplifying the open reading frame 2 gene from porcine circovirus type 2, cloning this amplified portion into a first vector, excising the open reading frame 2 portion from this first vector and cloning it into a transfer vector, cotransfecting the transfer vector with a viral vector into cells in growth media, causing the cells to become infected by the viral vector and thereby express open reading frame 2, and recovering the expressed recombinant protein coded for by open reading frame 2 in the supernate.

In another aspect, the present invention is concerned with an immunogenic composition effective for inducing an immune response against PCV2, and methods for producing those immunogenic compositions. More particularly, the present invention is concerned with an immunological composition effective for providing an immune response that protects an animal receiving the composition and reduces, or lessens the severity, of the clinical symptoms associated with PCV2 infection. Still more particularly, the present invention is concerned with a protein-based immunological composition that confers effective protection against infection by PCV2. Even more particularly, the present invention is concerned with an immunological composition comprising ORF2 of PCV2, wherein administration of PCV2-ORF2 results in protection against infection by PCV2. Most particularly, the present invention is concerned with an immunological composition effective for conferring effective immunity to a swine receiving the immunological composition, and wherein the composition comprises the protein expressed by ORF2 of PCV2.

2. Description of the Prior Art

Porcine circovirus type 2 (PCV2) is a small (17-22 nm in diameter), icosahedral, non-enveloped DNA virus, which contains a single-stranded circular genome. PCV2 shares approximately 80% sequence identity with porcine circovirus type 1 (PCV1). However, in contrast with PCV1, which is generally non-virulent, swine infected with PCV2 exhibit a syndrome commonly referred to as Post-weaning Multisystemic Wasting Syndrome (PMWS). PMWS is clinically characterized by wasting, paleness of the skin, unthriftiness, respiratory distress, diarrhea, icterus, and jaundice. In some affected swine, a combination of all symptoms will be apparent while other swine will only have one or two of these symptoms. During necropsy, microscopic and macroscopic lesions also appear on multiple tissues and organs, with lymphoid organs being the most common site for lesions. A strong correlation has been observed between the amount of PCV2 nucleic acid or antigen and the severity of microscopic lymphoid lesions. Mortality rates for swine infected with PCV2 can approach 80%. In addition to PMWS, PCV2 has been associated with several other infections including pseudorabies, porcine reproductive and respiratory syndrome (PRRS), Glasser's disease, streptococcal meningitis, salmonellosis, postweaning colibacillosis, dietetic hepatosis, and suppurative bronchopneumonia.

Open reading frame 2 (ORF2) protein of PCV2, having an approximate molecular weight of 30 kDa when run on SDS-PAGE gel, has been utilized in the past as an antigenic component in vaccines for PCV2. Typical methods of obtaining ORF2 for use in such vaccines generally consist of amplifying the PCV2 DNA coding for ORF2, transfecting a viral vector with the ORF2 DNA, infecting cells with the viral vector containing the ORF2 DNA, permitting the virus to express ORF2 protein within the cell, and extracting the ORF2 protein from the cell via cell lysis. These procedures generally take up to about four days after infection of the cells by the viral vector. However, these procedures have a disadvantage in that the extraction procedures are both costly and time-consuming. Additionally, the amount of ORF2 recovered from the cells is not very high; consequently, a large number of cells need to be infected by a large number of viral vectors in order to obtain sufficient quantities of the recombinant expressed protein for use in vaccines and the like.

Current approaches to PCV2 immunization include DNA-based vaccines, such as those described in U.S. Pat. No. 6,703,023. However, such vaccines have been ineffective at conferring protective immunity against PCV2 infection and the clinical signs associated therewith.

Accordingly, what is needed in the art is a method of obtaining ORF2 protein, which does not require extraction of the ORF2 protein from within infected cells. What is further needed are methods of obtaining recombinant ORF2 protein in quantities sufficient for efficiently preparing vaccine compositions. What is still further needed are methods for obtaining ORF2 protein which do not require the complicated and labor-intensive methods required by the current ORF2 protein extraction protocols. Finally, with respect to compositions, what is needed in the art is an immunogenic composition which does confer protective immunity against PCV2 infection and lessens the severity of or prevents the clinical signs associated therewith.

SUMMARY OF THE INVENTION

The present invention overcomes the problems inherent in the prior art and provides a distinct advance in the state of the art. Specifically, one aspect of the present invention provides improved methods of producing and/or recovering recombinant PCV2 ORF2 protein, i) by permitting infection of susceptible cells in culture with a recombinant viral vector containing PCV2 ORF2 DNA coding sequences, wherein ORF2 protein is expressed by the recombinant viral vector, and ii)

thereafter recovering the ORF2 in the supernate. It has been unexpectedly discovered that ORF2 is released into the supernate in large quantities if the infection and subsequent incubation of the infected cells is allowed to progress past the typical prior PCV 2 ORF2 recovery process, which extracts the PCV2 ORF2 from within cells. It furthermore has been surprisingly found, that PCV ORF2 protein is robust against prototypical degradation outside of the production cells. Both findings together allow a recovery of high amounts of PCV2 ORF2 protein from the supernate of cell cultures infected with recombinant viral vectors containing a PCV2 ORF2 DNA and expressing the PCV2 ORF2 protein. High amounts of PCV2 ORF2 protein means more than about 20 μg/mL supernate, preferably more than about 25 μg/mL, even more preferred more than about 30 μg/mL, even more preferred more than about 40 μg/mL, even more preferred more than about 50 μg/mL, even more preferred more than about 60 μg/mL, even more preferred more than about 80 μg/mL, even more preferred more than about 100 μg/mL, even more preferred than about 150 μg/mL, most preferred than about 190 μg/mL. Those expression rates can also be achieved for example by the methods as described in Examples 1 to 3.

Preferred cell cultures have a cell count between about $0.3$-$2.0\times10^6$ cells/mL, more preferably from about $0.35$-$1.9\times10^6$ cells/mL, still more preferably from about $0.4$-$1.8\times10^6$ cells/mL, even more preferably from about $0.45$-$1.7\times10^6$ cells/mL, and most preferably from about $0.5$-$1.5\times10^6$ cells/mL. Preferred cells are determinable by those of skill in the art. Preferred cells are those susceptible for infection with an appropriate recombinant viral vector, containing a PCV2 ORF2 DNA and expressing the PCV2 ORF2 protein. Preferably the cells are insect cells, and more preferably, they include the insect cells sold under the trademark Sf+ insect cells (Protein Sciences Corporation, Meriden, Conn.).

Appropriate growth media will also be determinable by those of skill in the art with a preferred growth media being serum-free insect cell media such as Excell 420 (JRH Biosciences, Inc., Lenexa, Kans.) and the like. Preferred viral vectors include baculovirus such as BaculoGold (BD Biosciences Pharmingen, San Diego, Calif.), in particular if the production cells are insect cells. Although the baculovirus expression system is preferred, it is understood by those of skill in the art that other expression systems will work for purposes of the present invention, namely the expression of PCV2 ORF2 into the supernatant of a cell culture. Such other expression systems may require the use of a signal sequence in order to cause ORF2 expression into the media. It has been surprisingly discovered that when ORF2 is produced by a baculovirus expression system, it does not require any signal sequence or further modification to cause expression of ORF2 into the media. It is believed that this protein can independently form virus-like particles (Journal of General Virology Vol. 81, pp. 2281-2287 (2000) and be secreted into the culture supernate. The recombinant viral vector containing the PCV2 ORF2 DNA sequences has a preferred multiplicity of infection (MOI) of between about 0.03-1.5, more preferably from about 0.05-1.3, still more preferably from about 0.09-1.1, and most preferably from about 0.1-1.0, when used for the infection of the susceptible cells. Preferably the MOIs mentioned above relates to one mL of cell culture fluid. Preferably, the method described herein comprises the infection of $0.35$-$1.9\times10^6$ cells/mL, still more preferably of about $0.4$-$1.8\times10^6$ cells/mL, even more preferably of about $0.45$-$1.7\times10^6$ cells/mL, and most preferably of about $0.5$-$1.5\times10^6$ cells/mL with a recombinant viral vector containing a PCV2 ORF2 DNA and expressing the PCV2 ORF protein having a MOI (multiplicity of infection) of between about 0.03-1.5, more preferably from about 0.05-1.3, still more preferably from about 0.09-1.1, and most preferably from about 0.1-1.0.

The infected cells are then incubated over a period of up to ten days, more preferably from about two days to about ten days, still more preferably from about four days to about nine days, and most preferably from about five days to about eight days. Preferred incubation conditions include a temperature between about 22-32° C., more preferably from about 24-30° C., still more preferably from about 25-29° C., even more preferably from about 26-28° C., and most preferably about 27° C. Preferably, the Sf+ cells are observed following inoculation for characteristic baculovirus-induced changes. Such observation may include monitoring cell density trends and the decrease in viability during the post-infection period. It was found that peak viral titer is observed 3-5 days after infection and peak ORF2 release from the cells into the supernate is obtained between days 5 and 8, and/or when cell viability decreases to less than 10%.

Thus, one aspect of the present invention provides an improved method of producing and/or recovering recombinant PCV2 ORF2 protein, preferably in amounts described above, by i) permitting infection of a number of susceptible cells (see above) in culture with a recombinant viral vector with a MOI as defined above, ii) expressing PCV2 ORF2 protein by the recombinant viral vector, and iii) thereafter recovering the PCV2 ORF2 in the supernate of cells obtained between days 5 and 8 after infection and/or cell viability decreases to less then 10%. Preferably, the recombinant viral vector is a recombinant baculovirus containing PCV2 ORF2 DNA coding sequences and the cells are Sf+ cells. Additionally, it is preferred that the culture be periodically examined for macroscopic and microscopic evidence of contamination or for atypical changes in cell morphology during the post-infection period. Any culture exhibiting any contamination should be discarded. Preferably, the expressed ORF2 recombinant protein is secreted by the cells into the surrounding growth media that maintains cell viability. The ORF2 is then recovered in the supernate surrounding the cells rather than from the cells themselves.

The recovery process preferably begins with the separation of cell debris from the expressed ORF2 in media via a separation step. Preferred separation steps include filtration, centrifugation at speeds up to about 20,000×g, continuous flow centrifugation, chromatographic separation using ion exchange or gel filtration, and conventional immunoaffinity methods. Those methods are known to persons skilled in the art for example by (Harris and Angel (eds.), Protein purification methods—a practical approach, IRL press Oxford 1995). The most preferred separation methods include centrifugation at speeds up to about 20,000×g and filtration. Preferred filtration methods include dead-end microfiltration and tangential flow (or cross flow) filtration including hollow fiber filtration dead-end micro filtration. Of these, dead-end microfiltration is preferred. Preferred pore sizes for dead-end microfiltration are between about 0.30-1.35 μm, more preferably between about 0.35-1.25 μm, still more preferably between about 0.40-1.10 μm, and most preferably between about 0.45-1.0 μm. It is believed that any conventional filtration membrane will work for purposes of the present invention and polyethersulfone membranes are preferred. Any low weight nucleic acid species are removed during the filtration step.

Thus, one further aspect of the present invention provides an improved method of producing and/or recovering recombinant PCV2 ORF2 protein, preferably in amounts described above, by i) permitting infection of a number of susceptible cells (see above) in culture with a recombinant viral vector with a MOI as defined above, ii) expressing PCV ORF2 protein by the recombinant viral vector, iii) recovering the PCV2 ORF2 in the supernate of cells obtained between days 5 and 8 after infection and/or cell viability decreases to less then 10%, and, iv) separating cell debris from the expressed PCV2 ORF2 via a separation step. Preferably, the recombinant viral vector is a baculovirus containing ORF2 DNA coding sequences and the cells are SF+ cells. Preferred separation steps are those described above. Most preferred is a dead-end microfiltration using a membrane having a pore size between about 0.30-1.35 µm, more preferably between about 0.35-1.25 µm, still more preferably between about 0.40-1.10 µm, and most preferably between about 0.45-1.0 µm.

For recovery of PCV2 ORF2 that will be used in an immunogenic or immunological composition such as a vaccine, the inclusion of an inactivation step is preferred in order to inactivate the viral vector. An "immunogenic or immunological composition" refers to a composition of matter that comprises at least one antigen which elicits an immunological response in the host of a cellular and/or antibody-mediated immune response to the composition or vaccine of interest. Usually, an "immunological response" includes but is not limited to one or more of the following effects: the production or activation of antibodies, B cells, helper T cells, suppressor T cells, and/or cytotoxic T cells and/or yd T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host. Thus, the present invention also relates to method of producing and/or recovering recombinant PCV2 ORF2 protein, preferably in amounts described above, by i) permitting infection of a number of susceptible cells (see above) in culture with a recombinant viral vector with a MOI as defined above, ii) expressing PCV ORF2 protein by the recombinant viral vector, iii) recovering the PCV2 ORF2 in the supernate of cells obtained between days 5 and 8 after infection and/or cell viability decreases to less then 10%, iv) separating cell debris from the expressed PCV2 ORF2 via a separation step, and v) inactivating the recombinant viral vector.

Preferably, this inactivation is done either just before or just after the filtration step, with after the filtration step being the preferred time for inactivation. Any conventional inactivation method can be used for purposes of the present invention. Thus, inactivation can be performed by chemical and/or physical treatments. In preferred forms, the volume of harvest fluids is determined and the temperature is brought to between about 32-42° C., more preferably between about 34-40° C., and most preferably between about 35-39° C. Preferred inactivation methods include the addition cyclized binary ethylenimine (BEI), preferably in a concentration of about 1 to about 20 mM, preferably of about 2 to about 10 mM, still more preferably of about 2 to about 8 mM, still more preferably of about 3 to about 7 mM, most preferably of about 5 mM. For example the inactivation includes the addition of a solution of 2-bromoethyleneamine hydrobromide, preferably of about 0.4M, which has been cyclized to 0.2M binary ethylenimine (BEI) in 0.3N NaOH, to the fluids to give a final concentration of about 5 mM BEI. Preferably, the fluids are then stirred continuously for 72-96 hours and the inactivated harvest fluids can be stored frozen at −40° C. or below or between about 1-7° C. After inactivation is completed a sodium thiosulfate solution, preferably at 1.0M is added to neutralize any residual BEI. Preferably, the sodium thiosulfate is added in equivalent amount as compared to the BEI added prior to for inactivation. For example, in the event BEI is added to a final concentration of 5 mM, a 1.0M sodium thiosulfate solution is added to give a final minimum concentration of 5 mM to neutralize any residual BEI.

Thus, one further aspect of the present invention relates to a method of producing recombinant PCV2 ORF2 protein, preferably in amounts described above, by i) permitting infection of a number of susceptible cells (see above) in culture with a recombinant viral vector with a MOI as defined above, ii) expressing PCV ORF2 protein by the recombinant viral vector, iii) recovering the PCV2 ORF2 in the supernate of cells obtained between days 5 and 8 after infection and/or cell viability decreases to less then 10%, iv) separating cell debris from the expressed PCV2 ORF2 via a separation step, and v) inactivating the recombinant viral vector. Preferably, the recombinant viral vector is a baculovirus containing ORF2 DNA coding sequences and the cells are SF+ cells. Preferred separation steps are those described above, most preferred is the filtration step. Preferred inactivation steps are those described above. Preferably, inactivation is performed between about 35-39° C. and in the presence of 2 to 8 mM BEI, still more preferred in the presence of about 5 mM BEI. It has been surprisingly found, that higher concentrations of BEI negatively affect the PCV2 ORF2 protein.

According to one further aspect of the present invention, the method described above also includes an neutralization step after step v). This step vi) comprises adding of an equivalent amount of an agent that neutralizes the inactivation agent within the solution. Preferably, if the inactivation agent is BEI, addition of sodium thiosulfate to an equivalent amount is preferred. Thus, according to a further aspect, step vi) comprises adding of a sodium thiosulfate solution to a final concentration of about 1 to about 20 mM, preferably of about 2 to about 10 mM, still more preferably of about 2 to about 8 mM, still more preferably of about 3 to about 7 mM most preferably of about 5 mM, when the inactivation agent is BEI.

In preferred forms and especially in forms that will use the recombinant PCV2 ORF2 protein in an immunogenic composition such as a vaccine, each lot of harvested ORF2 will be tested for inactivation by passage in the anchorage dependent, baculovirus susceptible Sf+ cells. In a preferred form of this testing, 150 cm² of appropriate cell culture monolayer is inoculated with 1.0 mL of inactivated PCV2 fluids and maintained at 25-29° C. for 14 days with at least two passages. At the end of the maintenance period, the cell monolayers are examined for cytopathogenic effect (CPE) typical of PCV2 ORF2 baculovirus. Preferably, positive virus controls are also used. Such controls can consist of one culture of Sf+ cells inoculated with a non-inactivated reference PCV2 ORF2 baculovirus and one flask of Sf+ cells that remain uninoculated. After incubation and passage, the absence of virus-infected cells in the BEI treated viral fluids would constitute a satisfactory inactivation test. The control cells inoculated with the reference virus should exhibit CPE typical of PCV2 ORF2 baculovirus and the uninoculated flask should not exhibit any evidence of PCV2 ORF2 baculovirus CPE. Alternatively, at the end of the maintenance period, the supernatant samples could be collected and inoculated onto a Sf+ 96 well plate, which has been loaded with Sf+ cells, and then maintained at 25-29° C. for 5-6 days. The plate is then fixed and stained with anti-PCV2 ORF2 antibody conjugated to FITC. The absence of CPE and ORF2 expression, as detected by IFA micoscopy, in the BEI treated viral fluids constitutes a satisfactory inactivation test. The control cells inoculated with the reference virus should exhibit CPE and IFA activity and the uninoculated flask should not exhibit any evidence of PCV2 ORF2 baculovirus CPE and contain no IFA activity.

Thus a further aspect of the present invention relates to an inactivation test for determining the effectiveness of the inactivation of the recombination viral vector, comprises the steps: i) contacting at least a portion of the culture fluid containing the recombinant viral vector with an inactivating agent, preferably as described above, ii) adding a neutralization agent to neutralize the inactivation agent, preferably as described above, and iii) determining the residual infectivity by the assays as described above.

After inactivation, the relative amount of recombinant PCV2 ORF2 protein in a sample can be determined in a number of ways. Preferred methods of quantitation include SDS-PAGE densitometry, ELISA, and animal vaccination studies that correlate known quantities of vaccine with clinical outcomes (serology, etc.). When SDS-PAGE is utilized for quantitation, the sample material containing an unknown amount of recombinant PCV2 ORF2 protein is run on a gel, together with samples that contain different known amounts of recombinant PCV2 ORF2 protein. A standard curve can then be produced based on the known samples and the amount of recombinant PCV2 ORF2 in the unknown sample can be determined by comparison with this standard curve. Because ELISAs are generally recognized as the industry standard for antigen quantitation, they are preferred for quantitation.

Thus, according to a further aspect, the present invention also relates to an ELISA for the quantification of recombinant PCV2 ORF2 protein. A preferred ELISA as provided herewith will generally begin with diluting the capture antibody 1:6000 or an appropriate working dilution in coating buffer. A preferred capture antibody is Swine anti-PCV2 PAb Prot. G purified, and a preferred coating buffer is 0.05M Carbonate buffer, which can be made by combining 2.93 g $NaHCO_3$ (Sigma Cat. No. S-6014, or equivalent) and 1.59 g $NaCO_3$ (Sigma Cat. No. S-6139, or equivalent). The mixture is combined with distilled water, or equivalent, to make one liter at a pH of 9.6±0.1. Next, the capture antibody is diluted 1:6000, or any other appropriate working dilution, in coating buffer. For example, for four plates, one would need 42 mLs of coating buffer and seven μL of capture antibody. Using a reverse pipetting method, 100 μL of diluted capture antibody is added to all of the wells. In order to obtain an even coating, the sides of each plate should be gently tapped. The plates are then sealed with plate sealers, prior to stacking the plates and capping the stack with an empty 96-well plate. The plates are incubated overnight (14-24 hours) at 35-39° C. Each plate is then washed three times with wash buffer using the ultra wash plus micro titer plate washer set at 250 μL/wash with three washes and no soak time. After the last wash, the plates should be tapped onto a paper towel. Again, using the reverse pipetting technique, 250 μL of blocking solution should be added to all of the wells. The test plates should be sealed and incubated for approximately one hour (±five minutes) at 35-37° C. Preferably, the plates will not be stacked after this step. During the blocking step, all test samples should be pulled out and thawed at room temperature. Next, four separate dilution plates should be prepared by adding 200 μL of diluent solution to all of the remaining wells except for row A and row H, columns 1-3. Next, six test tubes should be labeled as follows, low titer, medium titer, high titer, inactivated/filtered (1:240), inactivated/filtered (1:480), and internal control. In the designated tubes, an appropriate dilution should be prepared for the following test samples. The thawed test samples should be vortexed prior to use. For four plates, the following dilutions will be made: A) the low titer will not be pre-diluted: 3.0 mLs of low titer; B) negative control at a 1:30 dilution (SF+ cells): 3.77 mLs of diluent+130 μL of the negative control; C) medium titer at a 1:30 dilution (8 μg/mL): 3.77 mLs of diluent+130 μL of the medium titer; D) high titer at a 1:90 dilution (16 μg/mL): 2.967 mLs of diluent+33 μL of high titer; E) inactivated/filtered at a 1:240 dilution: 2.39 mLs of diluent+10 μL of inactivated/filtered sample; F) inactivated/filtered at a 1:480 dilution: 1.0 mL of diluent+1.0 mL of inact/filtered (1:240) prepared sample from E above; G) internal control at 1:30 dilution: 3.77 mLs of diluent+130 μL of the internal control. Next, add 300 μL of the prepared samples to corresponding empty wells in the dilution plates for plates 1 through 4. The multichannel pipettor is then set to 100 μL, and the contents in Row A are mixed by pipetting up and down for at least 5 times and then 100 μL is transferred to Row B using the reverse pipetting technique. The tips should be changed and this same procedure is followed down the plate to Row G. Samples in these dilution plates are now ready for transfer to the test plates once the test plates have been washed 3 times with wash buffer using the ultrawash plus microtiter plate washer (settings at 250 μL/wash, 3 washes, no soak time). After the last wash, the plates should be tapped onto a paper towel. Next, the contents of the dilution plate are transferred to the test plate using a simple transfer procedure. More specifically, starting at row H, 100 μL/well is transferred from the dilution plate(s) to corresponding wells of the test plate(s) using reverse pipetting technique. After each transfer, the pipette tips should be changed. From Row G, 100 μL/well in the dilution plate(s) is transferred to corresponding wells of the test plate(s) using reverse pipetting technique. The same set of pipette tips can be used for the remaining transfer. To ensure a homogenous solution for the transfer, the solution should be pipetted up and down at least 3 times prior to transfer. Next, the test plate(s) are sealed and incubated for 1.0 hour ±5 minutes at 37° C.±2.0° C. Again, it is preferable not to stack the plates. The plates are then washed 3 times with wash buffer using the ultrawash plus microtiter plate washer (settings at 250 μL/wash, 3 washes, and no soak time). After the last wash, the plates are tapped onto a paper towel. Using reverse pipetting technique, 100 μL of detection antibody diluted 1:300, or appropriate working dilution, in diluent solution is added to all of the wells of the test plate(s). For example, for four plates, one will need 42 mLs of diluent solution with 140 μL of capture antibody. The test plate(s) are then sealed and incubated for 1.0 hour ±5 minutes at 37° C.±2.0° C. Again, the plates are washed 3 times with wash buffer using the ultrawash plus microtiter plate washer (settings at 250 μL/wash, 3 washes, and no soak time). After the last wash, the plates are tapped onto a paper towel. Next, the conjugate diluent is prepared by adding 1% normal rabbit serum to the diluent. For example, for four plates, 420 μL of normal rabbit serum is added to 42 mL of diluent. The conjugate antibody is diluted to 1:10,000, or any other appropriate working dilution, in a freshly prepared conjugate diluent solution to all wells of the test plate(s). Using a reverse pipetting technique, 100 μL of this diluted conjugate antibody is added to all the wells. The test plate(s) are then sealed and incubated for 45±5 minutes at 37° C.±2.0° C. Preferably, the plates are not stacked. The plates are then washed 3 times with wash buffer using the ultrawash plus microtiter plate washer (settings at 250 μL/wash, 3 washes, and no soak time). After the last wash, the plates are tapped onto a paper towel. Next, equal volumes of TMB Peroxidase Substrate (Reagent A) with Peroxidase Solution B (Reagent B) are mixed immediately prior to use. The amount mixed will vary depending upon the quantity of plates but each plate will require 10 mL/plate+2 mLs. Therefore, for 4 plates, it will be 21 mL of Reagent A+21 mL of Reagent B. Using a reverse pipetting technique, 100 μL of substrate is added to all wells of the test plate(s). The plates are then incubated at room temperature for 15 minutes ±15 seconds. The reaction is stopped by the addition of 100 μL of 1N HCl solution to all wells using a reverse pipetting technique. The ELISA plate reader is then turned on and allowed to proceed through its diagnostics and testing phases in a conventional manner.

A further aspect of the invention relates to a method for constructing a recombinant viral vector containing PCV2 ORF2 DNA and expressing PCV2 ORF2 protein in high amounts, when infected into susceptible cells. It has been surprisingly found that the recombinant viral vector as provided herewith expresses high amounts, as defined above, of PCV2 ORF2 after infecting susceptible cells. Therefore, the present invention also relates to an improved method for producing and/or recovering of PCV2 ORF2 protein, preferably comprises the step: constructing a recombinant viral vector containing PCV2 ORF2 DNA and expressing PCV2 ORF2 protein. Preferably, the viral vector is a recombinant baculorvirus. Details of the method for constructing recombinant viral vectors containing PCV2 ORF2 DNA and expressing PCV2 ORF2 protein, as provided herewith, are described to the following: In preferred forms the recombinant viral vector containing PCV2 ORF 2 DNA and expressing PCV2 ORF2 protein used to infect the cells is generated by transfecting a transfer vector that has had an ORF2 gene cloned therein into a viral vector. Preferably, only the portion of the transfer vector is transfected into the viral vector, that contains the ORF2 DNA. The term "transfected into a viral vector" means, and is used as a synonym for "introducing" or "cloning" a heterologous DNA into a viral vector, such as for example into a baculovirus vector. The viral vector is preferably but not necessarily a baculovirus.

Thus, according to a further aspect of the present invention, the recombinant viral vector is generated by recombination between a transfer vector containing the heterologous PCV2 ORF2 DNA and a viral vector, preferably a baculorvirus, even more preferably a linearized replication-deficient baculovirus (such as Baculo Gold DNA). A "transfer vector" means a DNA molecule, that includes at least one origin of replication, the heterologous gene, in the present case PCV2 ORF2, and DNA sequences which allows the cloning of said heterologous gene into the viral vector. Preferably the sequences which allow cloning of the heterologous gene into the viral vector are flanking the heterologous gene. Even more preferably those flanking sequences are at least homologous in parts with sequences of the viral vector. The sequence homology then allows recombination of both molecules, the viral vector and the transfer vector to generate a recombinant viral vector containing the heterologous gene. One preferred transfer vector is the pVL1392 vector (BD Biosciences Pharmingen), which is designed for co-transfection with the BaculoGold DNA into the preferred Sf+ cell line. Preferably, said transfer vector comprises a PCV2 ORF2 DNA. The construct co-transfected is approximately 10,387 base pairs in length.

In more preferred forms, the methods of the present invention will begin with the isolation of PCV2 ORF2 DNA. Generally, this can be from a known or unknown strain as the ORF2 DNA appears to be highly conserved with at least about 95% sequence identity between different isolates. Any PCV2 ORF2 gene known in the art can be used for purposes of the present invention as each would be expressed into the supernate. The PCV ORF2 DNA is preferably amplified using PCR methods, even more preferred together with the introduction of a 5' flanking Kozak's consensus sequence (CCGCCAUG) (SEQ ID NO 1) and/or a 3' flanking EcoR1 site (GAATTC) (SEQ ID NO 2). Such introduction of a 5' Kozak's consensus preferably removes the naturally occurring start codon AUG of PCV2 ORF2. The 3' EcoR1 site is preferably introduced downstream of the stop codon of the PCV2 ORF2. More preferably it is introduced downstream of a poly A transcription termination sequence, that itself is located downstream of the PCV2 ORF2 stop codon. It has been found, that the use of a Kozak consensus sequence, in particular as described above, increases the expression level of the subsequent PCV2 ORF2 protein. The amplified PCV2 ORF2 DNA, with these additional sequences, is cloned into a vector. A preferred vector for this initial cloning step is the pGEM-T-Easy Vector (Promega, Madison, Wis.). The PCV2 ORF2 DNA including some pGEM vector sequences (SEQ ID NO: 7) is preferably excised from the vector at the Not1 restriction site. The resulting DNA is then cloned into the transfer vector.

Thus, in one aspect of the present invention, a method for constructing a recombinant viral vector containing PCV2 ORF2 DNA is provided. This method comprises the steps: i) cloning a recombinant PCV2 ORF2 into a transfer vector; and ii) transfecting the portion of the transfer vector containing the recombinant PCV2 ORF2 into a viral vector, to generate the recombinant viral vector. Preferably, the transfer vector is that described above or is constructed as described above or as exemplarily shown in FIG. 1. Thus according to a further aspect, the transfer vector, used for the construction of the recombinant viral vector as described herein, contains the sequence of SEQ ID NO: 7.

According to a further aspect, this method further comprises prior to step i) the following step: amplifying the PCV2 ORF2 DNA in vitro, wherein the flanking sequences of the PCV2 ORF2 DNA are modified as described above. In vitro methods for amplifying the PCV2 ORF2 DNA and modifying the flanking sequences, cloning in vitro amplified PCV2 ORF2 DNA into a transfer vector and suitable transfer vectors are described above, exemplarily shown in FIG. 1, or known to a person skilled in the art. Thus according to a further aspect, the present invention relates to a method for constructing a recombinant viral vector containing PCV2 ORF2 DNA and expressing PCV2 ORF2 protein comprises the steps of: i) amplifying PCV2 ORF2 DNA in vitro, wherein the flanking sequences of said PCV2 ORF2 DNA are modified, ii) cloning the amplified PCV2 ORF2 DNA into a transfer vector; and iii) transfecting the transfer vector or a portion thereof containing the recombinant PCV2 ORF2 DNA into a viral vector to generate the recombinant viral vector. Preferably, the modification of the flanking sequences of the PCV2 ORF2 DNA is performed as described above, e.g. by introducing a 5' Kozak sequence and/or a EcoR 1 site, preferably as described above.

According to a further aspect, a method of producing and/or recovering recombinant protein expressed by open reading frame 2 of PCV2 is provided. The method generally comprises the steps of: i) cloning a recombinant PCV2 ORF2 into a transfer vector; ii) transfecting the portion of the transfer vector containing the recombinant PCV2 ORF2 into a virus; iii) infecting cells in media with the transfected virus; iv) causing the transfected virus to express the recombinant protein from PCV2 ORF2; v) separating cells from the supernate; and vi) recovering the expressed PCV2 ORF2 protein from the supernate.

Methods of how to clone a recombinant PCV2 ORF2 DNA into a transfer vector are described above. Preferably, the transfer vector contains the sequence of SEQ ID NO:3, SEQ ID NO:4, SEQ ID NO:7. However, the transfer vector can contain any PCV2 ORF2 DNA, unmodified or modified, as long as the PCV2 ORF2 DNA, when transfected into a recombinant viral vector, is expressed in cell culture. Preferably, the recombinant viral vector comprises the sequence of SEQ ID NO:8. Moreover, methods of how to infect cells, preferably how to infect insect cells with a defined number of recombinant baculovirus containing PCV2 ORF2 DNA and expressing PCV2 ORF2 protein are described above in detail. Moreover, steps of separating cells from the supernate as well as steps for recovering the expressed PCV2 ORF2 protein are also described above in detail. Any of these specific process steps, as described herein, are part of the method of producing and/or recovering recombinant protein expressed by open reading frame 2 of PCV2 as described above. Preferably, the cells are SF+ cells. Still more preferably, cell cultures have a cell count between about $0.3$-$2.0 \times 10^6$ cells/mL, more preferably from about $0.35$-$1.9 \times 10^6$ cells/mL, still more preferably from about $0.4$-$1.8 \times 10^6$ cells/mL, even more preferably from about $0.45$-$1.7 \times 10^6$ cells/mL, and most preferably from about $0.5$-$1.5 \times 10^6$ cells/mL. Preferably, the recombinant viral vector containing the PCV2 ORF2 DNA has a preferred multiplicity of infection (MOI) of between about 0.03-1.5, more preferably from about 0.05-1.3, still more preferably from about 0.09-1.1, still more preferably from about 0.1-1.0, and most preferably to about 0.5, when used for the infection of the susceptible cells. Preferably, recovering of the PCV2 ORF2 protein in the supernate of cells obtained between days 5 and 8 after infection and/or cell viability decreases to less then 10%. Preferably, for producing PCV2 ORF2 protein, cells are cultivated at 25 to 29° C. Preferably, the separation step is a centrifugation or a filtration step.

Optionally, this method can include the step of amplifying the PCV2 ORF2 DNA from a strain of PCV2 prior to cloning the PCV2 ORF2 DNA into the transfer vector. In preferred forms, a 5' Kozak's sequence, a 3' EcoR1 site, and combinations thereof can also be added to the amplified sequence, preferably prior to or during amplification. A preferred 5' Kozak's sequence comprises SEQ ID NO: 1. A preferred 3' EcoR1 site comprises SEQ ID NO: 2. Preferred PCV2 ORF2 DNA comprises the nucleotide sequence Genbank Accession No. AF086834 (SEQ ID NO: 3) and SEQ ID NO: 4. Preferred recombinant PCV2 ORF2 protein comprises the amino acid sequence of SEQ ID NO: 5, which is the protein encoded by SEQ ID NO: 3 (Genbank Accession No. AF086834) and SEQ ID No: 6, which is the protein encoded by SEQ ID NO: 4. A preferred media comprises serum-free insect cell media, still more preferably Excell 420 media. When the optional amplification step is performed, it is preferable to first clone the amplified open reading frame 2 into a first vector, excise the open reading frame 2 from the first vector, and use the excised open reading frame for cloning into the transfer vector. A preferred cell line for cotransfection is the SF+ cell line. A preferred virus for cotransfection is baculovirus. In preferred forms of this method, the transfected portion of the transfer vector comprises SEQ ID NO: 8. Finally, for this method, it is preferred to recover the PCV2 open reading frame 2 (ORF2) protein in the cell culture supernate at least 5 days after infecting the cells with the virus.

Thus, a further aspect of the invention relates to a method for producing and/or recovering the PCV2 open reading frame 2, comprises the steps: i) amplifying the PCV2 ORF2 DNA in vitro, preferably by adding a 5' Kozak sequence and/or by adding a 3' EcoR1 restriction site, ii) cloning the amplified PCV2 ORF2 into a transfer vector; iii) transfecting the portion of the transfer vector containing the recombinant PCV2 ORF2 into a virus; iv) infecting cells in media with the transfected virus; v) causing the transfected virus to express the recombinant protein from PCV2 ORF2; vi) separating cells from the supernate; and vii) recovering the expressed PCV2 ORF2 protein from the supernate.

A further aspect of the present invention relates to a method for preparing a composition comprising PCV2 ORF2 protein, and inactivated viral vector. This method comprises the steps: i) cloning the amplified PCV2 ORF2 into a transfer vector; ii) transfecting the portion of the transfer vector containing the recombinant PCV2 ORF2 into a virus; iii) infecting cells in media with the transfected viral vector; iv) causing the transfected viral vector to express the recombinant protein from PCV2 ORF2; v) separating cells from the supernate; iv) recovering the expressed PCV2 ORF2 protein from the supernate; and vii) inactivating the recombinant viral vector. Preferably, the recombinant viral vector is a baculovirus containing ORF2 DNA coding sequences and the cells are SF+ cells. Preferred separation steps are those described above, most preferred is the filtration step. Preferred inactivation steps are those described above. Preferably, inactivation is performed between about 35-39° C. and in the presence of 2 to 8 mM BEI, still more preferred in the presence of about 5 mM BEI. It has been surprisingly found, that higher concentrations of BEI negatively affect the PCV2 ORF2 protein, and lower concentrations are not effective to inactivate the viral vector within 24 to 72 hours of inactivation. Preferably, inactivation is performed for at least 24 hours, even more preferred for 24 to 72 hours.

According to a further aspect, the method for preparing a composition comprising PCV2 ORF2 protein, and inactivated viral vector, as described above, also includes an neutralization step after step vii). This step viii) comprises adding of an equivalent amount of an agent that neutralizes the inactivation agent within the solution. Preferably, if the inactivation agent is BEI, addition of sodium thiosulfate to an equivalent amount is preferred. Thus, according to a further aspect, step viii) comprises adding of a sodium thiosulfate solution to a final concentration of about 1 to about 20 mM, preferably of about 2 to about 10 mM, still more preferably of about 2 to about 8 mM, still more preferably of about 3 to about 7 mM, most preferably of about 5 mM, when the inactivation agent is BEI.

According to a further aspect, the method for preparing a composition comprising PCV2 ORF2 protein, and inactivated viral vector, as described above, comprises prior to step i) the following step: amplifying the PCV2 ORF2 DNA in vitro, wherein the flanking sequences of the PCV2 ORF2 DNA are modified as described above. In vitro methods for amplifying the PCV2 ORF2 DNA and modifying the flanking sequences, cloning in vitro amplified PCV2 ORF2 DNA into a transfer vector and suitable transfer vectors are described above, exemplarily shown in FIG. 1, or known to a person skilled in the art. Thus according to a further aspect, this method comprises the steps: i) amplifying PCV2 ORF2 DNA in vitro, wherein the flanking sequences of said PCV2 ORF2 DNA are modified, ii) cloning the amplified PCV2 ORF2 DNA into a transfer vector; and iii) transfecting the transfer vector or a portion thereof containing the recombinant PCV2 ORF2 DNA into a viral vector to generate the recombinant viral vector, iv) infecting cells in media with the transfected virus; v) causing the transfected virus to express the recombinant protein from PCV2 ORF2; vi) separating cells from the supernate; vii) recovering the expressed PCV2 ORF2 protein from the supernate; viii) inactivating the recombinant viral vector, preferably, in the presence of about 1 to about 20 mM BEI, most preferred in the presence of about 5 mM BEI; and ix) adding of an equivalent amount of an agent that neutralizes the inactivation agent within the solution, preferably, adding of a sodium thiosulfate solution to a final concentration of about 1 to about 20 mM, preferably of about 5 mM, when the inactivation agent is BEI.

In another aspect of the present invention, a method for preparing a composition, preferably an antigenic composition, such as for example a vaccine, for invoking an immune response against PCV2 is provided. Generally, this method includes the steps of transfecting a construct into a virus, wherein the construct comprises i) recombinant DNA from ORF2 of PCV2, ii) infecting cells in growth media with the transfected virus, iii) causing the virus to express the recombinant protein from PCV2 ORF2, iv) recovering the expressed ORF2 protein from the supernate, v) and preparing the composition by combining the recovered protein with a suitable adjuvant and/or other pharmaceutically acceptable carrier.

"Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from theoligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (Phameuropa Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Cabopol 971P. Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from $E.$ $coli$ (recombinant or otherwise), cholera toxin, IMS 1314 or muramyl dipeptide among many others.

Preferably, the adjuvant is added in an amount of about 100 μg to about 10 mg per dose. Even more preferred the adjuvant is added in an amount of about 100 μg to about 10 mg per dose. Even more preferred the adjuvant is added in an amount of about 500 μg to about 5 mg per dose. Even more preferred the adjuvant is added in an amount of about 750 μg to about 2.5 mg per dose. Most preferred the adjuvant is added in an amount of about 1 mg per dose.

Thus, according to a further aspect, the method for preparing an antigenic composition, such as for example a vaccine, for invoking an immune response against PCV2 comprises i) preparing and recovering PCV2 ORF2 protein, and ii) admixing this with a suitable adjuvant. Preferably, the adjuvant is Carbopol 971P. Even more preferred, Carbopol 971P is added in an amount of about 500 μg to about 5 mg per dose, even more preferred in an amount of about 750 μg to about 2.5 mg per dose and most preferred in an amount of about 1 mg per dose. Preferably, the process step i) includes the process steps as described for the preparation and recovery of PCV2 ORF2. For example, in preferred forms of this method, the construct comprising PCV2 ORF2 DNA is obtained in a transfer vector. Suitable transfer vectors and methods of preparing them are described above. Optionally, the method may include the step of amplifying the ORF2 from a strain of PCV2 through PCR prior to cloning the ORF2 into the transfer vector. Preferred open reading frame sequences, Kozak's sequences, 3' EcoR1 site sequences, recombinant protein sequences, transfected construct sequences, media, cells, and viruses are as described in the previous methods. Another optional step for this method includes cloning the amplified PCV2 ORF2 DNA into a first vector, excising the ORF2 DNA from this first vector, and using this excised PCV2 ORF2 DNA for cloning into the transfer vector. As with the other methods, it is preferred to wait for at least 5 days after infection of the cells by the transfected baculovirus prior to recovery of recombinant ORF2 protein from the supernate. Preferably, the recovery step of this method also includes the step of separating the media from the cells and cell debris. This can be done in a variety of ways but for ease and convenience, it is preferred to filter the cells, cell debris, and growth media through a filter having pores ranging in size from about 0.45 μM to about 1.0 μM. Finally, for this method, it is preferred to include a virus inactivation step prior to combining the recovered recombinant PCV2 ORF2 protein in a composition. This can be done in a variety of ways, but it is preferred in the practice of the present invention to use BEI.

Thus according to a further aspect, this method comprises the steps: i) amplifying PCV2 ORF2 DNA in vitro, wherein the flanking sequences of said PCV2 ORF2 DNA are modified, ii) cloning the amplified PCV2 ORF2 DNA into a transfer vector; and iii) transfecting the transfer vector or a portion thereof containing the recombinant PCV2 ORF2 DNA into a viral vector to generate the recombinant viral vector, iv) infecting cells in media with the transfected virus; v) causing the transfected virus to express the recombinant protein from PCV2 ORF2; vi) separating cells from the supernate; vii) recovering the expressed PCV2 ORF2 protein from the supernate; viii) inactivating the recombinant viral vector, preferably, in the presence of about 1 to about 20 mM BEI, most preferred in the presence of about 5 mM BEI; ix) adding of an equivalent amount of an agent that neutralizes the inactivation agent within the solution, preferably, adding of a sodium thiosulfate solution to a final concentration of about 1 to about 20 mM, preferably of about 5 mM, when the inactivation agent is BEI, and x) adding a suitable amount of an adjuvant, preferably adding Carbopol, more preferably Carbopol 971P, even more preferred in amounts as described above (e.g. of about 500 μg to about 5 mg per dose, even more preferred in an amount of about 750 μg to about 2.5 mg per dose and most preferred in an amount of about 1 mg per dose).

Additionally, the composition can include one or more pharmaceutical-acceptable carriers. As used herein, "a pharmaceutical-acceptable carrier" includes any and all solvents, dispersion media, coatings, stabilizing agents, diluents, preservatives, antibacterial and antifungal agents, isotonic agents, adsorption delaying agents, and the like. Most preferred, the composition provided herewith, contains PCV2 ORF2 protein recovered from the supernate of in vitro cultured cells, wherein said cells were infected with a recombinant viral vector containing PCV2 ORF2 DNA and expressing PCV2 ORF2 protein, and wherein said cell culture were treated with about 2 to about 8 mM BEI, preferably with about 5 mM BEI to inactivate the viral vector, and an equivalent concentration of a neutralization agent, preferably sodium thiosulfate solution to a final concentration of about 2 to about 8 mM, preferably of about 5 mM, Carbopol, more preferably Carbopol 971P, preferably in amounts of about 500 μg to about 5 mg per dose, even more preferred in an amount of about 750 μg to about 2.5 mg per dose and most preferred in an amount of about 1 mg per dose, and physiological saline, preferably in an amount of about 50 to about 90% (v/v), more preferably to about 60 to 80% (v/v), still more preferably of about 70% (v/v).

Thus, a further aspect relates to a method for preparing an antigenic composition, such as for example a vaccine, for invoking an immune response against PCV2 comprising the steps: i) amplifying PCV2 ORF2 DNA in vitro, wherein the flanking sequences of said PCV2 ORF2 DNA are modified, ii) cloning the amplified PCV2 ORF2 DNA into a transfer vector; and iii) transfecting the transfer vector or a portion thereof containing the recombinant PCV2 ORF2 DNA into a viral vector to generate the recombinant viral vector, iv) infecting cells in media with the transfected virus; v) causing the transfected virus to express the recombinant protein from PCV2 ORF2; vi) separating cells from the supernate; vii) recovering the expressed PCV2 ORF2 protein from the supernate; viii) inactivating the recombinant viral vector, preferably, in the presence of about 2 to about 20 mM BEI, most preferred in the presence of about 5 mM BEI; ix) adding of an equivalent amount of an agent that neutralize the inactivation agent within the solution, preferably, adding of a sodium thiosulfate solution to a final concentration of about 0.5 to about 20 mM, preferably of about 5 mM, when the inactivation agent is BEI, x) adding a suitable amount of an adjuvants, preferably adding Carbopol, more preferably Carbopol 971P, still more preferred in amounts as described above (e.g. of about 500 μg to about 5 mg per dose, even more preferred in an amount of about 750 μg to about 2.5 mg per dose and most preferred in an amount of about 1 mg per dose); and xi) adding physiological saline, preferably in an amount of about 50 to about 90% (v/v), more preferably to about 60 to 80% (v/v), still more preferably of about 70% (v/v). Optionally, this method can also include the addition of a protectant. A protectant as used herein, refers to an anti-microbiological active agent, such as for example Gentamycin, Merthiolate, and the like. In particular adding of a protectant is most preferred for the preparation of a multi-dose composition. Those anti-microbiological active agents are added in concentrations effective to prevent the composition of interest for any microbiological contamination or for inhibition of any microbiological growth within the composition of interest.

Moreover, this method can also comprise addition of any stabilizing agent, such as for example saccharides, trehalose, mannitol, saccharose and the like, to increase and/or maintain product shelf-life. However, it has been surprisingly found, that the resulting formulation is immunologically effective over a period of at least 24 months, without adding any further stabilizing agent.

A further aspect of the present invention relates to the products result from the methods as described above. In particular, the present invention relates to a composition of matter comprises recombinantly expressed PCV2 ORF2 protein. Moreover, the present invention also relates to a composition of matter that comprises recombinantly expressed PCV2 ORF2 protein, recovered from the supernate of an insect cell culture. Moreover, the present invention also relates to a composition of matter comprises recombinantly expressed PCV2 ORF2 protein, recovered from the supernate of an insect cell culture. Preferably, this composition of matter also comprises an agent suitable for the inactivation of viral vectors. Preferably, said inactivation agent is BEI. Moreover, the present invention also relates to a composition of matter that comprises recombinantly expressed PCV2 ORF2 protein, recovered from the supernate of an insect cell culture, and comprises an agent, suitable for the inactivation of viral vectors, preferably BEI and a neutralization agent for neutralization of the inactivation agent. Preferably, that neutralization agent is sodium thiosulfate, when BEI is used as an inactivation agent.

In yet another aspect of the present invention, an immunogenic composition that induces an immune response and, more preferably, confers protective immunity against the clinical signs of PCV2 infection, is provided. The composition generally comprises the polypeptide, or a fragment thereof, expressed by Open Reading Frame 2 (ORF2) of PCV2, as the antigenic component of the composition.

PCV2 ORF2 DNA and protein, as used herein for the preparation of the compositions and also as used within the processes provided herein is a highly conserved domain within PCV2 isolates and thereby, any PCV2 ORF2 would be effective as the source of the PCV ORF2 DNA and/or polypeptide as used herein. A preferred PCV2 ORF2 protein is that of SEQ ID NO. 11. A preferred PCV ORF2 polypeptide is provided herein as SEQ ID NO. 5, but it is understood by those of skill in the art that this sequence could vary by as much as 6-10% in sequence homology and still retain the antigenic characteristics that render it useful in immunogenic compositions. The antigenic characteristics of an immunological composition can be, for example, estimated by the challenge experiment as provided by Example 4. Moreover, the antigenic characteristic of an modified antigen is still retained, when the modified antigen confers at least 70%, preferably 80%, more preferably 90% of the protective immunity as compared to the PCV2 ORF 2 protein, encoded by the polynucleotide sequence of SEQ ID NO:3 or SEQ ID NO:4. An "immunogenic composition" as used herein, means a PCV2 ORF2 protein which elicits an "immunological response" in the host of a cellular and/or antibody-mediated immune response to PCV2 ORF2 protein. Preferably, this immunogenic composition is capable to confer protective immunity against PCV2 infection and the clinical signs associated therewith. In some forms, immunogenic portions of PCV2 ORF2 protein are used as the antigenic component in the composition. The term "immunogenic portion" as used herein refers to truncated and/or substituted forms, or fragments of PCV2 ORF2 protein and/or polynucleotide, respectively. Preferably, such truncated and/or substituted forms, or fragments will comprise at least 6 contiguous amino acids from the full-length ORF2 polypeptide. More preferably, the truncated or substituted forms, or fragments will have at least 10, more preferably at least 15, and still more preferably at least 19 contiguous amino acids from the full-length ORF2 polypeptide. Two preferred sequences in this respect are provided herein as SEQ ID NOs. 9 and 10. It is further understood that such sequences may be a part of larger fragments or truncated forms. A further preferred PCV2 ORF2 polypeptide provided herein is encoded by the nucleotide sequences of SEQ ID NO: 3 or SEQ ID NO: 4. But it is understood by those of skill in the art that this sequence could vary by as much as 6-20% in sequence homology and still retain the antigenic characteristics that render it useful in immunogenic compositions. In some forms, a truncated or substituted form, or fragment of ORF2 is used as the antigenic component in the composition. Preferably, such truncated or substituted forms, or fragments will comprise at least 18 contiguous nucleotides from the full-length ORF2 nucleotide sequence, e.g. of SEQ ID NO: 3 or SEQ ID NO: 4. More preferably, the truncated or substituted forms, or fragments will have at least 30, more preferably at least 45, and still more preferably at least 57 contiguous nucleotides the full-length ORF2 nucleotide sequence, e.g. of SEQ ID NO: 3 or SEQ ID NO: 4.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

"Sequence homology", as used herein, refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence. Preferably the homolog sequence comprises at least a stretch of 50, even more preferred of 100, even more preferred of 250, even more preferred of 500 nucleotides.

A "conservative substitution" refers to the substitution of an amino acid residue or nucleotide with another amino acid residue or nucleotide having similar characteristics or properties including size, hydrophobicity, etc., such that the overall functionality does not change significantly.

Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Thus, a further aspect of the present invention relates to an immunogenic composition effective for lessening the severity of clinical symptoms associated with PCV2 infection comprising PCV2 ORF2 protein. Preferably, the PCV2 ORF2 protein is anyone of those, described above. Preferably, said PCV2 ORF2 protein is i) a polypeptide comprising the sequence of SEQ ID NO: 5, SEQ ID NO: 6, SEQ ID NO: 9, SEQ ID NO: 10 or SEQ ID NO: 11;
ii) any polypeptide that is at least 80% homologous to the polypeptide of i),
iii) any immunogenic portion of the polypeptides of i) and/or ii)
iv) the immunogenic portion of iii), comprising at least 10 contiguous amino acids included in the sequences of SEQ ID NO: 5, SEQ ID NO: 6, SEQ ID NO: 9, SEQ ID NO: 10 or SEQ ID NO: 11,
v) a polypeptide that is encoded by a DNA comprising the sequence of SEQ ID NO: 3 or SEQ ID NO: 4.
iv) any polypeptide that is encoded by a polynucleotide that is at least 80% homolog to the polynucleotide of v),
vii) any immunogenic portion of the polypeptides encoded by the polynucleotide of v) and/or vi)
viii) the immunogenic portion of vii), wherein polynucleotide coding for said immunogenic portion comprises at least 30 contiguous nucleotides included in the sequences of SEQ ID NO: 3, or SEQ ID NO: 4.

Preferably any of those immunogenic portions having the immunogenic characteristics of PCV2 ORF2 protein that is encoded by the sequence of SEQ ID NO: 3 or SEQ ID NO: 4.

According to a further aspect, PCV2 ORF2 protein is provided in the immunological composition at an antigen inclusion level effective for inducing the desired immune response, namely reducing the incidence of or lessening the severity of clinical signs resulting from PCV2 infection. Preferably, the PCV2 ORF2 protein inclusion level is at least 0.2 µg antigen/ml of the final immunogenic composition (µg/ml), more preferably from about 0.2 to about 400 µg/ml, still more preferably from about 0.3 to about 200 µg/ml, even more preferably from about 0.35 to about 100 µg/ml, still more preferably from about 0.4 to about 50 µg/ml, still more preferably from about 0.45 to about 30 µg/ml, still more preferably from about 0.6 to about 15 µg/ml, even more preferably from about 0.75 to about 8 µg/ml, even more preferably from about 1.0 to about 6 µg/ml, still more preferably from about 1.3 to about 3.0 µg/ml, even more preferably from about 1.4 to about 2.5 µg/ml, even more preferably from about 1.5 to about 2.0 µg/ml, and most preferably about 1.6 µg/ml.

According to a further aspect, the ORF2 antigen inclusion level is at least 0.2 µg PCV2 ORF2 protein as described above per dose of the final antigenic composition (µg/dose), more preferably from about 0.2 to about 400 µg/dose, still more preferably from about 0.3 to about 200 µg/dose, even more preferably from about 0.35 to about 100 µg/dose, still more preferably from about 0.4 to about 50 µg/dose, still more preferably from about 0.45 to about 30 µg/dose, still more preferably from about 0.6 to about 15 µg/dose, even more preferably from about 0.75 to about 8 µg/dose, even more preferably from about 1.0 to about 6 µg/dose, still more preferably from about 1.3 to about 3.0 µg/dose, even more preferably from about 1.4 to about 2.5 µg/dose, even more preferably from about 1.5 to about 2.0 µg/dose, and most preferably about 1.6 µg/dose.

The PCV2 ORF2 polypeptide used in an immunogenic composition in accordance with the present invention can be derived in any fashion including isolation and purification of PCV2 ORF2, standard protein synthesis, and recombinant methodology. Preferred methods for obtaining PCV2 ORF2 polypeptide are described herein above and are also provided in U.S. patent application Ser. No. 11/034,797, the teachings and content of which are hereby incorporated by reference. Briefly, susceptible cells are infected with a recombinant viral vector containing PCV2 ORF2 DNA coding sequences, PCV2 ORF2 polypeptide is expressed by the recombinant virus, and the expressed PCV2 ORF2 polypeptide is recovered from the supernate by filtration and inactivated by any conventional method, preferably using binary ethylenimine, which is then neutralized to stop the inactivation process.

Thus, according to a further aspect the immunogenic composition comprises i) any of the PCV2 ORF2 protein described above, preferably in concentrations described above, and ii) at least a portion of the viral vector expressing said PCV2 ORF2 protein, preferably of a recombinant baculovirus. Moreover, according to a further aspect, the immunogenic composition comprises i) any of the PCV2 ORF2 protein described above, preferably in concentrations described above, ii) at least a portion of the viral vector expressing said PCV2 ORF2 protein, preferably of a recombinant baculovirus, and iii) a portion of the cell culture supernate.

According to one specific embodiment of the production and recovery process for PCV2 ORF2 protein, the cell culture supernate is filtered through a membrane having a pore size, preferably between about 0.45 to 1 µm. Thus, a further aspect relates to an immunogenic composition that comprises i) any of the PCV2 ORF2 protein described above, preferably in concentrations described above, ii) at least a portion of the viral vector expressing said PCV2 ORF2 protein, preferably of a recombinant baculovirus, and iii) a portion of the cell culture; wherein about 90% of the components have a size smaller than 1 µm.

According to a further aspect, the present invention relates to an immunogenic composition that comprises i) any of the PCV2 ORF2 protein described above, preferably in concentrations described above, ii) at least a portion of the viral vector expressing said PCV2 ORF2 protein, iii) a portion of the cell culture, iv) and inactivating agent to inactivate the recombinant viral vector preferably BEI, wherein about 90% of the components i) to iii) have a size smaller than 1 µm.

Preferably, BEI is present in concentrations effective to inactivate the baculovirus. Effective concentrations are described above.

According to a further aspect, the present invention relates to an immunogenic composition that comprises i) any of the PCV2 ORF2 protein described above, preferably in concentrations described above, ii) at least a portion of the viral vector expressing said PCV2 ORF2 protein, iii) a portion of the cell culture, iv) an inactivating agent to inactivate the recombinant viral vector preferably BEI, and v) an neutralization agent to stop the inactivation mediated by the inactivating agent, wherein about 90% of the components i) to iii) have a size smaller than 1 µm. Preferably, if the inactivating agent is BEI, said composition comprises sodium thiosulfate in equivalent amounts to BEI.

The polypeptide is incorporated into a composition that can be administered to an animal susceptible to PCV2 infection. In preferred forms, the composition may also include additional components known to those of skill in the art (see also Remington's Pharmaceutical Sciences. (1990). 18th ed. Mack Publ., Easton). Additionally, the composition may include one or more veterinary-acceptable carriers. As used herein, "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like.

In a preferred embodiment, the immunogenic composition comprises PCV2 ORF2 protein as provided herewith, preferably in concentrations described above as an antigenic component, which is mixed with an adjuvant, preferably Carbopol, and physiological saline.

Those of skill in the art will understand that the composition herein may incorporate known injectable, physiologically acceptable sterile solutions. For preparing a ready-to-use solution for parenteral injection or infusion, aqueous isotonic solutions, such as e.g. saline or corresponding plasma protein solutions are readily available. In addition, the immunogenic and vaccine compositions of the present invention can include diluents, isotonic agents, stabilizers, or adjuvants. Diluents can include water, saline, dextrose, ethanol, glycerol, and the like. Isotonic agents can include sodium chloride, dextrose, mannitol, sorbitol, and lactose, among others. Stabilizers include albumin and alkali salts of ethylendiamintetracetic acid, among others. Suitable adjuvants, are those described above. Most preferred is the use of Carbopol, in particular the use of Carbopol 971P, preferably in amounts as described above (e.g. of about 500 µg to about 5 mg per dose, even more preferred in an amount of about 750 µg to about 2.5 mg per dose and most preferred in an amount of about 1 mg per dose).

Thus, the present invention also relates to an immunogenic composition that comprises i) any of the PCV2 ORF2 proteins described above, preferably in concentrations described above, ii) at least a portion of the viral vector expressing said PCV2 ORF2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; and vi) a suitable adjuvant, preferably Carbopol 971 in amounts described above; wherein about 90% of the components i) to iii) have a size smaller than 1 µm. According to a further aspect, this immunogenic composition further comprises a pharmaceutical acceptable salt, preferably a phosphate salt in physiologically acceptable concentrations. Preferably, the pH of said immunogenic composition is adjusted to a physiological pH, meaning between about 6.5 and 7.5.

Thus, the present invention also relates to an immunogenic composition comprises per one ml i) at least 1.6 µg of PCV2 ORF2 protein described above, ii) at least a portion of baculovirus expressing said PCV2 ORF2 protein iii) a portion of the cell culture, iv) about 2 to 8 mM BEI, v) sodium thiosulfate in equivalent amounts to BEI; and vi) about 1 mg Carbopol 971, and vii) phosphate salt in a physiologically acceptable concentration; wherein about 90% of the components i) to iii) have a size smaller than 1 µm and the pH of said immunogenic composition is adjusted to about 6.5 to 7.5.

The immunogenic compositions can further include one or more other immunomodulatory agents such as, e.g., interleukins, interferons, or other cytokines. The immunogenic compositions can also include Gentamicin and Merthiolate. While the amounts and concentrations of adjuvants and additives useful in the context of the present invention can readily be determined by the skilled artisan, the present invention contemplates compositions comprising from about 50 µg to about 2000 µg of adjuvant and preferably about 250 µg/ml dose of the vaccine composition. In another preferred embodiment, the present invention contemplates vaccine compositions comprising from about 1 ug/ml to about 60 µg/ml of antibiotics, and more preferably less than about 30 µg/ml of antibiotics.

Thus, the present invention also relates to an immunogenic composition that comprises i) any of the PCV2 ORF2 proteins described above, preferably in concentrations described above, ii) at least a portion of the viral vector expressing said PCV2 ORF2 protein, iii) a portion of the cell culture, iv) an inactivating agent to inactivate the recombinant viral vector preferably BEI, and v) an neutralization agent to stop the inactivation mediated by the inactivating agent, preferably sodium thiosulfate in equivalent amounts to BEI; vi) a suitable adjuvant, preferably Carbopol 971 in amounts described above; vii) a pharmaceutical acceptable concentration of a saline buffer, preferably of a phosphate salt, and viii) an anti-microbiological active agent; wherein about 90% of the components i) to iii) have a size smaller than 1 µm.

It has been surprisingly found, that the immunogenic composition provided herewith comprises was highly stable over a period of 24 months. It has also been found the immunogenic compositions provided herewith, comprising recombinant, baculovirus expressed PCV2 ORF2 protein as provided herewith are very effective in reducing the clinical symptoms associated with PCV2 infections. It has been surprisingly found, that the immunogenic compositions comprising the recombinant baculovirus expressed PCV2 ORF2 protein as provided herewith, are more effective than an immunogenic composition comprising the whole PCV2 virus in an inactivated form, or isolated viral PCV2 ORF2 antigen. In particular, it has been surprisingly found, that the recombinant baculovirus expressed PCV2 ORF2 protein is effective is in very low concentrations, which means in concentrations up to 0.25 µg/dose. This unexpected high immunogenic potential of the PCV2 ORF2 protein could be further increased by the addition of Carbopol.

A further aspect relates to a container comprises at least one dose of the immunogenic composition of PCV2 ORF2 protein as provided herewith, wherein one dose comprises at least 2 µg PCV2 ORF2 protein, preferably 2 to 16 µg PCV2 ORF2 protein. Said container can comprises 1 to 250 doses of the immunogenic composition, preferably it contains 1, 10, 25, 50, 100, 150, 200, or 250 doses of the immunogenic composition of PCV2 ORF2 protein. Preferably, each of the containers comprising more than one dose of the immunogenic composition of PCV2 ORF2 protein further comprises an anti-microbiological active agent. Those agents are for example antibiotics including Gentamicin and Merthiolate and the like. Thus, one aspect of the present invention relates to a container that comprises 1 to 250 doses of the immunogenic composition of PCV2 ORF2 protein, wherein one dose comprises at least 2 µg PCV2 ORF2 protein, and Gentamicin and/or Merthiolate, preferably from about 1 µg/ml to about 60 µg/ml of antibiotics, and more preferably less than about 30 µg/ml.

A further aspect relates to a kit, comprising any of the containers, described above, and an instruction manual, including the information for the intramuscular application of at least one dose of the immunogenic composition of PCV2 ORF2 protein into piglets to lessening the severity of clinical symptoms associated with PCV2 infection. Moreover, according to a further aspect, said instruction manual comprises the information of a second or further administration(s) of at least one dose of the immunogenic composition of PCV2 ORF2, wherein the second administration or any further administration is at least 14 days beyond the initial or any former administration. Preferably, said instruction manual also includes the information, to administer an immune stimulant. Preferably, said immune stimulant shall be given at least twice. Preferably, at least 3, more preferably at least 5, even more preferably at least 7 days are between the first and the second or any further administration of the immune stimulant. Preferably, the immune stimulant is given at least 10 days, preferably 15, even more preferably 20, even more preferably at least 22 days beyond the initial administration of the immunogenic composition of PCV2 ORF2 protein. A preferred immune stimulant is for example is keyhole limpet hemocyanin (KLH), still preferably emulsified with incomplete Freund's adjuvant (KLH/ICFA). However, it is herewith understood, that any other immune stimulant known to a person skilled in the art can also be used. "Immune stimulant" as used herein, means any agent or composition that can trigger the immune response, preferably without initiating or increasing a specific immune response, for example the immune response against a specific pathogen. It is further instructed to administer the immune stimulant in a suitable dose. Moreover, the kit may also comprises a container, including at least one dose of the immune stimulant, preferably one dose of KLH, or KLH/ICFA.

Moreover, it has also been surprisingly found that the immunogenic potential of the immunogenic compositions comprising recombinant baculovirus expressed PCV2 ORF2 protein, preferably in combination with Carbopol, can be further enhanced by the administration of the IngelVac PRRS MLV vaccine (see Example 5). PCV2 clinical signs and disease manifestations are greatly magnified when PRRS infection is present. However, the immunogenic compositions and vaccination strategies as provided herewith lessened this effect greatly, and more than expected. In other words, an unexpected synergistic effect was observed when animals, preferably pigs are treated with any of the PCV2 ORF2 immunogenic composition, as provided herewith, and the Ingelvac PRRS MLV vaccine (Boehringer Ingelheim).

Thus, a further aspect of the present invention relates to the kit as described above, comprising the immunogenic composition of PCV2 ORF2 as provided herewith and the instruction manual, wherein the instruction manual further include the information to administer the PCV2 ORF2 immunogenic composition together with immunogenic composition that comprises PRRS antigen, preferably adjuvanted PRRS antigen. Preferably, the PRRS antigen is adjuvanted with Carbopol. Preferably, the PRRS antigen is IngelVac® PRRS MLV (Boehringer Ingelheim).

A further aspect of the present invention also relates to a kit comprising i) a container containing at least one dose of an immunogenic composition of PCV2 ORF2 as provided herewith, and ii) a container containing an immunogenic composition comprising PRRS antigen, preferably adjuvanted PRRS antigen. Preferably, the PRRS antigen is adjuvanted with Carbopol. Preferably the PRRS antigen is IngelVac® PRRS MLV (Boehringer Ingelheim). More preferably, the kit further comprises an instruction manual, including the information to administer both pharmaceutical compositions. Preferably, it contains the information that the PCV2 ORF2 containing composition is administered temporally prior to the PRRS containing composition.

A further aspect, relates to the use of any of the compositions provided herewith as a medicament, preferably as a veterinary medicament, even more preferred as a vaccine. Moreover, the present invention also relates to the use of any of the compositions described herein, for the preparation of a medicament for lessening the severity of clinical symptoms associated with PCV2 infection. Preferably, the medicament is for the prevention of a PCV2 infection, even more preferably in piglets.

A further aspect relates to a method for (i) the prevention of an infection, or re-infection with PCV2 or (ii) the reduction or elimination of clinical symptoms caused by PCV2 in a subject, comprising administering any of the immunogenic compositions provided herewith to a subject in need thereof. Preferably, the subject is a pig. Preferably, the immunogenic composition is administered intramuscular. Preferably, one dose or two doses of the immunogenic composition is/are administered, wherein one dose preferably comprises at least about 2 µg PCV2 ORF2 protein, even more preferably about 2 to about 16 µg, and at least about 0.1 to about 5 mg Carbopol, preferably about 1 mg Carbopol. A further aspect relates to the method of treatment as described above, wherein a second application of the immunogenic composition is administered. Preferably, the second administration is done with the same immunogenic composition, preferably having the same amount of PCV2 ORF2 protein. Preferably the second administration is also given intramuscular. Preferably, the second administration is done at least 14 days beyond the initial administration, even more preferably at least 4 weeks beyond the initial administration.

According to a further aspect, the method of treatment also comprises the administration of an immune stimulant. Preferably, said immune stimulant is administered at least twice. Preferably, at least 3, more preferably at least 5 days, even more preferably at least 7 days are between the first and the second administration of the immune stimulant. Preferably, the immune stimulant is administered at least 10 days, preferably 15, even more preferably 20, even more preferably at least 22 days beyond the initial administration of the PCV2 ORF2 immunogenic composition. A preferred immune stimulant is for example is keyhole limpet hemocyanin (KLH), still preferably emulsified with incomplete Freund's adjuvant (KLH/ICFA). However, it is herewith understood, that any other immune stimulant known to a person skilled in the art can also be used. It is within the general knowledge of a person skilled in the art to administer the immune stimulant in a suitable dose.

According to a further aspect, the method of treatments described above also comprises the administration of PRRS antigen. Preferably, the PRRS antigen is adjuvanted with Carbopol. Preferably the PRRS antigen is IngelVac® PRRS MLV (Boehringer Ingelheim). Preferably, said PRRS antigen is administered temporally beyond the administration of the immunogenic composition of PCV2 ORF2 protein.

BRIEF DESCRIPTION OF THE DRAWINGS

FIGS. 2a and 2b are a schematic flow diagram of how to produce a composition in accordance with the present invention.

DETAILED DESCRIPTION OF THE PREFERRED EMBODIMENTS

The following examples set forth preferred materials and procedures in accordance with the present invention. It is to be understood, however, that these examples are provided by way of illustration only, and nothing therein should be deemed a limitation upon the overall scope of the invention.

EXAMPLE 1

This example compares the relative yields of ORF2 using methods of the present invention with methods that are known in the prior art. Four 1000 mL spinner flasks were each seeded with approximately $1.0 \times 10^6$ Sf+ cells/ml in 300 mL of insect serum free media, Excell 420 (JRH Biosciences, Inc., Lenexa, Kans.). The master cell culture is identified as SF+ (*Spodoptera frugiperda*) Master Cell Stock, passage 19, Lot#N112-095W. The cells used to generate the SF+ Master Cell Stock were obtained from Protein Sciences Corporation, Inc., Meriden, Conn. The SF+ cell line for this example was confined between passages 19 and 59. Other passages will work for purposes of the present invention, but in order to scale the process up for large scale production, at least 19 passages will probably be necessary and passages beyond 59 may have an effect on expression, although this was not investigated. In more detail, the initial SF+ cell cultures from liquid nitrogen storage were grown in Excell 420 media in suspension in sterile spinner flasks with constant agitation. The cultures were grown in 100 mL to 250 mL spinner flasks with 25 to 150 mL of Excell 420 serum-free media. When the cells had multiplied to a cell density of $1.0\text{-}8.0 \times 10^6$ cells/mL, they were split to new vessels with a planting density of $0.5\text{-}1.5 \times 10^6$ cells/mL. Subsequent expansion cultures were grown in spinner flasks up to 36 liters in size or in stainless steel bioreactors of up to 300 liters for a period of 2-7 days at 25-29° C.

Figure 1:
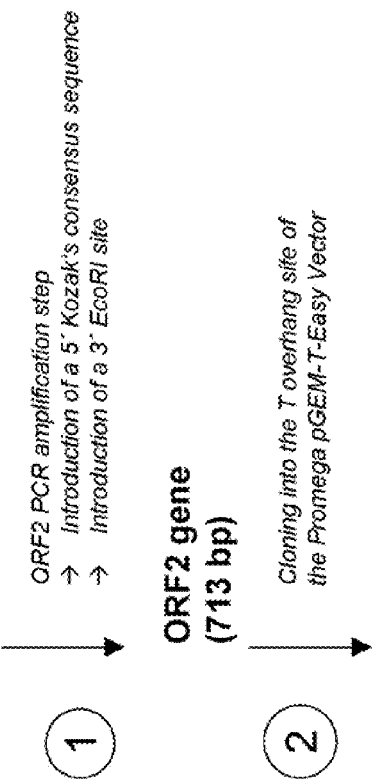
FIG. 1 is a schematic flow diagram of a preferred construction of PCV2 ORF2 recombinant baculovirus.
Figure 1:
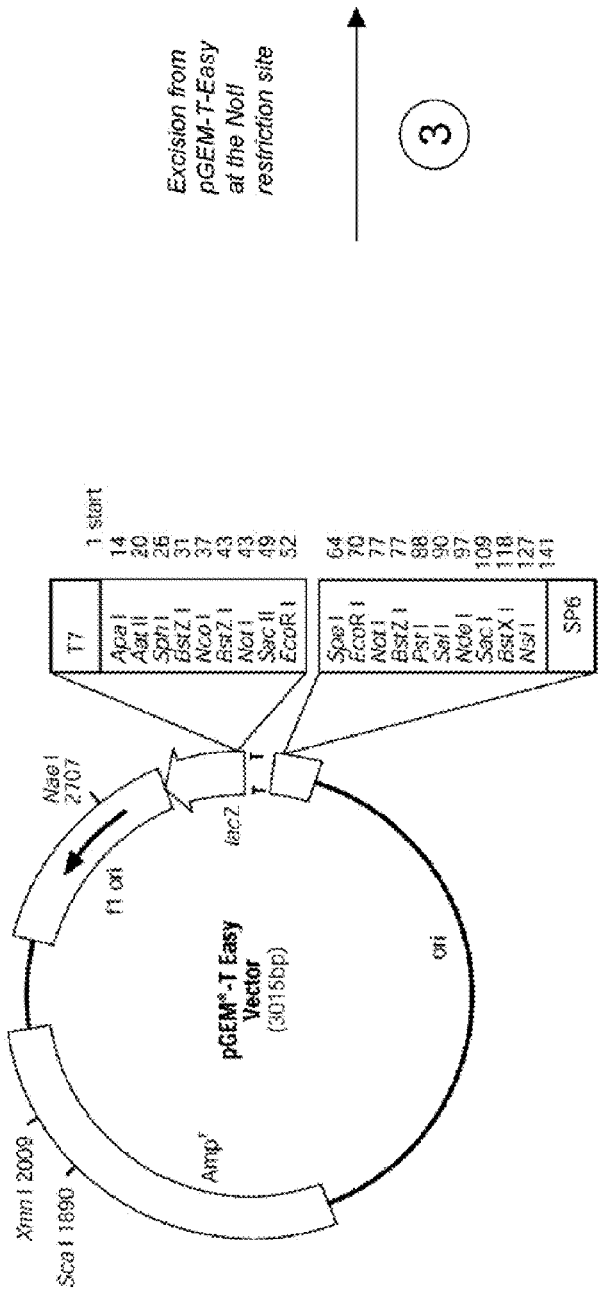
Figure 1:
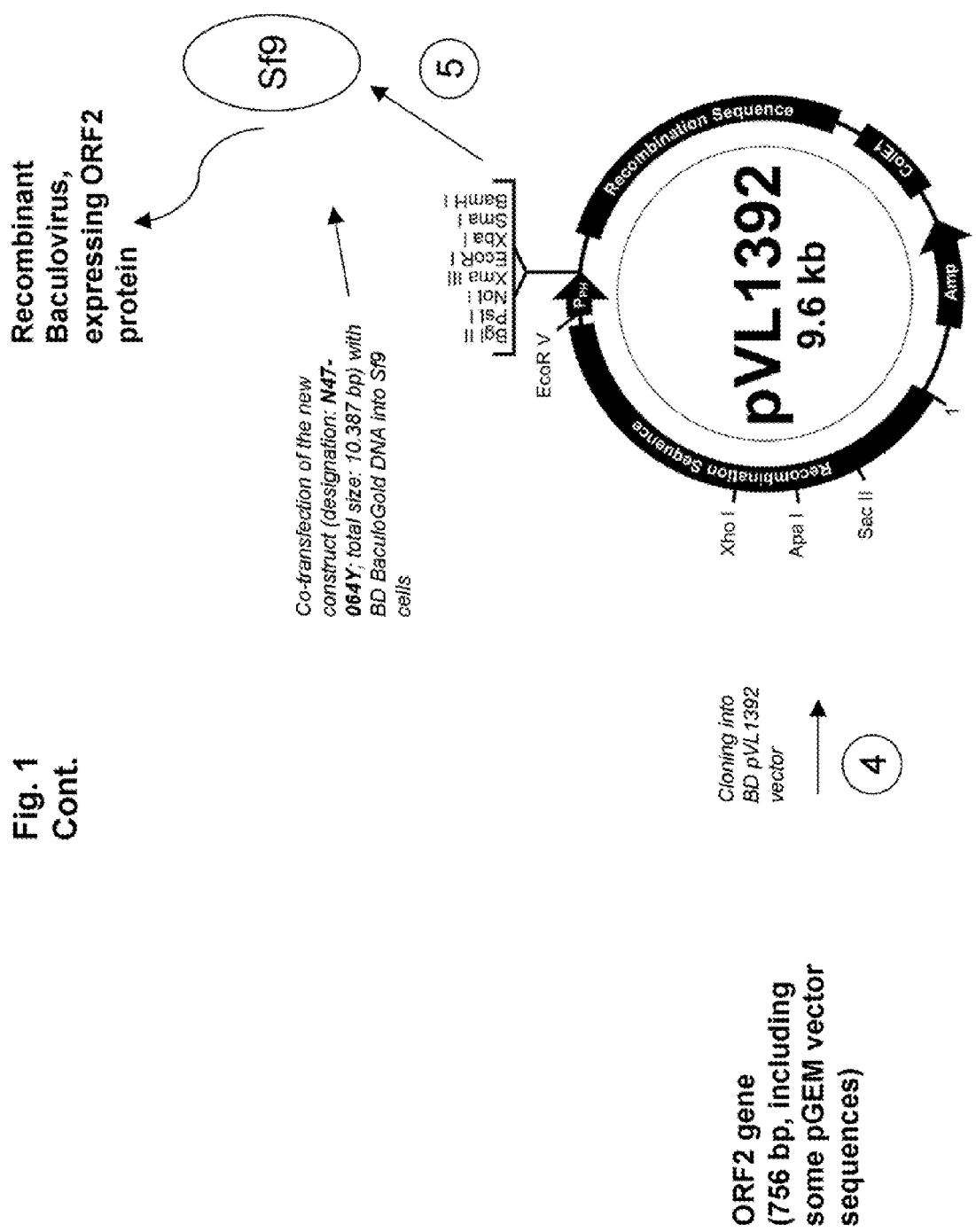
Figure 2B:
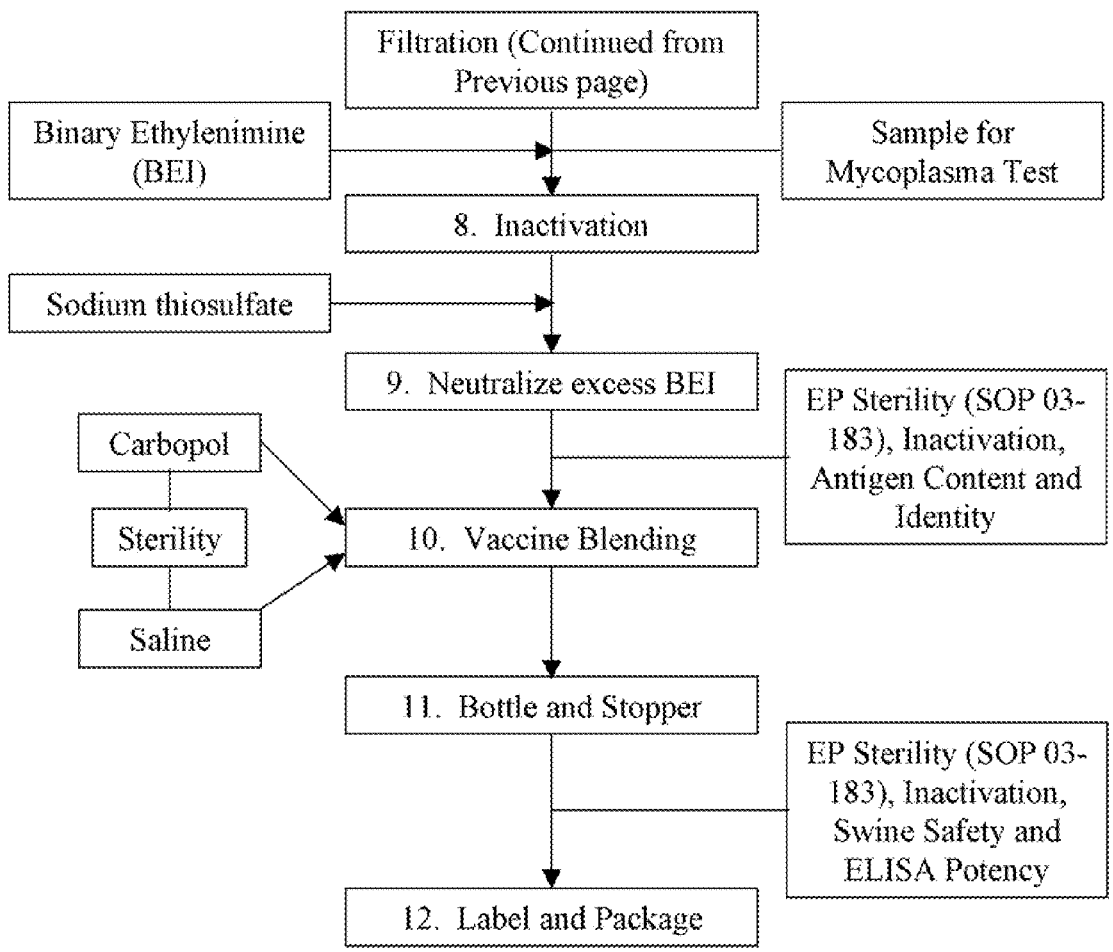

After seeding, the flasks were incubated at 27° C. for four hours. Subsequently, each flask was seeded with a recombinant baculovirus containing the PCV2 ORF2 gene (SEQ ID NO: 4). The recombinant baculovirus containing the PCV2 ORF2 gene was generated as follows: the PCV2 ORF2 gene from a North American strain of PCV2 was PCR amplified to contain a 5' Kozak's sequence (SEQ ID NO: 1) and a 3' EcoR1 site (SEQ ID NO: 2), cloned into the pGEM-T-Easy vector (Promega, Madison, Wis.). Then, it was subsequently excised and subcloned into the transfer vector pVL1392 (BD Biosciences Pharmingen, San Diego, Calif.). The subcloned portion is represented herein as SEQ ID NO: 7. The pVL1392 plasmid containing the PCV2 ORF2 gene was designated N47-064Y and then co-transfected with BaculoGold® (BD Biosciences Pharmingen) baculovirus DNA into Sf+ insect cells (Protein Sciences, Meriden, Conn.) to generate the recombinant baculovirus containing the PCV2 ORF2 gene. The new construct is provided herein as SEQ ID NO: 8. The recombinant baculovirus containing the PCV2 ORF2 gene was plaque-purified and Master Seed Virus (MSV) was propagated on the SF+ cell line, aliquotted, and stored at −70° C. The MSV was positively identified as PCV2 ORF2 baculovirus by PCR-RFLP using baculovirus specific primers. Insect cells infected with PCV2 ORF2 baculovirus to generate MSV or Working Seed Virus express PCV2 ORF2 antigen as detected by polyclonal serum or monoclonal antibodies in an indirect fluorescent antibody assay. Additionally, the identity of the PCV2 ORF2 baculovirus was confirmed by N-terminal amino acid sequencing. The PCV2 ORF2 baculovirus MSV was also tested for purity in accordance with 9 C.F.R. 113.27 (c), 113.28, and 113.55. Each recombinant baculovirus seeded into the spinner flasks had varying multiplicities of infection (MOIs). Flask 1 was seeded with 7.52 mL of 0.088 MOI seed; flask 2 was seeded with 3.01 mL of 0.36 MOI seed; flask 3 was seeded with 1.5 mL of 0.18 MOI seed; and flask 4 was seeded with 0.75 mL of 0.09 MOI seed. A schematic flow diagram illustrating the basic steps used to construct a PCV2 ORF2 recombinant baculovirus is provided herein as FIG. 1.

After being seeded with the baculovirus, the flasks were then incubated at 27±2° C. for 7 days and were also agitated at 100 rpm during that time. The flasks used ventilated caps to allow for air flow. Samples from each flask were taken every 24 hours for the next 7 days. After extraction, each sample was centrifuged, and both the pellet and the supernatant were separated and then microfiltered through a 0.45-1.0 μm pore size membrane.

The resulting samples then had the amount of ORF2 present within them quantified via an ELISA assay. The ELISA assay was conducted with capture antibody Swine anti-PCV2 Pab IgG Prot. G purified (diluted 1:250 in PBS) diluted to 1:6000 in 0.05M Carbonate buffer (pH 9.6). 100 μL of the antibody was then placed in the wells of the mictrotiter plate, sealed, and incubated overnight at 37° C. The plate was then washed three times with a wash solution which comprised 0.5 mL of Tween 20 (Sigma, St. Louis, Mo.), 100 mL of 10× D-PBS (Gibco Invitrogen, Carlsbad, Calif.) and 899.5 mL of distilled water. Subsequently, 250 μL of a blocking solution (5 g Carnation Non-fat dry milk (Nestle, Glendale, Calif.) in 10 mL of D-PBS QS to 100 mL with distilled water) was added to each of the wells. The next step was to wash the test plate and then add pre-diluted antigen. The pre-diluted antigen was produced by adding 200 μL of diluent solution (0.5 mL Tween 20 in 999.5 mL D-PBS) to each of the wells on a dilution plate. The sample was then diluted at a 1:240 ratio and a 1:480 ratio, and 100 μL of each of these diluted samples was then added to one of the top wells on the dilution plate (i.e. one top well received 100 μL of the 1:240 dilution and the other received 100 μL of the 1:480 dilution). Serial dilutions were then done for the remainder of the plate by removing 100 μL form each successive well and transferring it to the next well on the plate. Each well was mixed prior to doing the next transfer. The test plate washing included washing the plate three times with the wash buffer. The plate was then sealed and incubated for an hour at 37° C. before being washed three more times with the wash buffer. The detection antibody used was monoclonal antibody to PCV ORF2. It was diluted to 1:300 in diluent solution, and 100 μL of the diluted detection antibody was then added to the wells. The plate was then sealed and incubated for an hour at 37° C. before being washed three times with the wash buffer. Conjugate diluent was then prepared by adding normal rabbit serum (Jackson Immunoresearch, West Grove, Pa.) to the diluent solution to 1% concentration. Conjugate antibody Goat anti-mouse (H+1)-HRP (Jackson Immunoresearch) was diluted in the conjugate diluent to 1:10,000. 100 μL of the diluted conjugate antibody was then added to each of the wells. The plate was then sealed and incubated for 45 minutes at 37° C. before being washed three times with the wash buffer. 100 μL of substrate (TMB Peroxidase Substrate, Kirkgaard and Perry Laboratories (KPL), Gaithersburg, Md.), mixed with an equal volume of Peroxidase Substrate B (KPL) was added to each of the wells. The plate was incubated at room temperature for 15 minutes. 100 μL of 1N HCL solution was then added to all of the wells to stop the reaction. The plate was then run through an ELISA reader. The results of this assay are provided in Table 1 below:

TABLE 1

| Day | Flask | ORF2 in pellet (μg) | ORF2 in supernatant (μg) |
|---|---|---|---|
| 3 | 1 | 47.53 | 12 |
| 3 | 2 | 57.46 | 22 |
| 3 | 3 | 53.44 | 14 |
| 3 | 4 | 58.64 | 12 |
| 4 | 1 | 43.01 | 44 |
| 4 | 2 | 65.61 | 62 |
| 4 | 3 | 70.56 | 32 |
| 4 | 4 | 64.97 | 24 |
| 5 | 1 | 31.74 | 100 |
| 5 | 2 | 34.93 | 142 |
| 5 | 3 | 47.84 | 90 |
| 5 | 4 | 55.14 | 86 |
| 6 | 1 | 14.7 | 158 |
| 6 | 2 | 18.13 | 182 |
| 6 | 3 | 34.78 | 140 |
| 6 | 4 | 36.88 | 146 |
| 7 | 1 | 6.54 | 176 |
| 7 | 2 | 12.09 | 190 |
| 7 | 3 | 15.84 | 158 |
| 7 | 4 | 15.19 | 152 |

These results indicate that when the incubation time is extended, expression of ORF2 into the supernatant of the centrifuged cells and media is greater than expression in the pellet of the centrifuged cells and media. Accordingly, allowing the ORF2 expression to proceed for at least 5 days and recovering it in the supernate rather than allowing expression to proceed for less than 5 days and recovering ORF2 from the cells, provides a great increase in ORF2 yields, and a significant improvement over prior methods.

EXAMPLE 2

This example provides data as to the efficacy of the invention claimed herein. A 1000 mL spinner flask was seeded with approximately $1.0\times10^6$ Sf+ cells/ml in 300 mL of Excell 420 media. The flask was then incubated at 27° C. and agitated at 100 rpm. Subsequently, the flask was seeded with 10 mL of PCV2 ORF2/Bac p+6 (the recombinant baculovirus containing the PCV2 ORF2 gene passaged 6 additional times in the Sf9 insect cells) virus seed with a 0.1 MOI after 24 hours of incubation.

The flask was then incubated at 27° C. for a total of 6 days. After incubation, the flask was then centrifuged and three samples of the resulting supernatant were harvested and inactivated. The supernatant was inactivated by bringing its temperature to 37±2° C. To the first sample, a 0.4M solution of 2-bromoethyleneamine hydrobromide which had been cyclized to 0.2M binary ethlylenimine (BEI) in 0.3N NaOH is added to the supernatant to give a final concentration of BEI of 5 mM. To the second sample, 10 mM BEI was added to the supernatant. To the third sample, no BEI was added to the supernatant. The samples were then stirred continuously for 48 hrs. A 1.0 M sodium thiosulfate solution to give a final minimum concentration of 5 mM was added to neutralize any residual BEI. The quantity of ORF2 in each sample was then quantified using the same ELISA assay procedure as described in Example 1. The results of this may be seen in Table 2 below:

TABLE 2

| Sample | ORF2 in supernatant (μg) |
|---|---|
| 1 | 78.71 |
| 2 | 68.75 |
| 3 | 83.33 |

This example demonstrates that neutralization with BEI does not remove or degrade significant amounts of the recombinant PCV2 ORF2 protein product. This is evidenced by the fact that there is no large loss of ORF2 in the supernatant from the BEI or elevated temperatures. Those of skill in the art will recognize that the recovered ORF2 is a stable protein product.

EXAMPLE 3

This example demonstrates that the present invention is scalable from small scale production of recombinant PCV2 ORF2 to large scale production of recombinant PCV2 ORF2. $5.0\times10^5$ cells/ml of SF+ cells/ml in 7000 mL of ExCell 420 media was planted in a 20000 mL Applikon Bioreactor. The media and cells were then incubated at 27° C. and agitated at 100 RPM for the next 68 hours. At the $68^{th}$ hour, 41.3 mL of PCV2 ORF2 Baculovirus MSV+3 was added to 700 mL of ExCell 420 medium. The resultant mixture was then added to the bioreactor. For the next seven days, the mixture was incubated at 27° C. and agitated at 100 RPM. Samples from the bioreactor were extracted every 24 hours beginning at day 4, post-infection, and each sample was centrifuged. The supernatant of the samples were preserved and the amount of ORF2 was then quantified using SDS-PAGE densitometry. The results of this can be seen in Table 3 below:

TABLE 3

| Day after infection: | ORF2 in supernatant (μg/mL) |
|---|---|
| 4 | 29.33 |
| 5 | 41.33 |
| 6 | 31.33 |
| 7 | 60.67 |

EXAMPLE 4

This example tests the efficacy of seven PCV2 candidate vaccines and further defines efficacy parameters following exposure to a virulent strain of PCV2. One hundred and eight (108) cesarean derived colostrum deprived (CDCD) piglets, 9-14 days of age, were randomly divided into 9 groups of equal size. Table 4 sets forth the General Study Design for this Example.

TABLE 4

General Study Design

| Group | No. Of Pigs | Treatment | Day of Treatment | KLH/ICFA on Day 21 and Day 27 | Challenged with Virulent PCV2 on Day 24 | Necropsy on Day 49 |
|---|---|---|---|---|---|---|
| 1 | 12 | PCV2 Vaccine No. 1 - (vORF2 16 µg) | 0 | + | + | + |
| 2 | 12 | PCV2 Vaccine No. 2 - (vORF2 8 µg) | 0 | + | + | + |
| 3 | 12 | PCV2 Vaccine No. 3 - (vORF2 4 µg) | 0 | + | + | + |
| 4 | 12 | PCV2 Vaccine No. 4 - (rORF2 16 µg) | 0 | + | + | + |
| 5 | 12 | PCV2 Vaccine No. 5 - (rORF2 8 µg) | 0 | + | + | + |
| 6 | 12 | PCV2 Vaccine No. 6 - (rORF2 4 µg) | 0 | + | + | + |
| 7 | 12 | PCV2 Vaccine No. 7 - (Killed whole cell virus) | 0 | + | + | + |
| 8 | 12 | None - Challenge Controls | N/A | + | + | + |
| 9 | 12 | None - Strict Negative Control Group | N/A | + | − | + | vORF2 = isolated viral ORF2;
rORF2 = recombinant baculovirus expressed ORF2;
killed whole cell virus = PCV2 virus grown in suitable cell culture Seven of the groups (Groups 1-7) received doses of PCV2 ORF2 polypeptide, one of the groups acted as a challenge control and received no PCV2 ORF2, and another group acted as the strict negative control group and also received no PCV2 ORF2. On Day 0, Groups 1 through 7 were treated with assigned vaccines. Piglets in Group 7 were given a booster treatment on Day 14. Piglets were observed for adverse events and injection site reactions following vaccination and on Day 19, piglets were moved to the second study site. At the second study site, Groups 1-8 were group housed in one building while Group 9 was housed in a separate building. All pigs received keyhole limpet hemocyanin (KLH)/incomplete Freund's adjuvant (ICFA) on Days 21 and 27 and on Day 24, Groups 1-8 were challenged with a virulent PCV2.

Pre- and post-challenge, blood samples were collected for PCV2 serology. Post-challenge, body weight data for determination of average daily weight gain (ADWG), and clinical symptoms, as well as nasal swab samples to determine nasal shedding of PCV2, were collected. On Day 49, all surviving pigs were necropsied, lungs were scored for lesions, and selected tissues were preserved in formalin for Immunohistochemistry (IHC) testing at a later date.

Materials and Methods

This was a partially blinded vaccination-challenge feasibility study conducted in CDCD pigs, 9 to 14 days of age on Day 0. To be included in the study, PCV2 IFA titers of sows were ≦1:1000. Additionally, the serologic status of sows were from a known PRRS-negative herd. Twenty-eight (28) sows were tested for PCV2 serological status. Fourteen (14) sows had a PCV2 titer of ≦1000 and were transferred to the first study site. One hundred ten (110) piglets were delivered by cesarean section surgeries and were available for this study on Day −4. On Day −3, 108 CDCD pigs at the first study site were weighed, identified with ear tags, blocked by weight and randomly assigned to 1 of 9 groups, as set forth above in table 4. If any test animal meeting the inclusion criteria was enrolled in the study and was later excluded for any reason, the Investigator and Monitor consulted in order to determine the use of data collected from the animal in the final analysis. The date of which enrolled piglets were excluded and the reason for exclusion was documented. Initially, no sows were excluded. A total of 108 of an available 110 pigs were randomly assigned to one of 9 groups on Day −3. The two smallest pigs (No. 17 and 19) were not assigned to a group and were available as extras, if needed. During the course of the study, several animals were removed. Pig 82 (Group 9) on Day −1, Pig No. 56 (Group 6) on Day 3, Pig No. 53 (Group 9) on Day 4, Pig No. 28 (Group 8) on Day 8, Pig No. 69 (Group 8) on Day 7, and Pig No. 93 (Group 4) on Day 9, were each found dead prior to challenge. These six pigs were not included in the final study results. Pig no 17 (one of the extra pigs) was assigned to Group 9. The remaining extra pig, No. 19, was excluded from the study.

The formulations given to each of the groups were as follows: Group 1 was designed to administer 1 ml of viral ORF2 (vORF2) containing 16 µg ORF2/ml. This was done by mixing 10.24 ml of viral ORF2 (256 µg/25 µg/ml=10.24 ml vORF2) with 3.2 ml of 0.5% Carbopol and 2.56 ml of phosphate buffered saline at a pH of 7.4. This produced 16 ml of formulation for group 1. Group 2 was designed to administer 1 ml of vORF2 containing 8 µg vORF2/ml. This was done by mixing 5.12 ml of vORF2 (128 µg/25 µg/ml=5.12 ml vORF2) with 3.2 ml of 0.5% Carbopol and 7.68 ml of phosphate buffered saline at a pH of 7.4. This produced 16 ml of formulation for group 2. Group 3 was designed to administer 1 ml of vORF2 containing 4 µg vORF2/ml. This was done by mixing 2.56 ml of vORF2 (64 µg/25 µg/ml=2.56 ml vORF2) with 3.2 ml of 0.5% Carbopol and 10.24 ml of phosphate buffered saline at a pH of 7.4. This produced 16 ml of formulation for group 3. Group 4 was designed to administer 1 ml of recombinant ORF2 (rORF2) containing 16 µg rORF2/ml. This was done by mixing 2.23 ml of rORF2 (512 µg/230 µg/ml=2.23 ml rORF2) with 6.4 ml of 0.5% Carbopol and 23.37 ml of phosphate buffered saline at a pH of 7.4. This produced 32 ml of formulation for group 4. Group 5 was designed to administer 1 ml of rORF2 containing 8 µg rORF2/ml. This was done by mixing 1.11 ml of rORF2 (256 µg/230 µg/ml=1.11 ml rORF2) with 6.4 ml of 0.5% Carbopol and 24.49 ml of phosphate buffered saline at a pH of 7.4. This produced 32 ml of formulation for group 5. Group 6 was designed to administer 1 ml of rORF2 containing 8 µg rORF2/ml. This was done by mixing 0.56 ml of rORF2 (128 µg/230 µg/ml=0.56 ml rORF2) with 6.4 ml of 0.5% Carbopol and 25.04 ml of phosphate buffered saline at a pH of 7.4. This produced 32 ml of formulation for group 6. Group 7 was designed to administer 2 ml of PCV2 whole killed cell vaccine (PCV2 KV) containing the MAX PCV2 KV. This was done by mixing 56 ml of PCV2 KV with 14 ml of 0.5% Carbopol. This produced 70 ml of formulation for group 7. Finally group 8 was designed to administer KLH at 0.5 µg/ml or 1.0 µg/ml per 2 ml dose. This was done by mixing 40.71 ml KLH (7.0 µg protein/ml at 0.5 µg/ml=570 ml (7.0 µg/ml)(x)=(0.5)(570 ml)), 244.29 ml phosphate buffered saline at a pH of 7.4, and 285 ml Freunds adjuvant. Table 5 describes the time frames for the key activities of this Example.

TABLE 5

Study Activities

| Study Day | Study Activity |
|---|---|
| −4, 0 to 49 | General observations for overall health and clinical symptoms |
| −3 | Weighed; Randomized to groups; Collected blood samples from all pigs |
| 0 | Health examination; Administered IVP Nos. 1-7 to Groups 1-7, respectively |
| 0-7 | Observed pigs for injection site reactions |
| 14 | Boostered Group 7 with PCV2 Vaccine No. 7; Blood samples from all pigs |
| 14-21 | Observed Group 7 for injection site reactions |
| 16-19 | Treated all pigs with antibiotics (data missing) |
| 19 | Pigs transported from the first test site to a second test site |
| 21 | Treated Groups 1-9 with KLH/ICFA |
| 24 | Collected blood and nasal swab samples from all pigs; Weighed all pigs; Challenged Groups 1-8 with PCV2 challenge material |
| 25, 27, 29, 31, 33, 35, 37, 39, 41, 43, 45, 47 | Collected nasal swab samples from all pigs |
| 27 | Treated Groups 1-9 with KLH/ICFA |
| 31 | Collected blood samples from all pigs |
| 49 | Collected blood and nasal swab samples from all pigs; Weighed all pigs; Necropsy all pigs; Gross lesions noted with emphasis placed on icterus and gastric ulcers; Lungs evaluated for lesions; Fresh and formalin fixed tissue samples saved; In-life phase of the study completed |

Following completion of the in-life phase of the study, formalin fixed tissues were examined by Immunohistochemistry (IHC) for detection of PCV2 antigen by a pathologist, blood samples were evaluated for PCV2 serology, nasal swab samples were evaluated for PCV2 shedding, and average daily weight gain (ADWG) was determined from Day 24 to Day 49.

Animals were housed at the first study site in individual cages in five rooms from birth to approximately 11 days of age (approximately Day 0 of the study). Each room was identical in layout and consisted of stacked individual stainless steel cages with heated and filtered air supplied separately to each isolation unit. Each room had separate heat and ventilation, thereby preventing cross-contamination of air between rooms. Animals were housed in two different buildings at the second study site. Group 9 (The Strict negative control group) was housed separately in a converted finisher building and Groups 1-8 were housed in converted nursery building. Each group was housed in a separate pen (11-12 pigs per pen) and each pen provided approximately 3.0 square feet per pig. Each pen was on an elevated deck with plastic slatted floors. A pit below the pens served as a holding tank for excrement and waste. Each building had its own separate heating and ventilation systems, with little likelihood of cross-contamination of air between buildings.

At the first study site, piglets were fed a specially formulated milk ration from birth to approximately 3 weeks of age. All piglets were consuming solid, special mixed ration by Day 19 (approximately 4½ weeks of age). At the second study site, all piglets were fed a custom non-medicated commercial mix ration appropriate for their age and weight, ad libitum. Water at both study sites was also available ad libitum.

All test pigs were treated with Vitamin E on Day −2, with iron injections on Day −1 and with NAXCEL® (1.0 mL, 1M, in alternating hams) on Days 16, 17, 18 and 19. In addition, Pig No. 52 (Group 9) was treated with an iron injection on Day 3, Pig 45 (Group 6) was treated with an iron injection on Day 11, Pig No. 69 (Group 8) was treated with NAXCEL® on Day 6, Pig No. 74 (Group 3) was treated with dexamethazone and penicillin on Day 14, and Pig No. 51 (Group 1) was treated with dexamethazone and penicillin on Day 13 and with NAXCEL® on Day 14 for various health reasons.

While at both study sites, pigs were under veterinary care. Animal health examinations were conducted on Day 0 and were recorded on the Health Examination Record Form. All animals were in good health and nutritional status before vaccination as determined by observation on Day 0. All test animals were observed to be in good health and nutritional status prior to challenge. Carcasses and tissues were disposed of by rendering. Final disposition of study animals was records on the Animal Disposition Record.

On Day 0, pigs assigned to Groups 1-6 received 1.0 mL of PCV2 Vaccines 1-6, respectively, IM in the left neck region using a sterile 3.0 mL Luer-lock syringe and a sterile 20 g×½" needle. Pigs assigned to Group 7 received 2.0 mL of PCV2 Vaccine No. 7 IM in the left neck region using a sterile 3.0 mL Luer-lock syringe and a sterile 20 g×½" needle. On Day 14, pigs assigned to Group 7 received 2.0 mL of PCV2 Vaccine No. 7 IM in the right neck region using a sterile 3.0 mL Luer-lock syringe and a sterile 20 g×½" needle.

On Day 21 all test pigs received 2.0 mL of KLH/ICFA IM in the right ham region using a sterile 3.0 mL Luer-lock syringe and a sterile 20 g×1" needle. On Day 27 all test pigs received 2.0 mL of KLH/ICFA in the left ham region using a sterile 3.0 mL Luer-lock syringe and a sterile 20 g×1" needle.

On Day 24, pigs assigned to Groups 1-8 received 1.0 mL of PCV2 ISUVDL challenge material (5.11 $\log_{10}$ $TCID_{50}$/mL) IM in the left neck region using a sterile 3.0 mL Luer-lock syringe and a sterile 20 g×1" needle. An additional 1.0 mL of the same material was administered IN to each pig (0.5 mL per nostril) using a sterile 3.0 mL Luer-lock syringe and nasal canula.

Test pigs were observed daily for overall health and adverse events on Day −4 and from Day 0 to Day 19. Observations were recorded on the Clinical Observation Record. All test pigs were observed from Day 0 to Day 7, and Group 7 was further observed from Day 14 to 21, for injection site reactions. Average daily weight gain was determined by weighing each pig on a calibrated scale on Days −3, 24 and 49, or on the day that a pig was found dead after challenge. Body weights were recorded on the Body Weight Form. Day −3 body weights were utilized to block pigs prior to randomization. Day 24 and Day 49 weight data was utilized to determine the average daily weight gain (ADWG) for each pig during these time points. For pigs that died after challenge and before Day 49, the ADWG was adjusted to represent the ADWG from Day 24 to the day of death.

In order to determine PCV2 serology, venous whole blood was collected from each piglet from the orbital venous sinus on Days −3 and 14. For each piglet, blood was collected from the orbital venous sinus by inserting a sterile capillary tube into the medial canthus of one of the eyes and draining approximately 3.0 mL of whole blood into a 4.0 mL Serum Separator Tube (SST). On Days 24, 31, and 49, venous whole blood from each pig was collected from the anterior vena cava using a sterile 18 g×1½" Vacutainer needle (Becton Dickinson and Company, Franklin Lakes, N.J.), a Vacutainer needle holder and a 13 mL SST. Blood collections at each time point were recorded on the Sample Collection Record. Blood in each SST was allowed to clot, each SST was then spun down and the serum harvested. Harvested serum was transferred to a sterile snap tube and stored at −70±10° C. until tested at a later date. Serum samples were tested for the presence of PCV2 antibodies by BIVI-R&D personnel.

Pigs were observed once daily from Day 20 to Day 49 for clinical symptoms and clinical observations were recorded on the Clinical Observation Record.

To test for PCV2 nasal shedding, on Days 24, 25, and then every other odd numbered study day up to and including Day 49, a sterile dacron swab was inserted intra nasally into either the left or right nostril of each pig (one swab per pig) as aseptically as possible, swished around for a few seconds and then removed. Each swab was then placed into a single sterile snap-cap tube containing 1.0 mL of EMEM media with 2% IFBS, 500 units/mL of Penicillin, 500 µg/mL of Streptomycin and 2.5 µg/mL of Fungizone. The swab was broken off in the tube, and the snap tube was sealed and appropriately labeled with animal number, study number, date of collection, study day and "nasal swab." Sealed snap tubes were stored at −40±10° C. until transported overnight on ice to BIVI-St. Joseph. Nasal swab collections were recorded on the Nasal Swab Sample Collection Form. BIVI-R&D conducted quantitative virus isolation (VI) testing for PCV2 on nasal swab samples. The results were expressed in $\log_{10}$ values. A value of 1.3 logs or less was considered negative and any value greater than 1.3 logs was considered positive.

Pigs that died (Nos. 28, 52, 56, 69, 82, and 93) at the first study site were necropsied to the level necessary to determine a diagnosis. Gross lesions were recorded and no tissues were retained from these pigs. At the second study site, pigs that died prior to Day 49 (Nos. 45, 23, 58, 35), pigs found dead on Day 49 prior to euthanasia (Nos. 2, 43) and pigs euthanized on Day 49 were necropsied. Any gross lesions were noted and the percentages of lung lobes with lesions were recorded on the Necropsy Report Form.

From each of the 103 pigs necropsied at the second study site, a tissue sample of tonsil, lung, heart, liver, mesenteric lymph node, kidney and inguinal lymph node was placed into a single container with buffered 10% formalin; while another tissue sample from the same aforementioned organs was placed into a Whirl-pak (M-Tech Diagnostics Ltd., Thelwall, UK) and each Whirl-pak was placed on ice. Each container was properly labeled. Sample collections were recorded on the Necropsy Report Form. Afterwards, formalin-fixed tissue samples and a Diagnostic Request Form were submitted for IHC testing. IHC testing was conducted in accordance with standard ISU laboratory procedures for receiving samples, sample and slide preparation, and staining techniques. Fresh tissues in Whirl-paks were shipped with ice packs to the Study Monitor for storage (−70°±10° C.) and possible future use. Formalin-fixed tissues were examined by a pathologist for detection of PCV2 by IHC and scored using the following scoring system: 0=None; 1=Scant positive staining, few sites; 2=Moderate positive staining, multiple sites; and 3=Abundant positive staining, diffuse throughout the tissue. Due to the fact that the pathologist could not positively differentiate inguinal LN from mesenteric LN, results for these tissues were simply labeled as Lymph Node and the score given the highest score for each of the two tissues per animal.

Results

Results for this example are given below. It is noted that one pig from Group 9 died before Day 0, and 5 more pigs died post-vaccination (1 pig from Group 4; 1 pig from Group 6; 2 pigs from Group 8; and 1 pig from Group 9). Post-mortem examination indicated all six died due to underlying infections that were not associated with vaccination or PMWS. Additionally, no adverse events or injection site reactions were noted with any groups.

Average daily weight gain (ADWG) results are presented below in Table 6. Group 9, the strict negative control group, had the highest ADWG (1.06±0.17 lbs/day), followed by Group 5 (0.94±0.22 lbs/day), which received one dose of 8 µg of rORF2. Group 3, which received one dose of 4 µg of vORF2, had the lowest ADWG (0.49±0.21 lbs/day), followed by Group 7 (0.50±0.15 lbs/day), which received 2 doses of killed vaccine.

TABLE 6

Summary of Group Average Daily Weight Gain (ADWG)

| Group | Treatment | N | ADWG - lbs/day (Day 24 to Day 49) or adjusted for pigs dead before Day 29 |
|---|---|---|---|
| 1 | vORF2 - 16 µg (1 dose) | 12 | 0.87 ± 0.29 lbs/day |
| 2 | vORF2 - 8 µg (1 dose) | 12 | 0.70 ± 0.32 lbs/day |
| 3 | vORF2 - 4 µg (1 dose) | 12 | 0.49 ± 0.21 lbs/day |
| 4 | rORF2 - 16 µg (1 dose) | 11 | 0.84 ± 0.30 lbs/day |
| 5 | rORF2 - 8 µg (1 dose) | 12 | 0.94 ± 0.22 lbs/day |
| 6 | rORF2 - 4 µg (1 dose) | 11 | 0.72 ± 0.25 lbs/day |
| 7 | KV (2 doses) | 12 | 0.50 ± 0.15 lbs/day |
| 8 | Challenge Controls | 10 | 0.76 ± 0.19 lbs/day |
| 9 | Strict Negative Controls | 11 | 1.06 ± 0.17 lbs/day | vORF2 = isolated viral ORF2;
rORF2 = recombinant baculovirus expressed ORF2;
killed whole cell virus = PCV2 virus grown in suitable cell culture PCV2 serology results are presented below in Table 7. All nine groups were seronegative for PCV2 on Day −3. On Day 14, Groups receiving vORF2 vaccines had the highest titers, which ranged from 187.5 to 529.2. Pigs receiving killed viral vaccine had the next highest titers, followed by the groups receiving rORF2 vaccines. Groups 8 and 9 remained seronegative at this time. On Day 24 and Day 31, pigs receiving vORF2 vaccines continued to demonstrate a strong serological response, followed closely by the group that received two doses of a killed viral vaccine. Pigs receiving rORF2 vaccines were slower to respond serologically and Groups 8 and 9 continued to remain seronegative. On Day 49, pigs receiving vORF2 vaccine, 2 doses of the killed viral vaccine and the lowest dose of rORF2 demonstrated the strongest serological responses. Pigs receiving 16 µg and 8 µg of rORF2 vaccines had slightly higher IFA titers than challenge controls. Group 9 on Day 49 demonstrated a strong serological response.

TABLE 7

Summary of Group PCV2 IFA Titers
AVERAGE IFA TITER

| Group | Treatment | Day −3 | Day 14 | Day 24 | Day 31** | Day 49*** |
|---|---|---|---|---|---|---|
| 1 | vORF2 - 16 μg (1 dose) | 50.0 | 529.2 | 4400.0 | 7866.7 | 11054.5 |
| 2 | vORF2 - 8 μg (1 dose) | 50.0 | 500.0 | 3466.7 | 6800.0 | 10181.8 |
| 3 | vORF2 - 4 μg (1 dose) | 50.0 | 187.5 | 1133.3 | 5733.3 | 9333.3 |
| 4 | rORF2 - 16 μg (1 dose) | 50.0 | 95.5 | 1550.0 | 3090.9 | 8000.0 |
| 5 | rORF2 - 8 μg (1 dose) | 50.0 | 75.0 | 887.5 | 2266.7 | 7416.7 |
| 6 | rORF2 - 4 μg (1 dose) | 50.0 | 50.0 | 550.0 | 3118.2 | 10570.0 |
| 7 | KV (2 doses) | 50.0 | 204.2 | 3087.5 | 4620.8 | 8680.0 |
| 8 | Challenge Controls | 50.0 | 55.0 | 50.0 | 50.0 | 5433.3 |
| 9 | Strict Negative Controls | 50.0 | 59.1 | 59.1 | 54.5 | 6136.4 | vORF2 = isolated viral ORF2;
rORF2 = recombinant baculovirus expressed ORF2;
killed whole cell virus = PCV2 virus grown in suitable cell culture
*For calculation purposes, a ≦ 100 IFA titer was designated as a titer of "50"; a ≧ 6400 IFA titer was designated as a titer of "12,800".
**Day of Challenge
***Day of Necropsy The results from the post-challenge clinical observations are presented below in Table 8. This summary of results includes observations for Abnormal Behavior, Abnormal Respiration, Cough and Diarrhea. Table 9 includes the results from the Summary of Group Overall Incidence of Clinical Symptoms and Table 10 includes results from the Summary of Group Mortality Rates Post-challenge. The most common clinical symptom noted in this study was abnormal behavior, which was scored as mild to severe lethargy. Pigs receiving the 2 lower doses of vORF2, pigs receiving 16 μg of rORF2 and pigs receiving 2 doses of KV vaccine had incidence rates of ≧27.3%. Pigs receiving 8 μg of rORF2 and the strict negative control group had no abnormal behavior. None of the pigs in this study demonstrated any abnormal respiration. Coughing was noted frequently in all groups (0 to 25%), as was diarrhea (0-20%). None of the clinical symptoms noted were pathognomic for PMWS.

The overall incidence of clinical symptoms varied between groups. Groups receiving any of the vORF2 vaccines, the group receiving 16 μg of rORF2, the group receiving 2 doses of KV vaccine and the challenge control group had the highest incidence of overall clinical symptoms (≧36.4%). The strict negative control group, the group receiving 8 μg of rORF2 and the group receiving 4 μg of rORF2 had overall incidence rates of clinical symptoms of 0%, 8.3% and 9.1%, respectively.

Overall mortality rates between groups varied as well. The group receiving 2 doses of KV vaccine had the highest mortality rate (16.7%); while groups that received 4 μg of vORF2, 16 μg of rORF2, or 8 μg of rORF2 and the strict negative control group all had 0% mortality rates.

TABLE 8

Summary of Group Observations for Abnormal Behavior, Abnormal Respiration, Cough, and Diarrhea

| Group | Treatment | N | Abnormal Behavior[1] | Abnormal Behavior[2] | Cough[3] | Diarrhea[4] |
|---|---|---|---|---|---|---|
| 1 | vORF2 - 16 μg (1 dose) | 12 | 2/12 (16.7%) | 0/12 (0%) | 3/12 (25%) | 2/12 (16/7%) |
| 2 | vORF2 - 8 μg (1 dose) | 12 | 4/12 (33.3%) | 0/12 (0%) | 1/12 (8.3%) | 1/12 (8.3%) |
| 3 | vORF2 - 4 μg (1 dose) | 12 | 8/12 (66.7%) | 0/12 (0%) | 2/12 (16.7%) | 1/12 (8.3%) |
| 4 | rORF2 - 16 μg (1 dose) | 11 | 3/11 (27.3%) | 0/11 (0%) | 0/11 (0%) | 2/11 (18.2%) |
| 5 | rORF2 - 8 μg (1 dose) | 12 | 0/12 (0%) | 0/12 (0%) | 1/12 (8.3%) | 0/12 (0%) |
| 6 | rORF2 - 4 μg (1 dose) | 11 | 1/11 (9.1%) | 0/11 (0%) | 0/11 (0%) | 0/12 (0%) |
| 7 | KV (2 doses) | 12 | 7/12 (58.3) | 0/12 (0%) | 0/12 (0%) | 1/12 (8.3%) |
| 8 | Challenge Controls | 10 | 1/10 (10%) | 0/10 (0%) | 2/10 (20%) | 2/10 (20%) |
| 9 | Strict Negative Controls | 11 | 0/11 (0%) | 0/11 (0%) | 0/11 (0%) | 0/11 (0%) | vORF2 = isolated viral ORF2;
rORF2 = recombinant baculovirus expressed ORF2;
killed whole cell virus = PCV2 virus grown in suitable cell culture
[1] Total number of pigs in each group that demonstrated any abnormal behavior for at least one day
[2] Total number of pigs in each group that demonstrated any abnormal respiration for at least one day
[3] Total number of pigs in each group that demonstrated a cough for at least one day
[4] Total number of pigs in each group that demonstrated diarrhea for at least one day

TABLE 9

Summary of Group Overall Incidence of Clinical Symptoms

| Group | Treatment | N | Incidence of pigs with Clinical Symptoms[1] | Incidence Rate |
|---|---|---|---|---|
| 1 | vORF2 - 16 µg (1 dose) | 12 | 5 | 41.7% |
| 2 | vORF2 - 8 µg (1 dose) | 12 | 5 | 41.7% |
| 3 | vORF2 - 4 µg (1 dose) | 12 | 8 | 66.7% |
| 4 | rORF2 - 16 µg (1 dose) | 11 | 4 | 36.4% |
| 5 | rORF2 - 8 µg (1 dose) | 12 | 1 | 8.3% |
| 6 | rORF2 - 4 µg (1 dose) | 11 | 1 | 9.1% |
| 7 | KV (2 doses) | 12 | 7 | 58.3% |
| 8 | Challenge Controls | 10 | 4 | 40% |
| 9 | Strict Negative Controls | 11 | 0 | 0% | vORF2 = isolated viral ORF2;
rORF2 = recombinant baculovirus expressed ORF2;
killed whole cell virus = PCV2 virus grown in suitable cell culture
[1]Total number of pigs in each group that demonstrated any clinical symptom for at least one day

TABLE 10

Summary of Group Mortality Rates Post-challenge

| Group | Treatment | N | Dead Post-challenge | Mortality Rate |
|---|---|---|---|---|
| 1 | vORF2 - 16 µg (1 dose) | 12 | 1 | 8.3% |
| 2 | vORF2 - 8 µg (1 dose) | 12 | 1 | 8.3% |
| 3 | vORF2 - 4 µg (1 dose) | 12 | 0 | 0% |
| 4 | rORF2 - 16 µg (1 dose) | 11 | 0 | 0% |
| 5 | rORF2 - 8 µg (1 dose) | 12 | 0 | 0% |
| 6 | rORF2 - 4 µg (1 dose) | 11 | 1 | 9.1% |
| 7 | KV (2 doses) | 12 | 2 | 16.7% |
| 8 | Challenge Controls | 10 | 1 | 10% |
| 9 | Strict Negative Controls | 11 | 0 | 0% | vORF2 = isolated viral ORF2;
rORF2 = recombinant baculovirus expressed ORF2;
killed whole cell virus = PCV2 virus grown in suitable cell culture PCV2 nasal shedding results are presented below in Table 11. Following challenge on Day 24, 1 pig in Group 7 began shedding PCV2 on Day 27. None of the other groups experienced shedding until Day 33. The bulk of nasal shedding was noted from Day 35 to Day 45. Groups receiving any of the three vORF2 vaccines and groups receiving either 4 or 8 µg of rORF2 had the lowest incidence of nasal shedding of PCV2 ($\leq 9.1\%$). The challenge control group (Group 8) had the highest shedding rate (80%), followed by the strict negative control group (Group 9), which had an incidence rate of 63.6%.

TABLE 11

Summary of Group Incidence of Nasal Shedding of PCV2

| Group | Treatment | N | No. Of pigs that shed for at least one day | Incidence Rate |
|---|---|---|---|---|
| 1 | vORF2 - 16 µg (1 dose) | 12 | 1 | 8.3% |
| 2 | vORF2 - 8 µg (1 dose) | 12 | 1 | 8.3% |
| 3 | vORF2 - 4 µg (1 dose) | 12 | 1 | 8.3% |
| 4 | rORF2 - 16 µg (1 dose) | 11 | 2 | 18.2% |
| 5 | rORF2 - 8 µg (1 dose) | 12 | 1 | 8.3% |
| 6 | rORF2 - 4 µg (1 dose) | 11 | 1 | 9.1% |
| 7 | KV (2 doses) | 12 | 5 | 41.7% |
| 8 | Challenge Controls | 10 | 8 | 80% |
| 9 | Strict Negative Controls | 11 | 7 | 63.6% | vORF2 = isolated viral ORF2;
rORF2 = recombinant baculovirus expressed ORF2;
killed whole cell virus = PCV2 virus grown in suitable cell culture The Summary of Group Incidence of Icterus, Group Incidence of Gastric Ulcers, Group Mean Lung Lesion Scores, and Group Incidence of Lung Lesions are shown below in Table 12. Six pigs died at the first test site during the post-vaccination phase of the study (Group 4, N=1; Group 6, N=1; Group 8, N=2; Group 9, N=2). Four out of six pigs had fibrinous lesions in one or more body cavities, one pig (Group 6) had lesions consistent with clostridial disease, and one pig (Group 9) had no gross lesions. None of the pigs that died during the post-vaccination phased of the study had lesions consistent with PMWS.

Pigs that died post-challenge and pigs euthanized on Day 49 were necropsied. At necropsy, icterus and gastric ulcers were not present in any group. With regard to mean % lung lesions, Group 9 had lowest mean % lung lesions (0%), followed by Group 1 with 0.40±0.50% and Group 5 with 0.68±1.15%. Groups 2, 3, 7 and 8 had the highest mean % lung lesions ($\geq 7.27\%$). Each of these four groups contained one pig with % lung lesions $\geq 71.5\%$, which skewed the results higher for these four groups. With the exception of Group 9 with 0% lung lesions noted, the remaining 8 groups had $\leq 36\%$ lung lesions. Almost all lung lesions noted were described as red/purple and consolidated.

TABLE 12

Summary of Group Incidence of Icterus, Group Incidence of Gastric Ulcers, Group Mean % Lung Lesion Scores, and Group Incidence of Lung Lesions Noted

| Group | Treatment | Icterus | Gastric Ulcers | Mean % Lung Lesions | Incidence of Lung Lesions Noted |
|---|---|---|---|---|---|
| 1 | vORF2 - 16 µg (1 dose) | 0/12 (0%) | 0/12 (0%) | 0.40 ± 0.50% | 10/12 (83%) |
| 2 | vORF2 - 8 µg (1 dose) | 0/12 (0%) | 0/12 (0%) | 7.41 ± 20.2% | 10/12 (83%) |
| 3 | vORF2 - 4 µg (1 dose) | 0/12 (0%) | 0/12 (0%) | 9.20 ± 20.9% | 10/12 (83%) |
| 4 | rORF2 - 16 µg (1 dose) | 0/11 (0%) | 0/11 (0%) | 1.5 ± 4.74% | 4/11 (36%) |
| 5 | rORF2 - 8 µg (1 dose) | 0/12 (0%) | 0/12 (0%) | 0.68 ± 1.15% | 9/12 (75%) |
| 6 | rORF2 - 4 µg (1 dose) | 0/11 (0%) | 0/11 (0%) | 2.95 ± 5.12% | 7/11 (64%) |
| 7 | KV (2 doses) | 0/12 (0%) | 0/12 (0%) | 7.27 ± 22.9% | 9/12 (75%) |
| 8 | Challenge Controls | 0/10 (0%) | 0/10 (0%) | 9.88 ± 29.2% | 8/10 (80%) |

TABLE 12-continued

Summary of Group Incidence of Icterus, Group Incidence of Gastric Ulcers, Group Mean % Lung Lesion Scores, and Group Incidence of Lung Lesions Noted

| Group | Treatment | Icterus | Gastric Ulcers | Mean % Lung Lesions | Incidence of Lung Lesions Noted |
|---|---|---|---|---|---|
| 9 | Strict Negative Controls | 0/11 (0%) | 0/11 (0%) | 0/11 (0%) | 0/11 (0%) | vORF2 = isolated viral ORF2;
rORF2 = recombinant baculovirus expressed ORF2;
KV or killed whole cell virus = PCV2 virus grown in suitable cell culture The Summary of Group IHC Positive Incidence Results are shown in Table 13. Group 1 (vORF2-16 µg) and Group 5 (rORF2-8 µg) had the lowest rate of IHC positive results (16.7%). Group 8 (Challenge Controls) and Group 9 (Strict Negative Controls) had the highest rate of IHC positive results, 90% and 90.9%, respectively.

TABLE 13

Summary of Group IHC Positive Incidence Rate

| Group | positive Treatment | N | No. Of pigs that had at least one tissue for PCV2 | Incidence Rate |
|---|---|---|---|---|
| 1 | vORF2 - 16 µg (1 dose) | 12 | 2 | 16.7% |
| 2 | vORF2 - 8 µg (1 dose) | 12 | 3 | 25.0% |
| 3 | vORF2 - 4 µg (1 dose) | 12 | 8 | 66.7% |
| 4 | rORF2 - 16 µg (1 dose) | 11 | 4 | 36.3% |
| 5 | rORF2 - 8 µg (1 dose) | 12 | 2 | 16.7% |
| 6 | rORF2 - 4 µg (1 dose) | 11 | 4 | 36.4% |
| 7 | KV (2 doses) | 12 | 5 | 41.7% |
| 8 | Challenge Controls | 10 | 9 | 90.0% |
| 9 | Strict Negative Controls | 11 | 10 | 90.9% | vORF2 = isolated viral ORF2;
rORF2 = recombinant baculovirus expressed ORF2;
KV or killed whole cell virus = PCV2 virus grown in suitable cell culture Post-challenge, Group 5, which received one dose of 8 µg of rORF2 antigen, outperformed the other 6 vaccine groups. Group 5 had the highest ADWG (0.94±0.22 lbs/day), the lowest incidence of abnormal behavior (0%), the second lowest incidence of cough (8.3%), the lowest incidence of overall clinical symptoms (8.3%), the lowest mortality rate (0%), the lowest rate of nasal shedding of PCV2 (8.3%), the second lowest rate for mean % lung lesions (0.68±1.15%) and the lowest incidence rate for positive tissues (16.7%). Groups receiving various levels of rORF2 antigen overall outperformed groups receiving various levels of vORF2 and the group receiving 2 doses of killed whole cell PCV2 vaccine performed the worst. Tables 14 and 15 contain summaries of group post-challenge data.

TABLE 14

Summary of Group Post-Challenge Data - Part 1

| Group | N | Treatment | ADWG (lbs/day) | Abnormal Behavior | Cough | Overall Incidence of Clinical Symptoms |
|---|---|---|---|---|---|---|
| 1 | 12 | vORF2 - 16 µg (1 dose) | 0.87 ± 0.29 | 2/12 (16.7%) | 3/12 (25%) | 41.7% |
| 2 | 12 | vORF2 - 8 µg (1 dose) | 0.70 ± 0.32 | 4/12 (33.3%) | 1/12 (8.3%) | 41.7% |
| 3 | 12 | vORF2 - 4 µg (1 dose) | 0.49 ± 0.21 | 8/12 (66.7%) | 2/12 (16.7%) | 66.7% |
| 4 | 11 | rORF2 - 16 µg (1 dose) | 0.84 ± 0.30 | 3/11 (27.3%) | 0/11 (0%) | 36.4% |
| 5 | 12 | rORF2 - 8 µg (1 dose) | 0.94 ± 0.22 | 0/12 (0%) | 1/12 (8.3%) | 8.3% |
| 6 | 11 | rORF2 - 4 µg (1 dose) | 0.72 ± 0.25 | 1/11 (9.1%) | 0/11 (0%) | 9.1% |
| 7 | 12 | KV (2 doses) | 0.50 ± 0.15 | 7/12 (58.3) | 0/12 (0%) | 58.3% |
| 8 | 10 | Challenge Controls | 0.76 ± 0.19 | 1/10 (10%) | 2/10 (20%) | 40% |
| 9 | 11 | Strict Negative Controls | 1.06 ± 0.17 | 0/11 (0%) | 0/11 (0%) | 0% | vORF2 = isolated viral ORF2;
rORF2 = recombinant baculovirus expressed ORF2;
KV or killed whole cell virus = PCV2 virus grown in suitable cell culture

TABLE 15

Summary of Group Post-Challenge Data - Part 2

| Group | N | Treatment | Mortality Rate | Nasal Shedding | Mean % Lung Lesions | Incidence Rate of at least one tissue IHC positive for PCV2 |
|---|---|---|---|---|---|---|
| 1 | 12 | vORF2 - 16 μg (1 dose) | 8.3% | 8.3% | 0.40 ± 0.50% | 16.7% |
| 2 | 12 | vORF2 - 8 μg (1 dose) | 8.3% | 8.3% | 7.41 ± 20.2% | 25.0% |
| 3 | 12 | vORF2 - 4 μg (1 dose) | 0% | 8.3% | 9.20 ± 20.9% | 66.7% |
| 4 | 11 | rORF2 - 16 μg (1 dose) | 0% | 18.2% | 1.50 ± 4.74% | 36.3% |
| 5 | 12 | rORF2 - 8 μg (1 dose) | 0% | 8.3% | 0.68 ± 1.15% | 16.7% |
| 6 | 11 | rORF2 - 4 μg (1 dose) | 9.1% | 9.1% | 2.95 ± 5.12% | 36.4% |
| 7 | 12 | KV (2 doses) | 16.7% | 41.7% | 7.27 ± 22.9% | 41.7% |
| 8 | 10 | Challenge Controls | 10% | 80% | 9.88 ± 29.2% | 90.0% |
| 9 | 11 | Strict Negative Controls | 0% | 63.6% | 0/11 (0%) | 90.9% | vORF2 = isolated viral ORF2;
rORF2 = recombinant baculovirus expressed ORF2;
KV or killed whole cell virus = PCV2 virus grown in suitable cell culture Results of this study indicate that all further vaccine efforts should focus on a rORF2 vaccine. Overall, nasal shedding of PCV2 was detected post-challenge and vaccination with a PCV2 vaccine resulted in a reduction of shedding. Immunohistochemistry of selected lymphoid tissues also served as a good parameter for vaccine efficacy, whereas large differences in ADWG, clinical symptoms, and gross lesions were not detected between groups. This study was complicated by the fact that extraneous PCV2 was introduced at some point during the study, as evidenced by nasal shedding of PCV2, PCV2 seroconversion and positive IHC tissues in Group 9, the strict negative control group.

Discussion

Seven PCV2 vaccines were evaluated in this study, which included three different dose levels of vORF2 antigen administered once on Day 0, three different dose levels of rORF2 antigen administered once on Day 0 and one dose level of killed whole cell PCV2 vaccine administered on Day 0 and Day 14. Overall, Group 5, which received 1 dose of vaccine containing 8 μg of rORF2 antigen, had the best results. Group 5 had the highest ADWG, the lowest incidence of abnormal behavior, the lowest incidence of abnormal respiration, the second lowest incidence of cough, the lowest incidence of overall clinical symptoms, the lowest mortality rate, the lowest rate of nasal shedding of PCV2, the second lowest rate for mean % lung lesions and the lowest incidence rate for positive IHC tissues.

Interestingly, Group 4, which received a higher dose of rORF2 antigen than Group 5, did not perform as well or better than Group 5. Group 4 had a slightly lower ADWG, a higher incidence of abnormal behavior, a higher incidence of overall clinical symptoms, a higher rate of nasal shedding of PCV2, a higher mean % lung lesions, and a higher rate for positive IHC tissues than Group 5. Statistical analysis, which may have indicated that the differences between these two groups were not statistically significant, was not conducted on these data, but there was an observed trend that Group 4 did not perform as well as Group 5.

Post-vaccination, 6 pigs died at the first study site. Four of the six pigs were from Group 8 or Group 9, which received no vaccine. None of the six pigs demonstrated lesions consistent with PMWS, no adverse events were reported and overall, all seven vaccines appeared to be safe when administered to pigs approximately 11 days of age. During the post-vaccination phase of the study, pigs receiving either of three dose levels of vORF2 vaccine or killed whole cell vaccine had the highest IFAT levels, while Group 5 had the lowest IFAT levels just prior to challenge, of the vaccine groups.

Although not formally proven, the predominant route of transmission of PCV2 to young swine shortly after weaning is believed to be by oronasal direct contact and an efficacious vaccine that reduces nasal shedding of PCV2 in a production setting would help control the spread of infection. Groups receiving one of three vORF2 antigen levels and the group receiving 8 μg of rORF2 had the lowest incidence rate of nasal shedding of PCV2 (8.3%). Expectedly, the challenge control group had the highest incidence rate of nasal shedding (80%).

Gross lesions in pigs with PMWS secondary to PCV2 infection typically consist of generalized lymphadenopathy in combination with one or a multiple of the following: (1) interstitial pneumonia with interlobular edema, (2) cutaneous pallor or icterus, (3) mottled atrophic livers, (4) gastric ulcers and (5) nephritis. At necropsy, icterus, hepatitis, nephritis, and gastric ulcers were not noted in any groups and lymphadenopathy was not specifically examined for. The mean % lung lesion scores varied between groups. The group receiving 16 μg of vORF2 antigen had the lowest mean % lung lesion score (0.40±0.50%), followed by the group that received 8 μg of rORF2 (0.68±1.15%). As expected, the challenge control group had the highest mean % lung lesion score (9.88±29.2%). In all four groups, the mean % lung lesion scores were elevated due to one pig in each of these groups that had very high lung lesion scores. Most of the lung lesions were described as red/purple and consolidated. Typically, lung lesions associated with PMWS are described as tan and non-collapsible with interlobular edema. The lung lesions noted in this study were either not associated with PCV2 infection or a second pulmonary infectious agent may have been present. Within the context of this study, the % lung lesion scores probably do not reflect a true measure of the amount of lung infection due to PCV2.

Other researchers have demonstrated a direct correlation between the presence of PCV2 antigen by IHC and histopathology. Histopathology on select tissues was not conducted with this study. Group 1 (16 μg of vORF2) and Group 5 (8 μg of rORF2) had the lowest incidence rate of pigs positive for PCV2 antigen (8.3%), while Group 9 (the strict negative control group −90.9%) and Group 8 (the challenge control group −90.0%) had the highest incidence rates for pigs positive for PCV2 antigen. Due to the non-subjective nature of this test, IHC results are probably one of the best parameters to judge vaccine efficacy on.

Thus, in one aspect of the present invention, the Minimum Portective Dosage (MPD) of a 1 ml/1 dose recombinant product with extracted PCV2 ORF2 (rORF2) antigen in the CDCD pig model in the face of a PCV2 challenge was determined. Of the three groups that received varying levels of rORF2 antigen, Group 5 (8 μg of rORF2 antigen) clearly had the highest level of protection. Group 5 either had the best results or was tied for the most favorable results with regard to all of the parameters examined. When Group 5 was compared with the other six vaccine groups post-challenge, Group 5 had the highest ADWG (0.94±0.22 lbs/day), the lowest incidence of abnormal behavior (0%), the second lowest incidence of cough (8.3%), the lowest incidence of overall clinical symptoms (8.3%), the lowest mortality rate (0%), the lowest rate of nasal shedding of PCV2 (8.3%), the second lowest rate for mean % lung lesions (0.68±1.15%) and the lowest incidence rate for positive IHC tissues (16.7%).

In another aspect of the present invention, the MPD of a 1 ml/1 dose conventional product that is partially purified PCV2 ORF2 (vORF2) antigen in the CDCD pig model in the face of a PCV2 challenge was determined. Of the three groups that received varying levels of vORF2 antigen, Group 1 (16 μg of vORF2) had the highest level of protection. Group 1 outperformed Groups 2 and 3 with respect to ADWG, mean % lung lesions, and IHC. Groups 1 and 2 (8 μg of vORF2 antigen) performed equally with respect to overall incidence of clinical symptoms, Group 3 (4 μg of vORF2 antigen) had the lowest mortality rate, and all three groups performed equally with respect to nasal shedding. Overall, vORF vaccines did not perform as well as rORF vaccines.

In yet another aspect of the present invention, the efficacy of a maximum dose of a 2 ml/2 dose Conventional Killed PCV2 vaccine in the CDCD pig model in the face of a PCV2 challenge was determined. Of the seven vaccines evaluated in this study, the killed whole cell PCV2 vaccine performed the worst. Piglets receiving two doses of killed whole cell PCV2 vaccine had the lowest ADWG, the second highest rate of abnormal behavior (58.3%), the second highest overall incidence of clinical symptoms (58.3%), the highest mortality rate (16.7%), the second highest incidence of nasal shedding (41.7%), highest mean % lung lesions (9.88±29.2%), a high incidence of lung lesions noted (75%) and a moderate IHC incidence rate in tissues (41.7%). However, it was still effective at invoking an immune response.

In still another aspect of the present invention, nasal shedding of PCV2 was assessed as an efficacy parameter and the previous PCV2 efficacy parameters from previous studies were reconfirmed. Results from this study indicate that nasal shedding of PCV2 occurs following intra nasal challenge and that PCV2 vaccines reduce nasal shedding of PCV2 post-challenge. Furthermore, results from this study and reports in the literature indicate that IHC should continue to be evaluated in future PCV2 vaccine trials as well.

Some additional conclusions arising from this study are that lymphadenopathy is one of the hallmarks of PMWS. Another one of the hallmarks of PMWS is lymphoid depletion and multinucleated/giant histiocytes. Additionally, no adverse events or injection site reactions were noted for any of the 7 PCV2 vaccines and all 7 PCV2 vaccines appeared to be safe when administered to young pigs.

EXAMPLE 5

This example tests the efficacy of eight PCV2 candidate vaccines and reconfirms PCV2 challenge parameters from earlier challenge studies following exposure to a virulent strain of PCV2. One hundred and fifty (150) cesarean derived colostrum deprived (CDCD) piglets, 6-16 days of age, were blocked by weight and randomly divided into 10 groups of equal size. Table 16 sets forth the General Study Design for this Example.

TABLE 16

General Study Design

| Group | No. Of Pigs | Treatment | Day of Treatment | KLH/ICFA on Day 22 and Day 28 | Challenge with Virulent PCV2 on Day 25 | PRRSV MLV on Day 46 | Necropsy on Day 50 |
| --- | --- | --- | --- | --- | --- | --- | --- |
| 1 | 15 | PVC2 Vaccine 1 16 μg rORF2 - IMS 1314 | 0 & 14 | + | + | + | + |
| 2 | 15 | PVC2 Vaccine 2 16 μg vORF2 - Carbopol | 0 & 14 | + | + | + | + |
| 3 | 15 | PCV2 Vaccine 3 16 μg rORF2 - Carbopol | 0 & 14 | + | + | + | + |
| 4 | 15 | PCV2 Vaccine 2 16 μg vORF2 - Carbopol | 0 | + | + | + | + |
| 5 | 15 | PVC2 Vaccine 3 4 μg rORF2 - Carbopol | 0 & 14 | + | + | + | + |
| 6 | 15 | PVC2 Vaccine 3 1 μg rORF2 - Carbopol | 0 & 14 | + | + | + | + |

TABLE 16-continued

General Study Design

| Group | No. Of Pigs | Treatment | Day of Treatment | KLH/ICFA on Day 22 and Day 28 | Challenge with Virulent PCV2 on Day 25 | PRRSV MLV on Day 46 | Necropsy on Day 50 |
|---|---|---|---|---|---|---|---|
| 7 | 15 | PVC2 Vaccine 3 0.25 µg rORF2 - Carbopol | 0 & 14 | + | + | + | + |
| 8 | 15 | PVC2 Vaccine 4 > 8.0 log KV - Carbopol | 0 & 14 | + | + | + | + |
| 9 | 15 | Challenge Controls | N/A | + | + | + | + |
| 10 | 15 | None - Strict Negative Control Group | N/A | + | − | + | + | vORF2 = isolated viral ORF2;
rORF2 = recombinant baculovirus expressed ORF2;
KV or killed whole cell virus = PCV2 virus grown in suitable cell culture The vaccine formulation given to each group were as follows. PCV2 Vaccine No. 1, administered at 1×2 ml dose to Group 1, was a high dose (16 ug/2 ml dose) of inactivated recombinant ORF2 antigen adjuvanted with IMS 1314 (16 ug rORF2-IMS 1314). PCV2 Vaccine No. 2, administered at 1×2 ml dose to Group 2, was a high dose (16 ug/2 ml dose) of a partially purified VIDO R-1 generated PCV2 ORF2 antigen adjuvanted with Carbopol (16 ug vORF2-Carbopol). PCV2 Vaccine No. 3, administered at 1×2 ml dose to Group 3, was a high dose (16 ug/2 ml dose) of inactivated recombinant ORF2 antigen adjuvanted with Carbopol (16 ug rORF2-Carbopol). PCV2 Vaccine No. 4, administered at 1×1 ml dose to Group 4, was a high dose (16 ug/1 ml dose) of a partially purified VIDO R-1 generated PCV2 ORF2 antigen adjuvanted with Carbopol (16 ug vORF2-Carbopol). Vaccine No. 5, administered at 1×2 ml dose to Group 5, was a 4 ug/2 ml dose of an inactivated recombinant ORF2 antigen adjuvanted with Carbopol (4 ug rORF2-Carbopol). PCV2 Vaccine No. 6, administered at 1×2 ml dose to Group 6, was a 1 ug/2 ml dose of an inactivated recombinant ORF2 antigen adjuvanted with Carbopol (1 ug rORF2-Carbopol). PCV2 Vaccine No. 7, administered at 1×2 ml dose to Group 7, was a low dose (0.25 ug/2 ml dose) of inactivated recombinant ORF2 antigen adjuvanted with Carbopol (0.25 ug rORF2-Carbopol). PCV2 Vaccine No. 8, administered at 1×2 ml dose to Group 8, was a high dose (pre-inactivation titer>8.0 log/2 ml dose) Inactivated Conventional Killed VIDO R-1 generated PCV2 Struve antigen adjuvanted with Carbopol (>8.0 log KV-Carbopol). On Day 0, Groups 1-8 were treated with their assigned vaccines. Groups 1-3 and 5-8 received boosters of their respective vaccines again on Day 14. The effectiveness of a single dose of 16 µg of vORF2-Carbopol was tested on Group 4 which did not receive a booster on Day 14. Piglets were observed for adverse events and injection site reactions following both vaccinations. On Day 21 the piglets were moved to a second study site where Groups 1-9 were group housed in one building and Group 10 was housed in a separate building. All pigs received keyhole limpet hemocyanin emulsified with incomplete Freund's adjuvant (KLH/ICFA) on Days 22 and 28. On Day 25, Groups 1-9 were challenged with approximately 4 logs of virulent PCV2 virus. By Day 46, very few deaths had occurred in the challenge control group. In an attempt to immunostimulate the pigs and increase the virulence of the PCV2 challenge material, all Groups were treated with INGELVAC® PRRSV MLV (Porcine Reproductive and Respiratory Vaccine, Modified Live Virus) on Day 46.

Pre- and post-challenge blood samples were collected for PCV2 serology. Post-challenge, body weight data for determination of average daily weight gain (ADWG) and observations of clinical signs were collected. On Day 50, all surviving pigs were necropsied, gross lesions were recorded, lungs were scored for pathology, and selected tissues were preserved in formalin for examination by Immunohistochemistry (IHC) for detection of PCV2 antigen at a later date.

Materials and Methods

This was a partially-blind vaccination-challenge feasibility study conducted in CDCD pigs, 6 to 16 days of age on Day 0. To be included in the study, PCV2 IFA titers of sows were ≦1:1000. Additionally, the serologic status of sows were from a known PRRS-negative herd. Sixteen (16) sows were tested for PCV2 serological status and all sixteen (16) had a PCV2 titer of ≦1000 and were transferred to the first study site. One hundred fifty (150) piglets were delivered by cesarean section surgeries and were available for this study on Day −3. On Day −3, 150 CDCD pigs at the first study site were weighed, identified with ear tags, blocked by weight and randomly assigned to 1 of 10 groups, as set forth above in table 16. Blood samples were collected from all pigs. If any test animal meeting the inclusion criteria was enrolled in the study and was later excluded for any reason, the Investigator and Monitor consulted in order to determine the use of data collected from the animal in the final analysis. The date of which enrolled piglets were excluded and the reason for exclusion was documented. No sows meeting the inclusion criteria, selected for the study and transported to the first study site were excluded. No piglets were excluded from the study, and no test animals were removed from the study prior to termination. Table 17 describes the time frames for the key activities of this Example.

TABLE 17

Study Activities

| Study Day | Actual Dates | Study Activity |
|---|---|---|
| −3 | Apr. 04, 2003 | Weighed pigs; health exam; randomized to groups; collected blood samples |
| −3, 0-21 | Apr. 04, 2003 Apr. 07, 2003 to May 27, 2003 | Observed for overall health and for adverse events post-vaccination |
| 0 | Apr. 07, 2003 | Administered respective IVPs to Groups 1-8 |
| 0-7 | Apr. 07, 2003 to Apr. 14, 2003 | Observed pigs for injection site reactions |
| 14 | Apr. 21, 2003 | Boostered Groups 1-3, 5-8 with respective IVPs; blood sampled all pigs |
| 14-21 | Apr. 21, 2003 to Apr. 28, 2003 | Observed pigs for injection reactions |
| 19-21 | Apr. 26, 2003 to Apr. 28, 2003 | Treated all pigs with antibiotics |
| 21 | Apr. 28, 2003 | Pigs transported from Struve Labs, Inc. to Veterinary Resources, Inc.(VRI) |
| 22-50 | Apr. 28, 2003 to May 27, 2003 | Observed pigs for clinical signs post-challenge |
| 22 | Apr. 29, 2003 | Treated Groups 1-10 with KLH/ICFA |
| 25 | May 02, 2003 | Collected blood samples from all pigs; weighed all pigs; challenged Groups 1-9 with PCV2 challenge material |
| 28 | May 05, 2003 | Treated Groups 1-10 with KLH/ICFA |
| 32 | May 09, 2003 | Collected blood samples from all pigs |
| 46 | May 23, 2003 | Administered INGELVAC ® PRRS MLV to all groups |
| 50 | May 27, 2003 | Collected blood samples, weighed and necropsied all pigs; gross lesions were recorded; lungs were evaluated for lesions; fresh and formalin fixed tissue samples were saved; In-life phase of the study was completed |

Following completion of the in-life phase of the study, formalin fixed tissues were examined by Immunohistochemistry (IHC) for detection of PCV2 antigen by a pathologist, blood samples were evaluated for PCV2 serology, and average daily weight gain (ADWG) was determined from Day 25 to Day 50.

Animals were housed at the first study site in individual cages in seven rooms from birth to approximately 11 days of age (approximately Day 0 of the study). Each room was identical in layout and consisted of stacked individual stainless steel cages with heated and filtered air supplied separately to each isolation unit. Each room had separate heat and ventilation, thereby preventing cross-contamination of air between rooms. Animals were housed in two different buildings at the second study site. Group 10 (The Strict negative control group) was housed separately in a converted nursery building and Groups 1-9 were housed in a converted farrowing building. Each group was housed in a separate pen (14-15 pigs per pen) and each pen provided approximately 2.3 square feet per pig. Groups 2, 4 and 8 were penned in three adjacent pens on one side of the alleyway and Groups 1, 3, 5, 6, 7, and 9 were penned in six adjacent pens on the other side of the alleyway. The Group separation was due to concern by the Study Monitor that vaccines administered to Groups 2, 4, and 8 had not been fully inactivated. Each pen was on an elevated deck with plastic slatted floors. A pit below the pens served as a holding tank for excrement and waste. Each building had its own separate heating and ventilation systems, with little likelihood of cross-contamination of air between buildings.

At the first study site, piglets were fed a specially formulated milk ration from birth to approximately 3 weeks of age. All piglets were consuming solid, special mixed ration by Day 21 (approximately 4½ weeks of age). At the second study site, all piglets were fed a custom non-medicated commercial mix ration appropriate for their age and weight, ad libitum. Water at both study sites was also available ad libitum.

All test pigs were treated with 1.0 mL of NAXCEL®, IM, in alternating hams on Days 19, 20, and 21. In addition, Pig No. 11 (Group 1) was treated with 0.5 mL of NAXCEL® IM on Day 10, Pig No. 13 (Group 10) was treated with 1 mL of Penicillin and 1 mL of PREDEF® 2× on Day 10, Pig No. 4 (Group 9) was treated with 1.0 mL of NAXCEL® IM on Day 11, and Pigs 1 (Group 1), 4 and 11 were each treated with 1.0 mL of NAXCEL® on Day 14 for various health reasons.

While at both study sites, pigs were under veterinary care. Animal health examinations were conducted on Day −3 and were recorded on the Health Examination Record Form. All animals were in good health and nutritional status before vaccination as determined by observation on Day 0. All test animals were observed to be in good health and nutritional status prior to challenge. Carcasses and tissues were disposed of by rendering. Final disposition of study animals was recorded on the Animal Disposition Record.

On Days 0 and 14, pigs assigned to Groups 1-3 and 5-8 received 2.0 mL of assigned PCV2 Vaccines 1-4, respectively, IM in the right and left neck region, respectively, using a sterile 3.0 mL Luer-lock syringe and a sterile 20 g×½" needle. Pigs assigned to Group 4 received 1.0 mL of PCV2 Vaccine No. 2, IM in the right neck region using a sterile 3.0 mL Luer-lock syringe and a sterile 20 g×½" needle on Day 0 only.

On Day 22 all test pigs received 2.0 mL of KLH/ICFA IM in the left neck region using a sterile 3.0 mL Luer-lock syringe and a sterile 20 g×1" needle. On Day 28 all test pigs received 2.0 mL of KLH/ICFA in the right ham region using a sterile 3.0 mL Luer-lock syringe and a sterile 20 g×1" needle.

On Day 25, pigs assigned to Groups 1-9 received 1.0 mL of PCV2 ISUVDL challenge material (3.98 $\log_{10}$ $TCID_{50}$/mL) IM in the right neck region using a sterile 3.0 mL Luer-lock syringe and a sterile 20 g×1" needle. An additional 1.0 mL of the same material was administered IN to each pig (0.5 mL per nostril) using a sterile 3.0 mL Luer-lock syringe and nasal canula.

On Day 46, all test pigs received 2.0 mL INGELVAC® PRRS MLV, IM, in the right neck region using a sterile 3.0 mL Luer0lock syringe and a sterile 20 g×1" needle. The PRRSV MLV was administered in an attempt to increase virulence of the PCV2 challenge material.

Test pigs were observed daily for overall health and adverse events on Day −3 and from Day 0 to Day 21. Each of the pigs were scored for normal or abnormal behavior, respiration or cough. Observations were recorded on the Clinical Observation Record. All test pigs were observed from Day 0 to Day 7, and Group 7 was further observed from Day 14 to 21, for injection site reactions. Average daily weight gain was determined by weighing each pig on a calibrated scale on Days −3, 25 and 50, or on the day that a pig was found dead after challenge. Body weights were recorded on the Body Weight Form. Day −3 body weights were utilized to block pigs prior to randomization. Day 25 and Day 50 weight data was utilized to determine the average daily weight gain (ADWG) for each pig during these time points. For pigs that died after challenge and before Day 50, the ADWG was adjusted to represent the ADWG from Day 25 to the day of death.

In order to determine PCV2 serology, venous whole blood was collected from each piglet from the orbital venous sinus on Days −3 and 14. For each piglet, blood was collected from the orbital venous sinus by inserting a sterile capillary tube into the medial canthus of one of the eyes and draining approximately 3.0 mL of whole blood into a 4.0 mL Serum Separator Tube (SST). On Days 25, 32, and 50, venous whole blood from each pig was collected from the anterior vena cava using a sterile 20 g×1½" Vacutainer® needle (Becton Dickinson and Company, Franklin Lakes, N.J.), a Vaccutainer® needle holder and a 13 mL SST. Blood collections at each time point were recorded on the Sample Collection Record. Blood in each SST was allowed to clot, each SST was then spun down and the serum harvested. Harvested serum was transferred to a sterile snap tube and stored at −70±10° C. until tested at a later date. Serum samples were tested for the presence of PCV2 antibodies by BIVI-R&D personnel.

Pigs were observed once daily from Day 22 to Day 50 for clinical symptoms and scored for normal or abnormal behavior, respiration or cough. Clinical observations were recorded on the Clinical Observation Record.

Pigs Nos. 46 (Group 1) and 98 (Groups 9) died at the first study site. Both of these deaths were categorized as bleeding deaths and necropsies were not conducted on these two pigs. At the second study site, pigs that died after challenge and prior to Day 50, and pigs euthanized on Day 50, were necropsied. Any gross lesions were noted and the percentages of lung lobes with lesions were recorded on the Necropsy Report Form.

From each of the pigs necropsied at the second study site, a tissue sample of tonsil, lung, heart, and mesenteric lymph node was placed into a single container with buffered 10% formalin; while another tissue sample from the same aforementioned organs was placed into a Whirl-pak® (M-Tech Diagnostics Ltd., Thelwall, UK) and each Whirl-pak® was placed on ice. Each container was properly labeled. Sample collections were recorded on the Necropsy Report Form. Afterwards, formalin-fixed tissue samples and a Diagnostic Request Form were submitted for IHC testing. IHC testing was conducted in accordance with standard laboratory procedures for receiving samples, sample and slide preparation, and staining techniques. Fresh tissues in Whirl-paks® were shipped with ice packs to the Study Monitor for storage (−70°±10° C.) and possible future use.

Formalin-fixed tissues were examined by a pathologist for detection of PCV2 by IHC and scored using the following scoring system: 0=None; 1=Scant positive staining, few sites; 2=Moderate positive staining, multiple sites; and 3=Abundant positive staining, diffuse throughout the tissue. For analytical purposes, a score of 0 was considered "negative," and a score of greater than 0 was considered "positive."

Results

Results for this example are given below. It is noted that Pigs No. 46 and 98 died on days 14 and 25 respectively. These deaths were categorized as bleeding deaths. Pig No. 11 (Group 1) was panting with rapid respiration on Day 15. Otherwise, all pigs were normal for behavior, respiration and cough during this observation period and no systemic adverse events were noted with any groups. No injection site reactions were noted following vaccination on Day 0. Following vaccination on Day 14, seven (7) out of fourteen (14) Group 1 pigs (50.0%) had swelling with a score of "2" on Day 15. Four (4) out of fourteen (14) Group 1 (28.6%) still had a swelling of "2" on Day 16. None of the other groups experienced injection site reactions following either vaccination.

Average daily weight gain (ADWG) results are presented below in Table 18. Pigs No. 46 and 98 that died from bleeding were excluded from group results. Group 4, which received one dose of 16 ug vORF2-Carbopol, had the highest ADWG (1.16±0.26 lbs/day), followed by Groups 1, 2, 3, 5, 6, and 10 which had ADWGs that ranged from 1.07±0.23 lbs/day to 1.11±0.26 lbs/day. Group 9 had the lowest ADWG (0.88±0.29 lbs/day), followed by Groups 8 and 7, which had ADWGs of 0.93±0.33 lbs/day and 0.99±0.44 lbs/day, respectively.

TABLE 18

Summary of Group Average Daily Weight Gains (ADWG)

| Group | Treatment | N | ADWG - lbs/day (Day 25 to Day 50) or adjusted for pigs dead before Day 50 |
|---|---|---|---|
| 1 | rORF2 - 16 µg - IMS 1314 2 doses | 14 | 1.08 ± 0.30 lbs/day |
| 2 | vORF2 - 16 µg - Carbopol 2 doses | 15 | 1.11 ± 0.16 lbs/day |
| 3 | rORF2 - 16 µg - Carbopol 2 doses | 15 | 1.07 ± 0.21 lbs/day |
| 4 | vORF2 - 16 µg - Carbopol 1 dose | 15 | 1.16 ± 0.26 lbs/day |
| 5 | rORF2 - 4 µg - Carbopol 1 dose | 15 | 1.07 ± 0.26 lbs/day |
| 6 | rORF2 - 1 µg - Carbopol 2 doses | 15 | 1.11 ± 0.26 lbs/day |
| 7 | rORF2 - 0.25 µg - Carbopol 2 doses | 15 | 0.99 ± 0.44 lbs/day |
| 8 | KV > 8.0 log - Carbopol 2 doses | 15 | 0.93 ± 0.33 lbs/day |
| 9 | Challenge Controls | 14 | 0.88 ± 0.29 lbs/day |
| 10 | Strict Negative Controls | 15 | 1.07 ± 0.23 lbs/day | vORF2 = isolated viral ORF2;
rORF2 = recombinant baculovirus expressed ORF2;
KV or killed whole cell virus = PCV2 virus grown in suitable cell culture PVC2 serology results are presented below in Table 19. All ten (10) groups were seronegative for PCV2 on Day −3. On Day 14, PCV2 titers remained low for all ten (10) groups (range of 50-113). On Day 25, Group 8, which received the whole cell killed virus vaccine, had the highest PCV2 titer (4617), followed by Group 2, which received 16 ug vORF2-Carbopol, Group 4, which received as single dose of 16 ug vORF2-Carbopol, and Group 3, which received 16 ug rORF2-Carbopol, which had titers of 2507, 1920 and 1503 respectively. On Day 32 (one week post challenge), titers for Groups 1-6 and Group 8 ranged from 2360 to 7619; while Groups 7 (0.25 ug rORF2-Carbopol), 9 (Challenge Control), and 10 (Strict negative control) had titers of 382, 129 and 78 respectively. On Day 50 (day of necropsy), all ten (10) groups demonstrated high PCV2 titers (≧1257).

On Days 25, 32, and 50, Group 3, which received two doses of 16 ug rORF2-Carbopol had higher antibody titers than Group 1, which received two doses of 16 ug rORF2-IMS 1314. On Days 25, 32 and 50, Group 2, which received two doses of 16 ug vORF2 had higher titers than Group 4, which received only one does of the same vaccine. Groups 3, 5, 6, 7, which received decreasing levels of rORF2-Carbopol, of 16, 4, 1, and 0.25 ug respectively, demonstrated correspondingly decreasing antibody titers on Days 25 and 32.

Overall mortality rates between groups varied as well. Group 8, which received 2 doses of KV vaccine had the highest mortality rate of 20.0%; followed by Group 9, the challenge control group, and Group 7, which received 0.25 ug rORF2-Carbopol and had mortality rates of 14.3% and 13.3% respectively. Group 4, which received one dose of 16 ug vORF2-Carbopol had a 6.7% mortality rate. All of the other Groups, 1, 2, 3, 5, 6, and 10 had a 0% mortality rate.

TABLE 19

Summary of Group PCV2 IFA Titers

| Group | Treatment | Day −3 | Day 14** | Day 25*** | Day 32 | Day 50**** |
|---|---|---|---|---|---|---|
| 1 | rORF2 - 16 µg - IMS 1314 2 doses | 50 | 64 | 646 | 3326 | 4314 |
| 2 | vORF2 - 16 µg - Carbopol 2 doses | 50 | 110 | 2507 | 5627 | 4005 |
| 3 | rORF2 - 16 µg - Carbopol 2 doses | 50 | 80 | 1503 | 5120 | 6720 |
| 4 | vORF2 - 16 µg - Carbopol 1 dose | 50 | 113 | 1920 | 3720 | 1257 |
| 5 | rORF2 - 4 µg - Carbopol 1 dose | 50 | 61 | 1867 | 3933 | 4533 |
| 6 | rORF2 - 1 µg - Carbopol 2 doses | 50 | 70 | 490 | 2360 | 5740 |
| 7 | rORF2 - 0.25 µg - Carbopol 2 doses | 50 | 73 | 63 | 382 | 5819 |
| 8 | KV > 8.0 log - Carbopol 2 doses | 50 | 97 | 4617 | 7619 | 10817 |
| 9 | Challenge Controls | 50 | 53 | 50 | 129 | 4288 |
| 10 | Strict Negative Controls | 50 | 50 | 50 | 78 | 11205 | vORF2 = isolated viral ORF2;
rORF2 = recombinant baculovirus expressed ORF2;
KV or killed whole cell virus = PCV2 virus grown in suitable cell culture
*For calculation purposes, a ≦ 100 IFA titer was designated as a titer of "50"; a ≧ 6400 IFA titer was designated as a titer of "12,800".
**Day of Challenge
***Day of Necropsy The results from the post-challenge clinical observations are presented below. Table 20 includes observations for Abnormal Behavior, Abnormal Respiration, Cough and Diarrhea. Table 21 includes the results from the Summary of Group Overall Incidence of Clinical Symptoms and Table 22 includes results from the Summary of Group Mortality Rates Post-challenge. The incidence of abnormal behavior, respiration and cough post-challenge were low in pigs receiving 16 ug rORF2-IMS 1314 (Group 1), 16 ug rORF2-Carbopol (Group 3), 1 ug rORF2-Carbopol (Group 6), 0.25 ug rORF2-Carbopol (Group 7), and in pigs in the Challenge Control Group (Group 9). The incidence of abnormal behavior respiration and cough post-challenge was zero in pigs receiving 16 ug vORF2-Carbopol (Group 2), a single dose of 16 ug vORF2-Carbopol (Group 4), 4 ug rORF2-Carbopol (Group 5), >8 log KV-Carbopol (Group 8), and in pigs in the strict negative control group (Group 10).

The overall incidence of clinical symptoms varied between groups. Pigs receiving 16 ug vORF2-Carbopol (Group 2), a single dose of 16 ug vORF2-Carbopol (Group 4), and pigs in the Strict negative control group (Group 10) had incidence rates of 0%; pigs receiving 16 ug rORF2-Carbopol (Group 3), and 1 ug rORF2-Carbopol (Group 6) had incidence rates of 6.7%; pigs receiving 16 ug rORF2-IMS 1314 (Group 1) had an overall incidence rate of 7.1%; pigs receiving 4 ug rORF2-Carbopol (Group 5), 0.25 ug rORF2-Carbopol (Group 7), and >8 log KV vaccine had incidence rates of 13.3%; and pigs in the Challenge Control Group (Group 9) had an incidence rate of 14.3%.

TABLE 20

Summary of Group Observations for Abnormal Behavior, Abnormal Respiration, and Cough Post-Challenge

| Group | Treatment | N | Abnormal Behavior[1] | Abnormal Behavior[2] | Cough[3] |
|---|---|---|---|---|---|
| 1 | rORF2 - 16 µg - IMS 1314 2 doses | 14 | 0/14 (0%) | 0/14 (0%) | 1/14 (7.1%) |
| 2 | vORF2 - 16 µg - Carbopol 2 doses | 15 | 0/15 (0%) | 0/15 (0%) | 0/15 (0%) |
| 3 | rORF2 - 16 µg - Carbopol 2 doses | 15 | 0/15 (0%) | 0/15 (0%) | 1/15 (6.7%) |
| 4 | vORF2 - 16 µg - Carbopol 1 dose | 15 | 0/15 (0%) | 0/15 (0%) | 0/15 (0%) |
| 5 | rORF2 - 4 µg - Carbopol 1 dose | 15 | 1/15 (6.7%) | 1/15 (6.7%) | 0/15 (0%) |
| 6 | rORF2 - 1 µg - Carbopol 2 doses | 15 | 0/15 (0%) | 0/15 (0%) | 1/15 (6.7%) |
| 7 | rORF2 - 0.25 µg - Carbopol 2 doses | 15 | 0/15 (0%) | 1/15 (6.7%) | 1/15 (06.7%) |
| 8 | KV > 8.0 log - Carbopol 2 doses | 15 | 1/15 (6.7%) | 1/15 (6.7%) | 0/15 (0%) |
| 9 | Challenge Controls | 14 | 1/14 (7.1%) | 1/14 (7.1%) | 2/14 (14/3%) |
| 10 | Strict Negative Controls | 15 | 0/15 (0%) | 0/15 (0%) | 0/15 (0%) |

[1]Total number of pigs in each group that demonstrated any abnormal behavior for at least one day
[2]Total number of pigs in each group that demonstrated any abnormal respiration for at least one day
[3]Total number of pigs in each group that demonstrated a cough for at least one day

TABLE 21

Summary of Group Overall Incidence of Clinical Symptoms Post-Challenge

| Group | Treatment | N | Incidence of pigs with Clinical Symptoms[1] | Incidence Rate |
|---|---|---|---|---|
| 1 | rORF2 - 16 μg - IMS 1314 2 doses | 14 | 1 | 7.1% |
| 2 | vORF2 - 16 μg - Carbopol 2 doses | 15 | 0 | 0.0% |
| 3 | rORF2 - 16 μg - Carbopol 2 doses | 15 | 1 | 6.7% |
| 4 | vORF2 - 16 μg - Carbopol 1 dose | 15 | 0 | 0.0% |
| 5 | rORF2 - 4 μg - Carbopol 1 dose | 15 | 2 | 13.3% |
| 6 | rORF2 - 1 μg - Carbopol 2 doses | 15 | 1 | 6.7% |
| 7 | rORF2 - 0.25 μg - Carbopol 2 doses | 15 | 2 | 13.3% |
| 8 | KV > 8.0 log - Carbopol 2 doses | 15 | 2 | 13.3% |
| 9 | Challenge Controls | 14 | 2 | 14.3% |
| 10 | Strict Negative Controls | 15 | 0 | 0.0% | vORF2 = isolated viral ORF2;
rORF2 = recombinant baculovirus expressed ORF2;
KV or killed whole cell virus = PCV2 virus grown in suitable cell culture
[1]Total number of pigs in each group that demonstrated any clinical symptom for at least one day

TABLE 22

Summary of Group Mortality Rates Post-Challenge

| Group | Treatment | N | Dead Post-challenge | Mortality Rate |
|---|---|---|---|---|
| 1 | rORF2 - 16 μg - IMS 1314 2 doses | 14 | 0 | 0.0% |
| 2 | vORF2 - 16 μg - Carbopol 2 doses | 15 | 0 | 0.0% |
| 3 | rORF2 - 16 μg - Carbopol 2 doses | 15 | 0 | 0.0% |
| 4 | vORF2 - 16 μg - Carbopol 1 dose | 15 | 1 | 6.7% |
| 5 | rORF2 - 4 μg - Carbopol 1 dose | 15 | 0 | 0.0% |
| 6 | rORF2 - 1 μg - Carbopol 2 doses | 15 | 0 | 0.0% |
| 7 | rORF2 - 0.25 μg - Carbopol 2 doses | 15 | 2 | 13.3% |
| 8 | KV > 8.0 log - Carbopol 2 doses | 15 | 3 | 20.0% |
| 9 | Challenge Controls | 14 | 2 | 14.3% |
| 10 | Strict Negative Controls | 15 | 0 | 0.0% | vORF2 = isolated viral ORF2;
rORF2 = recombinant baculovirus expressed ORF2;
KV or killed whole cell virus = PCV2 virus grown in suitable cell culture The Summary of Group Mean Percentage Lung Lesions and Tentative Diagnosis is given below in Table 23. Group 9, the challenge control group, had the highest percentage lung lesions with a mean of 10.81±23.27%, followed by Group 7, which received 0.25 ug rORF2-Carbopol and had a mean of 6.57±24.74%, Group 5, which received 4 ug rORF2-Carbopol and had a mean of 2.88±8.88%, and Group 8, which received the KV vaccine and had a mean of 2.01±4.98%. The remaining six (6) groups had lower mean percentage lung lesions that ranged from 0.11±0.38% to 0.90±0.15%.

Tentative diagnosis of pneumonia varied among the groups. Group 3, which received two doses of 16 ug rORF2-Carbopol, had the lowest tentative diagnosis of pneumonia, with 13.3%. Group 9, the challenge control group, had 50% of the group tentatively diagnosed with pneumonia, followed by Group 10, the strict negative control group and Group 2, which received two doses of 16 ug vORF2-Carbopol, with 46.7% of 40% respectively, tentatively diagnosed with pneumonia.

Groups 1, 2, 3, 5, 9, and 10 had 0% of the group tentatively diagnosed as PCV2 infected; while Group 8, which received two doses if KV vaccine, had the highest group rate of tentative diagnosis of PCV2 infection, which 20%. Group 7, which received two doses of 0.25 ug rORF2-Carbopol, and Group 4, which received one dose of 16 ug vORF2-Carbopol had tentative group diagnoses of PCV2 infection in 13.3% and 6.7% of each group, respectively.

Gastric ulcers were only diagnosed in one pig in Group 7 (6.7%); while the other 9 groups remained free of gastric ulcers.

TABLE 23

Summary of Group Mean % Lung Lesion and Tentative Diagnosis

| Group | Treatment | N | No. Of pigs that shed for at least one day | Incidence Rate |
|---|---|---|---|---|
| 1 | rORF2 - 16 μg - IMS 1314 2 doses | 15 | 0 | 0% |
| 2 | vORF2 - 16 μg - Carbopol 2 doses | 15 | 1 | 6.7% |
| 3 | rORF2 - 16 μg - Carbopol 2 doses | 15 | 3 | 20.0% |
| 4 | vORF2 - 16 μg - Carbopol 1 dose | 15 | 2 | 13.3% |
| 5 | rORF2 - 4 μg - Carbopol 1 dose | 15 | 3 | 20.0% |
| 6 | rORF2 - 1 μg - Carbopol 2 doses | 15 | 6 | 40.0% |
| 7 | rORF2 - 0.25 μg - Carbopol 2 doses | 15 | 7 | 46.7% |
| 8 | KV > 8.0 log - Carbopol 2 doses | 15 | 12 | 80% |
| 9 | Challenge Controls | 14 | 14 | 100.0% |
| 10 | Strict Negative Controls | 15 | 14 | 93.3% | vORF2 = isolated viral ORF2;
rORF2 = recombinant baculovirus expressed ORF2;
KV or killed whole cell virus = PCV2 virus grown in suitable cell culture The Summary of Group IHC Positive Incidence Results are shown below in Table 24. Group 1 (16 ug rORF2-IMS 1314) had the lowest group rate of IHC positive results with 0% of the pigs positive for PCV2, followed by Group 2 (16 ug vORF2-Carbopol) and Group 4 (single dose 16 ug vORF2-Carbopol), which had group IHC rates of 6.7% and 13.3% respectively. Group 9, the challenge control group, had the highest IHC positive incidence rate with 100% of the pigs positive for PCV2, followed by Group 10, the strict negative control group, and Group 8 (KV vaccine), with 93.3% and 80% of the pigs positive for PCV2, respectively.

TABLE 24

Summary of Group IHC Positive Incidence Rate

| Group | Treatment | N | No. Of pigs that shed for at least one day | Incidence Rate |
|---|---|---|---|---|
| 1 | rORF2 - 16 μg - IMS 1314 2 doses | 15 | 0 | 0% |
| 2 | vORF2 - 16 μg - Carbopol 2 doses | 15 | 1 | 6.7% |
| 3 | rORF2 - 16 μg - Carbopol 2 doses | 15 | 3 | 20.0% |

TABLE 24-continued

Summary of Group IHC Positive Incidence Rate

| Group | Treatment | N | No. Of pigs that shed for at least one day | Incidence Rate |
|---|---|---|---|---|
| 4 | vORF2 - 16 µg - Carbopol 1 dose | 15 | 2 | 13.3% |
| 5 | rORF2 - 4 µg - Carbopol 1 dose | 15 | 3 | 20.0% |
| 6 | rORF2 - 1 µg - Carbopol 2 doses | 15 | 6 | 40.0% |
| 7 | rORF2 - 0.25 µg - Carbopol 2 doses | 15 | 7 | 46.7% |
| 8 | KV > 8.0 log - Carbopol 2 doses | 15 | 12 | 80% |
| 9 | Challenge Controls | 14 | 14 | 100.0% |
| 10 | Strict Negative Controls | 15 | 14 | 93.3% | vORF2 = isolated viral ORF2;
rORF2 = recombinant baculovirus expressed ORF2;
KV or killed whole cell virus = PCV2 virus grown in suitable cell culture Discussion Seven PCV2 vaccines were evaluated in this example, which included a high dose (16 µg) of rORF2 antigen adjuvanted with IMS 1314 administered twice, a high dose (16 µg) of vORF2 antigen adjuvanted with Carbopol administered once to one group of pigs and twice to a second group of pigs, a high dose (16 µg) of rORF2 antigen adjuvanted with Carbopol administered twice, a 4 µg dose of rORF2 antigen adjuvanted with Carbopol administered twice, a 1 µg dose of rORF2 antigen adjuvanted with Carbopol administered twice, a low dose (0.25 µg) of rORF2 antigen adjuvanted with Carbopol administered twice, and a high dose (>8 log) of killed whole cell PCV2 vaccine adjuvanted with Carbopol. Overall, Group 1, which received two doses of 16 µg rORF2-IMS 1314, performed slightly better than Groups 2 through 7, which received vaccines containing various levels of either vORF2 or rORF2 antigen adjuvanted with Carbopol and much better than Group 8, which received two doses of killed whole cell PCV2 vaccine. Group 1 had the third highest ADWG (1.80±0.30 lbs/day), the lowest incidence of abnormal behavior (0%), the lowest incidence of abnormal respiration (0%), a low incidence of cough (7.1%), a low incidence of overall clinical symptoms (7.1%), was tied with three other groups for the lowest mortality rate (0%), the second lowest rate for mean % lung lesions (0.15±0.34%), the second lowest rate for pneumonia (21.4%) and the lowest incidence rate for positive IHC tissues (0%). Group 1 was, however, the only group in which injection site reactions were noted, which included 50% of the vaccinates 1 day after the second vaccination. The other vaccines administered to Groups 2 through 7 performed better than the killed vaccine and nearly as well as the vaccine administered to Group 1.

Group 8, which received two doses of killed PCV2 vaccine adjuvanted with Carbopol, had the worst set of results for any vaccine group. Group 8 had the lowest ADWG (0.93±0.33 lbs/day), the second highest rate of abnormal behavior (6.7%), the highest rate of abnormal respiration (6.7%), was tied with three other groups for the highest overall incidence rate of clinical symptoms (13.3%), had the highest mortality rate of all groups (20%), and had the highest positive IHC rate (80%) of any vaccine group. There was concern that the killed whole cell PCV2 vaccine may not have been fully inactivated prior to administration to Group 8, which may explain this group's poor results. Unfortunately, definitive data was not available to confirm this concern. Overall, in the context of this example, a Conventional Killed PCV2 vaccine did not aid in the reduction of PCV2 associated disease.

As previously mentioned, no adverse events were associated with the test vaccines with exception of the vaccine adjuvanted with IMS 1314. Injection site reactions were noted in 50.0% of the pigs 1 day after the second vaccination with the vaccine formulated with IMS 1314 and in 28.6% of the pigs 2 days after the second vaccination. No reactions were noted in any pigs receiving Carbopol adjuvanted vaccines. Any further studies that include pigs vaccinated with IMS 1314 adjuvanted vaccines should continue to closely monitor pigs for injection site reactions.

All pigs were sero-negative for PCV2 on Day −3 and only Group 2 had a titer above 100 on Day 14. On Day 25 (day of challenge), Group 8 had the highest PCV2 antibody titer (4619), followed by Group 2 (2507). With the exception of Groups 7, 9 and 10, all groups demonstrated a strong antibody response by Day 32. By Day 50, all groups including Groups 7, 9 and 10 demonstrated a strong antibody response.

One of the hallmarks of late stage PCV2 infection and subsequent PMWS development is growth retardation in weaned pigs, and in severe cases, weight loss is noted. Average daily weight gain of groups is a quantitative method of demonstrating growth retardation or weight loss. In this example, there was not a large difference in ADWG between groups. Group 8 had the lowest ADWG of 0.88±0.29 lbs/day, while Group 4 had the highest ADWG of 1.16±0.26 lb/day. Within the context of this study there was not a sufficient difference between groups to base future vaccine efficacy on ADWG.

In addition to weight loss—dyspnea, lethargy, pallor of the skin and sometimes icterus are clinical symptoms associated with PMWS. In this example, abnormal behavior and abnormal respiration and cough were noted infrequently for each group. As evidenced in this study, this challenge model and challenge strain do not result in overwhelming clinical symptoms and this is not a strong parameter on which to base vaccine efficacy.

Overall, mortality rates were not high in this example and the lack of a high mortality rate in the challenge control group limits this parameter on which to base vaccine efficacy. Prior to Day 46, Groups 4 and 7 each had one out of fifteen pigs die, Group 9 had two out of fourteen pigs die and Group 8 had three out of fifteen pigs die. Due to the fact that Group 9, the challenge control group was not demonstrating PCV2 clinical symptoms and only two deaths had occurred in this group by Day 46, Porcine Respiratory and Reproductive Syndrome Virus (PRRSV) MLV vaccine was administered to all pigs on Day 46. Earlier studies had utilized INGELVAC® PRRS MLV as an immunostimulant to exasperate PCV2-associated PMWS disease and mortality rates were higher in these earlier studies. Two deaths occurred shortly after administering the PRRS vaccine on Day 46—Group 4 had one death on Day 46 and Group 7 had one death on Day 47—which were probably not associated with the administration of the PRRS vaccine. By Day 50, Group 8, which received two doses of killed vaccine, had the highest mortality rate (20%), followed by Group 9 (challenge control) and Group 7 (0.25 ug rORF2-Carbopol), with mortality rates of 14.3% and 13.3% respectively. Overall, administration of the PRRS vaccine to the challenge model late in the post-challenge observation phase of this example did not significantly increase mortality rates.

Gross lesions in pigs with PMWS secondary to PCV2 infection typically consist of generalized lymphadenopathy in combination with one or more of the following: (1) interstitial pneumonia with interlobular edema, (2) cutaneous pallor or icterus, (3) mottled atrophic livers, (4) gastric ulcers and (5) nephritis. At necropsy (Day 50), icterus, hepatitis, and nephritis were not noted in any groups. A gastric ulcer was noted in one Group 7 pig, but lymphadenopathy was not specifically examined for. Based on the presence of lesions that were consistent with PCV2 infection, three groups had at least one pig tentatively diagnosed with PCV2 (PMWS). Group 8, which received two doses of killed vaccine, had 20% tentatively diagnosed with PCV2, while Group 7 and Group 4 had 13.3% and 6.7%, respectively, tentatively diagnosed with PCV2. The mean % lung lesion scores varied between groups at necropsy. Groups 1, 2, 3, 4, 6 and 10 had low % lung lesion scores that ranged from 0.11±0.38% to 0.90±0.15%. As expected, Group 9, the challenge control group, had the highest mean % lung lesion score (10.81±23.27%). In four groups, the mean % lung lesion scores were elevated due to one to three pigs in each of these groups having very high lung lesion scores. The lung lesions were red/purple and consolidated. Typically, lung lesions associated with PMWS are described as tan, non-collapsible with interlobular edema. The lung lesions noted in this study were either not associated with PCV2 infection or a second pulmonary infectious agent may have been present. Within the context of this study, the % lung lesion scores probably do no reflect a true measure of the amount of lung infection due to PCV2. Likewise, tentative diagnosis of pneumonia may have been over-utilized as well. Any pigs with lung lesions, some as small as 0.10% were listed with a tentative diagnosis of pneumonia. In this example, there was no sufficient difference between groups with respect to gross lesions and % lung lesions on which to base vaccine efficacy.

IHC results showed the largest differences between groups. Group 1 (16 μg rORF2-IMS 1314) had the lowest positive IHC results for PCV2 antigen (0%); while Groups 9 and 10 had the highest positive IHC results with incidence rates of 100% and 93.3% respectively. Groups 3, 5, 6 and 7, which received 16, 4, 1 or 0.25 μg of rORF2 antigen, respectively, adjuvanted with Carbopol, had IHC positive rates of 20%, 20%, 40% and 46.7%, respectively. Group 2, which received two doses of 16 μg vORF2 adjuvanted with Carbopol had an IHC positive rate of 6.7%, while Group 4 which received only one dose of the same vaccine, had an IHC positive rate of 13.3%. Due to the objective nature of this test and the fact that IHC results correlated with expected results, IHC testing is probably one of the best parameters on which to base vaccine efficacy.

Thus in one aspect of the present invention, the Minimum Protective Dosage (MPD) of PCV2 rORF2 antigen adjuvanted with Carbopol in the CDCD pig model in the face of a PCV2 challenge is determined. Groups 3, 5, 6 and 7 each received two doses of rORF2 antigen adjuvanted with Carbopol, but the level of rORF2 antigen varied for each group. Groups 3, 5, 6 and 7 each received 16, 4, 1 or 0.25 μg of rORF2 antigen respectively. In general, decreasing the level of rORF2 antigen decreased PCV2 antibody titers, and increased the mortality rate, mean % lung lesions and the incidence of IHC positive tissues. Of the four groups receiving varying levels of rORF2-Carbopol, Groups 3 and 5, which received two doses of 16 or 4 μg of rORF2 antigen, respectively, each had an IHC positive rate of only 20%, and each had similar antibody titers. Overall, based on IHC positive results, the minimum protective dosage of rORF2 antigen administered twice is approximately 4 μg.

In another aspect of the present invention, the antigenicity of recombinant (rORF2) and VIDO R-1 (vORF2) PCV2 antigens were assessed. Group 2 received two doses of 16 μg vORF2 and Group 3 received two doses of 16 μg rORF2. Both vaccines were adjuvanted with Carbopol. Both vaccines were found to be safe and both had 0% mortality rate. Group 2 had a PCV2 antibody titer of 2507 on Day 25, while Group 3 had a PCV2 antibody titer of 1503. Group 3 had a lower mean % lung lesion score than Group 2 (0.11±0.38% vs. 0.90±0.15%), but Group 2 had a lower IHC positive incidence rate that Group 3 (6.7% vs. 20%). Overall, both vaccines had similar antigenicity, but vORF2 was associated with slightly better IHC results.

In yet another aspect of the present invention, the suitability of two different adjuvants (Carbopol and IMS 1314) was determined. Groups 1 and 3 both received two doses of vaccine containing 16 ug of rORF2 antigen, but Group 1 received the antigen adjuvanted with IMS 1314 while Group 3 received the antigen adjuvanted with Carbopol. Both groups had essentially the same ADWG, essentially the same incidence of clinical signs post-challenge, the same mortality rate, and essentially the same mean % lung lesions; but Group 1 had an IHC positive rate of 0% while Group 3 had an IHC positive rate of 20%. However, Group 3, which received the vaccine adjuvanted with Carbopol had higher IFAT PCV2 titers on Days 25, 32 and 50 than Group 1, which received the vaccine adjuvanted with IMS 1314. Overall, although the PCV2 vaccine adjuvanted with IMS 1314 did provide better IHC results, it did not provide overwhelmingly better protection from PCV2 infection and did induce injection site reaction. Whereas the PCV2 vaccine adjuvanted with Carbopol performed nearly as well as the IMS 1314 adjuvanted vaccine, but was not associated with any adverse events.

In still another aspect of the present invention, the feasibility of PCV2 ORF2 as a 1 ml, 1 dose product was determined. Groups 2 and 4 both received 16 μg of vORF2 vaccine adjuvanted with Carbopol on Day 0, but Group 2 received a second dose on Day 14. Group 4 had a slightly higher ADWG and a lower mean % lung lesions than Group 2, but Group 2 had higher IFAT PCV2 titers on Day 25, 32 and 50, and a slightly lower incidence rate of IHC positive tissues. All other results for these two groups were similar. Overall, one dose of vORF2 adjuvanted with Carbopol performed similar to two doses of the same vaccine.

What is claimed:

1. An immunogenic composition comprising 4 µg to 400 µg of recombinant PCV2 ORF2 protein and a polymer of acrylic or methacrylic acid, wherein said immunogenic composition is effective for providing protective immunity and lessening the severity of one or more clinical symptoms caused by a PCV2 infection after a single dose thereof, in comparison to an animal not receiving said immunogenic composition and wherein said one or more clinical symptoms are selected from the group consisting of wasting, paleness of the skin, unthriftiness, respiratory distress, diarrhea, icterus, jaundice, lung lesions, nasal shedding, cough, diarrhea, and combinations thereof.

2. The immunogenic composition of claim 1, wherein said recombinant PCV2 ORF2 protein is
   i) a polypeptide comprising a sequence selected from the group consisting of SEQ ID NO: 5, SEQ ID NO: 6, SEQ ID NO: 9, SEQ ID NO: 10, and SEQ ID NO: 11;
   ii) any polypeptide that is at least 90% homologous to the polypeptide of i);
   iii) a polypeptide that is encoded by a polynucleotide comprising the sequence of SEQ ID NO: 3 or SEQ ID NO: 4; or
   iv) any polypeptide that is encoded by a polynucleotide that is at least 90% homologous to the polynucleotide of iii).

3. The immunogenic composition of claim 1, wherein said immunogenic composition further comprises an inactivated viral vector.

4. The immunogenic composition of claim 3, wherein said inactivated viral vector is a recombinant baculovirus coding for said recombinant PCV2 ORF2 protein.

5. The immunogenic composition of claim 1, wherein said immunogenic composition further comprises an additional component selected from the group consisting of cell culture supernate, BEI, sodium thiosulfate, carriers, adjuvants, media, viral inactivators, diluents, isotonic agents, immunomodulatory agents, antibiotics, and combinations thereof.

6. The immunogenic composition of claim 1, wherein said polymer of acrylic or methacrylic acid is cross-linked with polyalkenyl ethers of sugars or polyalcohols.

7. The immunogenic composition of claim 1, wherein said polymer of acrylic or methacrylic acid is a carbomer.

8. The immunogenic composition of claim 7, wherein said carbomer is present in an amount of about 500 µg to about 5 mg carbomer per dose.

9. The immunogenic composition of claim 1, wherein said immunogenic composition further comprises a pharmaceutical acceptable salt.

10. The immunogenic composition of claim 1, wherein the amount of said recombinant PCV2 ORF2 protein in said immunogenic composition is 4 µg to 100 µg.

11. The immunogenic composition of claim 1, wherein the amount of said recombinant PCV2 ORF2 protein in said immunogenic composition is 4 µg to 50 µg.

12. The immunogenic composition of claim 1, wherein the amount of said recombinant PCV2 ORF2 protein in said immunogenic composition is 4 µg to 16 µg.

13. The immunogenic composition of claim 1, wherein said immunogenic composition is a vaccine.

14. The immunogenic composition of claim 10, wherein said immunogenic composition is effective for lessening the severity of one or more clinical symptoms caused by a PCV2 infection in comparison to pigs not receiving said immunogenic composition, after the administration of a single dose of said immunogenic composition.

15. The immunogenic composition of claim 1, wherein said one or more clinical symptoms caused by a PCV2 infection are selected from the group consisting of lung lesions, nasal shedding, cough, diarrhea, and combinations thereof.

16. The immunogenic composition of claim 1, wherein one dose of said immunogenic composition is formulated in a volume of at least 1 ml.

17. The immunogenic composition of claim 1, wherein one dose of said immunogenic composition is formulated in a volume of at least 2 ml.

18. The immunogenic composition of claim 1, wherein at least one dose of said immunogenic composition is retained in a container.

19. A kit comprising a container and an instruction manual:
   a. wherein said container comprises at least one dose of an immunogenic composition administered as a single dose immunogenic composition of recombinant PCV2 ORF2 protein and a polymer of acrylic or methacrylic acid, wherein each dose of said single dose immunogenic composition has 4.0 μg to 400.0 μg of said recombinant PCV2 ORF2 protein; and b. wherein said instruction manual includes information for the intramuscular administration of said single dose of the immunogenic composition into pigs to lessen the severity of one or more clinical symptoms caused by a PCV2 infection, in comparison to pigs not receiving said immunogenic composition, wherein said one or more clinical symptoms are selected from the group consisting of wasting, paleness of the skin, unthriftiness, respiratory distress, diarrhea, icterus, jaundice, lung lesions, nasal shedding, cough, diarrhea, and combinations thereof, and wherein administration of said immunogenic composition provides protective immunity after a single dose thereof.

20. The kit of claim 19, wherein said single dose immunogenic composition of PCV2 ORF2 protein comprises:

i) a polypeptide comprising a sequence selected from the group consisting of SEQ ID NO: 5, SEQ ID NO: 6, SEQ ID NO: 9, SEQ ID NO: 10, and SEQ ID NO: 11;

ii) any polypeptide that is at least 90% homologous to the polypeptide of i);

iii) a polypeptide that is encoded by a polynucleotide comprising the sequence of SEQ ID NO: 3 or SEQ ID NO: 4; or iv) any polypeptide that is encoded by a polynucleotide that is at least 90% homologous to the polynucleotide of iii).

21. The kit of claim 19, wherein said single dose immunogenic composition further comprises an inactivated viral vector.

22. The kit of claim 21, wherein said inactivated viral vector is a recombinant baculovirus coding for the recombinant PCV2 ORF2 protein.

23. The kit of claim 19, wherein said single dose immunogenic composition further comprises an additional component selected from the group consisting of cell culture supernate, BEI, sodium thiosulfate, carriers, adjuvants, media, viral inactivators, diluents, isotonic agents, immunomodulatory agents, antibiotics, and combinations thereof.

24. The kit of claim 19, wherein said polymer of acrylic or methacrylic acid is cross-linked with polyalkenyl ethers of sugars or polyalcohols.

25. The kit of claim 19, wherein said polymer of acrylic or methacrylic acid is a carbomer.

26. The kit of claim 25, wherein said carbomer is included in an amount from about 500 μg to about 5 mg carbomer per dose.

27. The kit of claim 19, wherein said single dose immunogenic composition further comprises a pharmaceutical acceptable salt.

28. The kit of claim 19, wherein each dose of said single dose immunogenic composition has 4 μg to 100 μg of recombinant PCV2 ORF2 protein therein.

29. The kit of claim 19, wherein each dose of said single dose immunogenic composition has 4 μg to 50 μg of recombinant PCV2 ORF2 protein therein.

30. The kit of claim 19, wherein each dose of said single dose immunogenic composition has 4 μg to 16 μg of recombinant PCV2 ORF2 protein therein.

31. The kit of claim 19, wherein said single dose immunogenic composition is a vaccine.

32. The kit of claim 19, wherein one dose of said single dose immunogenic composition has a volume of at least 1 ml.

33. The kit of claim 19, wherein one dose of said single dose immunogenic composition has a volume of at least 2 ml.

34. The kit of claim 28, wherein said single dose immunogenic composition is effective for lessening the severity of one or more clinical symptoms caused by a PCV2 infection by a single administration of said recombinant PCV2 ORF2 protein in comparison to pigs not receiving said immunogenic composition.

35. The kit of claim 29, wherein said single dose immunogenic composition is effective for lessening the severity of one or more clinical symptoms caused by a PCV2 infection by a single administration of said recombinant PCV2 ORF2 protein in comparison to pigs not receiving said immunogenic composition.

36. The kit of claim 28, wherein said instruction manual includes the information that the intramuscular application of one dose of said single dose immunogenic composition into pigs is effective for lessening the severity of one or more clinical symptoms caused by a PCV2 infection in comparison to pigs not receiving one dose of said single dose immunogenic composition.

37. The kit of claim 29, wherein said instruction manual includes the information that the intramuscular application of one dose of said single dose immunogenic composition into pigs is effective for lessening the severity of one or more clinical symptoms caused by a PCV2 infection in comparison to pigs not receiving one dose of said single dose immunogenic composition.

38. The kit of claim 30, wherein the instruction manual includes the information that the intramuscular application of one dose of said single dose immunogenic composition into pigs is effective for lessening the severity of one or more clinical symptoms caused by a PCV2 infection in comparison to pigs not receiving one dose of said single dose immunogenic composition.

* * * * *

SEQUENCE LISTING

```
<160> NUMBER OF SEQ ID NOS: 11

<210> SEQ ID NO 1
<211> LENGTH: 8
<212> TYPE: DNA
<213> ORGANISM: Artificial Sequence
<220> FEATURE:
<223> OTHER INFORMATION: This is a modified Kozak's sequence

<400> SEQUENCE: 1
```

-continued

```
ccgccatg                                                                 8

<210> SEQ ID NO 2
<211> LENGTH: 6
<212> TYPE: DNA
<213> ORGANISM: Artificial Sequence
<220> FEATURE:
<223> OTHER INFORMATION: This is a recombinant Eco R1 sequence

<400> SEQUENCE: 2 gaattc                                                                   6

<210> SEQ ID NO 3
<211> LENGTH: 713
<212> TYPE: DNA
<213> ORGANISM: Porcine circovirus

<400> SEQUENCE: 3
cagctatgac gtatccaagg aggcgttacc gcagaagaag acaccgcccc cgcagccatc      60
ttggccagat cctccgccgc cgcccctggc tcgtccaccc ccgccaccgc taccgttgga     120
gaaggaaaaa tggcatcttc aacacccgcc tctcccgcac cttcggatat actgtggaga     180
aggaaaaatg gcatcttcaa cacccgcctc tcccgcacct tcggatatac tgtgacgact     240
ttgttccccc gggagggggg accaacaaaa tctctatacc ctttgaatac tacagaataa     300
gaaaggttaa ggttgaattc tggccctgct cccccatcac ccagggtgat aggggagtgg     360
gctccactgc tgttattcta gatgataact ttgtaacaaa ggccacagcc ctaacctatg     420
acccatatgt aaactactcc tcccgccata caatccccca acccttctcc taccactccc     480
gttacttcac acccaaacct gttcttgact ccactattga ttacttccaa ccaaataaca     540
aaaggaatca gctttggctg aggctacaaa cctctagaaa tgtggaccac gtaggcctcg     600
gcactgcgtt cgaaaacagt aaatacgacc aggactacaa tatccgtgta accatgtatg     660
tacaattcag agaatttaat cttaaagacc ccccacttaa accctaaatg aat            713

<210> SEQ ID NO 4
<211> LENGTH: 713
<212> TYPE: DNA
<213> ORGANISM: Porcine circovirus

<400> SEQUENCE: 4
ccgccatgac gtatccaagg aggcgttacc gcagaagaag acaccgcccc cgcagccatc      60
ttggccagat cctccgccgc cgcccctggc tcgtccaccc ccgccaccgc taccgttgga     120
gaaggaaaaa tggcatcttc aacacccgcc tctcccgcac cttcggatat actgtcaagg     180
ctaccacagt cacaacgccc tcctgggcgg tggacatgat gagatttaat attgacgact     240
ttgttccccc gggagggggg accaacaaaa tctctatacc ctttgaatac tacagaataa     300
gaaaggttaa ggttgaattc tggccctgct cccccatcac ccagggtgat aggggagtgg     360
gctccactgc tgttattcta gatgataact ttgtaacaaa ggccacagcc ctaacctatg     420
acccatatgt aaactactcc tcccgccata caatccccca acccttctcc taccactccc     480
gttacttcac acccaaacct gttcttgact ccactattga ttacttccaa ccaaataaca     540
aaaggaatca gctttggctg aggctacaaa cctctagaaa tgtggaccac gtaggcctcg     600
gcactgcgtt cgaaaacagt aaatacgacc aggactacaa tatccgtgta accatgtatg     660
tacaattcag agaatttaat cttaaagacc ccccacttga accctaagaa ttc            713
```

<210> SEQ ID NO 5
<211> LENGTH: 233
<212> TYPE: PRT
<213> ORGANISM: Porcine circovirus

<400> SEQUENCE: 5

```
Met Thr Tyr Pro Arg Arg Tyr Arg Arg Arg His Arg Pro Arg
1               5                   10                  15

Ser His Leu Gly Gln Ile Leu Arg Arg Pro Trp Leu Val His Pro
        20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Thr Thr
50                      55                      60

Pro Ser Trp Ala Val Asp Met Met Arg Phe Asn Ile Asp Asp Phe Val
65                  70                      75                  80

Pro Pro Gly Gly Gly Thr Asn Lys Ile Ser Ile Pro Phe Glu Tyr Tyr
                    85                      90                  95

Arg Ile Arg Lys Val Lys Val Glu Phe Trp Pro Cys Ser Pro Ile Thr
                100                     105                     110

Gln Gly Asp Arg Gly Val Gly Ser Thr Ala Val Ile Leu Asp Asp Asn
                115                     120                     125

Phe Val Thr Lys Ala Thr Ala Leu Thr Tyr Asp Pro Tyr Val Asn Tyr
    130                     135                     140

Ser Ser Arg His Thr Ile Pro Gln Pro Phe Ser Tyr His Ser Arg Tyr
145                     150                     155                 160

Phe Thr Pro Lys Pro Val Leu Asp Ser Thr Ile Asp Tyr Phe Gln Pro
                165                     170                     175

Asn Asn Lys Arg Asn Gln Leu Trp Leu Arg Leu Gln Thr Ser Arg Asn
                180                     185                     190

Val Asp His Val Gly Leu Gly Thr Ala Phe Glu Asn Ser Lys Tyr Asp
            195                     200                     205

Gln Asp Tyr Asn Ile Arg Val Thr Met Tyr Val Gln Phe Arg Glu Phe
    210                     215                     220

Asn Leu Lys Asp Pro Pro Leu Lys Pro
225                 230
```

<210> SEQ ID NO 6
<211> LENGTH: 233
<212> TYPE: PRT
<213> ORGANISM: Porcine circovirus

<400> SEQUENCE: 6

```
Met Thr Tyr Pro Arg Arg Arg Tyr Arg Arg Arg His Arg Pro Arg
1               5                   10                  15

Ser His Leu Gly Gln Ile Leu Arg Arg Pro Trp Leu Val His Pro
        20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Val Lys Ala Thr Thr Val Thr Thr
50                      55                      60

Pro Ser Trp Ala Val Asp Met Met Arg Phe Asn Ile Asp Asp Phe Val
65                  70                      75                  80

Pro Pro Gly Gly Gly Thr Asn Lys Ile Ser Ile Pro Phe Glu Tyr Tyr
                    85                      90                  95

Arg Ile Arg Lys Val Lys Val Glu Phe Trp Pro Cys Ser Pro Ile Thr
                100                     105                     110
```

```
Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
            180                 185                 190

Val Asp His Val Gly Leu Gly Thr Ala Phe Glu Asn Ser Lys Tyr Asp
        195                 200                 205

Gln Asp Tyr Asn Ile Arg Val Thr Met Tyr Val Gln Phe Arg Glu Phe
    210                 215                 220

Asn Leu Lys Asp Pro Pro Leu Glu Pro
225                 230

<210> SEQ ID NO 7
<211> LENGTH: 756
<212> TYPE: DNA
<213> ORGANISM: Artificial Sequence
<220> FEATURE:
<223> OTHER INFORMATION: This sequence is from porcine circovirus type
      2, open reading frame 2, together with a portion from the pGEM
      T-easy vector.

<400> SEQUENCE: 7
gcggccgcgg gaattcgatc cgccatgacg tatccaagga ggcgttaccg cagaagaaga     60
caccgccccc gcagccatct tggccagatc ctccgccgcc gcccctggct cgtccacccc    120
cgccaccgct accgttggag aaggaaaaat ggcatcttca acacccgcct ctcccgcacc    180
ttcggatata ctgtcaaggc taccacagtc acaacgccct cctgggcggt ggacatgatg    240
agatttaata ttgacgactt tgttcccccg ggagggggga ccaacaaaat ctctataccc    300
tttgaatact acagaataag aaaggttaag gttgaattct ggccctgctc cccatcacc    360 cagggtgata ggggagtggg ctccactgct gttattctag atgataactt tgtaacaaag    420
gccacagccc taacctatga cccatatgta aactactcct cccgccatac aatcccccaa    480
cccttctcct accactcccg ttacttcaca cccaaacctg ttcttgactc cactattgat    540
tacttccaac aaataacaa aggaatcag ctttggctga ggctacaaac ctctagaaat    600
gtggaccacg taggcctcgg cactgcgttc gaaaacagta aatacgacca ggactacaat    660
atccgtgtaa ccatgtatgt acaattcaga gaatttaatc ttaaagaccc cccacttgaa    720
ccctaagaat tctatcacta gtgaattcgc ggccgc                              756

<210> SEQ ID NO 8
<211> LENGTH: 10387
<212> TYPE: DNA
<213> ORGANISM: Artificial Sequence
<220> FEATURE:
<223> OTHER INFORMATION: This is the porcine circovirus type 2, ORF2
      construct, which includes baculovirus and pGEM T-easy coding
      sequences.

<400> SEQUENCE: 8
aagctttact cgtaaagcga gttgaaggat catatttagt tgcgtttatg agataagatt     60
gaaagcacgt gtaaaatgtt tcccgcgcgt tggcacaact atttacaatg cggccaagtt    120
ataaaagatt ctaatctgat atgttttaaa acacctttgc ggcccgagtt gtttgcgtac    180
```

```
gtgactagcg aagaagatgt gtggaccgca gaacagatag taaaacaaaa ccctagtatt      240
ggagcaataa tcgatttaac caacacgtct aaatattatg atggtgtgca ttttttgcgg      300
gcgggcctgt tatacaaaaa aattcaagta cctggccaga cttttgccgcc tgaaagcata     360 gttcaagaat ttattgacac ggtaaaagaa tttacagaaa agtgtcccgg catgttggtg     420
ggcgtgcact gcacacacgg tattaatcgc accggttaca tggtgtgcag atatttaatg      480
cacaccctgg gtattgcgcc gcaggaagcc atagatagat tcgaaaaagc cagaggtcac     540
aaaattgaaa gacaaaatta cgttcaagat ttattaattt aattaatatt atttgcattc     600
tttaacaaat actttatcct attttcaaat tgttgcgctt cttccagcga accaaaacta     660
tgcttcgctt gctccgttta gcttgtagcc gatcagtggc gttgttccaa tcgacggtag     720
gattaggccg gatattctcc accacaatgt tggcaacgtt gatgttacgt ttatgctttt     780
ggttttccac gtacgtcttt tggccggtaa tagcctaaaa cgtagtgccg tcgcgcgtca      840 cgcacaaacac cggatgtttg cgcttgtccg cggggtattg aaccgcgcga tccgacaaat     900
ccaccacttt ggcaactaaa tcggtgacct gcgcgtcttt tttctgcatt atttcgtctt     960
tcttttgcat ggtttcctgg aagccggtgt acatgcggtt tagatcagtc atgacgcgcg     1020
tgacctgcaa atctttggcc tcgatctgct tgtccttgat ggcaacgatg cgttcaataa     1080
actcttgttt tttaacaagt tcctcggttt tttgcgccac caccgcttgc agcgcgtttg     1140
tgtgctcggt gaatgtcgca atcagcttag tcaccaactg tttgctctcc tcctcccgtt     1200
gtttgatcgc gggatcgtac ttgccggtgc agagcacttg aggaattact tcttctaaaa     1260
gccattcttg taattctatg gcgtaaggca atttggactt cataatcagc tgaatcacgc     1320
cggatttagt aatgagcact gtatgcggct gcaaatacag cgggtcgccc cttttcacga     1380
cgctgttaga ggtagggccc ccattttgga tggtctgctc aaataacgat tgtatttat      1440 tgtctacatg aacacgtata gctttatcac aaactgtata ttttaaactg ttagcgacgt     1500
ccttggccac gaaccggacc tgttggtcgc gctctagcac gtaccgcagg ttgaacgtat     1560
cttctccaaa tttaaattct ccaattttaa cgcgagccat tttgatacac gtgtgtcgat     1620
tttgcaacaa ctattgtttt ttaacgcaaa ctaaacttat tgtggtaagc ataattaaa      1680 tatgggggaa catgcgccgc tacaacactc gtcgttatga acgcagacgg cgccggtctc     1740
ggcgcaagcg gctaaaacgt gttgcgcgtt caacgcggca aacatcgcaa aagccaatag     1800 tacagtttg atttgcatat taacggcgat ttttaaatt atcttattta ataaatagtt       1860
atgacgccta caactccccg cccgcgttga ctcgctgcac ctcgagcagt tcgttgacgc     1920
cttcctccgt gtggccgaac acgtcgagcg ggtggtcgat gaccagcggc gtgccgcacg     1980
cgacgcacaa gtatctgtac accgaatgat cgtcgggcga aggcacgtcg gcctccaagt    2040
ggcaatattg gcaaattcga aaatatatac agttgggttg tttgcgcata tctatcgtgg     2100
cgttgggcat gtacgtccga acgttgattt gcatgcaagc cgaaattaaa tcattgcgat     2160
tagtgcgatt aaaacgttgt acatcctcgc tttaatcat gccgtcgatt aaatcgcgca     2220
atcgagtcaa gtgatcaaag tgtggaataa tgttttcttt gtattcccga gtcaagcgca     2280
gcgcgtattt taacaaacta gccatcttgt aagttagttt catttaatgc aactttatcc     2340
aataatatat tatgtatcgc acgtcaagaa ttaacaatgc gcccgttgtc gcatctcaac     2400
acgactatga tagagatcaa ataaagcgcg aattaaatag cttgcgacgc aacgtgcacg     2460
atctgtgcac cgcttccggc acgagctttg attgtaataa gttttacga agcgatgaca      2520 tgaccccccgt agtgacaacg atcacgccca aagaactgc cgactacaaa attaccgagt    2580
```

```
atgtcggtga cgttaaaact attaagccat ccaatcgacc gttagtcgaa tcaggaccgc    2640
tggtgcgaga agccgcgaag tatggcgaat gcatcgtata acgtgtggag tccgctcatt    2700
agagcgtcat gtttagacaa gaaagctaca tatttaattg atcccgatga ttttattgat    2760
aaattgaccc taactccata cacggtattc tacaatggcg gggttttggt caaaatttcc    2820
ggactgcgat tgtacatgct gttaacggct ccgcccacta ttaatgaaat taaaaattcc    2880
aattttaaaa aacgcagcaa gagaaacatt tgtatgaaag aatgcgtaga aggaaagaaa    2940
aatgtcgtcg acatgctgaa caacaagatt aatatgcctc cgtgtataaa aaaaatattg    3000
aacgatttga agaaaacaa tgtaccgcgc ggcggtatgt acaggaagag gtttatacta    3060
aactgttaca ttgcaaacgt ggtttcgtgt gccaagtgtg aaaaccgatg tttaatcaag    3120
gctctgacgc atttctacaa ccacgactcc aagtgtgtgg gtgaagtcat gcatctttta    3180
atcaaatccc aagatgtgta taaaccacca aactgccaaa aatgaaaaac tgtcgacaag    3240
ctctgtccgt ttgctggcaa ctgcaagggt ctcaatccta tttgtaatta ttgaataata    3300
aaacaattat aaatgctaaa tttgttttt attaacgata caaaccaaac gcaacaagaa    3360
catttgtagt attatctata attgaaaacg cgtagttata atcgctgagg taatatttaa    3420
aatcattttc aaatgattca cagttaattt gcgacaatat aattttattt tcacataaac    3480
tagacgcctt gtcgtcttct tcttcgtatt ccttctcttt tcattttc tcctcataaa    3540 aattaacata gttattatcg tatccatata tgtatctatc gtatagagta aattttttgt    3600
tgtcataaat atatatgtct ttttaatgg ggtgtatagt accgctgcgc atagtttttc    3660
tgtaatttac aacagtgcta ttttctggta gttcttcgga gtgtgttgct ttaattatta    3720
aatttatata atcaatgaat ttgggatcgt cggttttgta caatatgttg ccggcatagt    3780
acgcagcttc ttctagttca attacaccat ttttagcag caccggatta acataacttt    3840
ccaaaatgtt gtacgaaccg ttaaacaaaa acagttcacc tcccttttct atactattgt    3900
ctgcgagcag ttgtttgttg ttaaaaataa cagccattgt aatgagacgc acaaactaat    3960
atcacaaact ggaaatgtct atcaatatat agttgctgat atcatggaga taattaaaat    4020
gataaccatc tcgcaaataa ataagtattt tactgttttc gtaacagttt tgtaataaaa    4080
aaacctataa atattccgga ttattcatac cgtcccacca tcgggcgcgg atcagatctg    4140
cagcggccgc gggaattcga tccgccatga cgtatccaag gaggcgttac cgcagaagaa    4200
gacaccgccc ccgcagccat cttggccaga tcctccgccg ccgcccctgg ctcgtccacc    4260
cccgccaccg ctaccgttgg agaaggaaaa atggcatctt caacacccgc ctctcccgca    4320
ccttcggata tactgtcaag gctaccacag tcacaacgcc ctcctgggcg gtggacatga    4380
tgagatttaa tattgacgac tttgttcccc cgggaggggg gaccaacaaa atctctatac    4440
cctttgaata ctacagaata agaaggtta aggttgaatt ctggccctgc tccccatca    4500 cccagggtga taggggagtg ggctccactg ctgttattct agatgataac tttgtaacaa    4560
aggccacagc cctaacctat gacccatatg taaactactc ctcccgccat acaatccccc    4620 aaccttctc ctaccactcc cgttacttca cacccaaacc tgttcttgac tccactattg    4680
attacttcca accaaataac aaaaggaatc agctttggct gaggctacaa acctctagaa    4740
atgtggacca cgtaggcctc ggcactgcgt tcgaaaacag taaatacgac caggactaca    4800
atatccgtgt aaccatgtat gtacaattca gagaatttaa tcttaaagac cccccacttg    4860
aaccctaaga attctatcac tagtgaattc gcggccgccg gccgctccag aattctagaa    4920
ggtacccggg atcctttcct gggacccggc aagaaccaaa aactcactct cttcaaggaa    4980
```

```
atccgtaatg ttaaacccga cacgatgaag cttgtcgttg gatggaaagg aaaagagttc    5040
tacagggaaa cttggacccg cttcatggaa gacagcttcc ccattgttaa cgaccaagaa    5100
gtgatggatg ttttccttgt tgtcaacatg cgtcccacta gacccaaccg ttgttacaaa    5160
ttcctggccc aacacgctct gcgttgcgac cccgactatg tacctcatga cgtgattagg    5220
atcgtcgagc cttcatgggt gggcagcaac aacgagtacc gcatcagcct ggctaagaag    5280
ggcggcggct gcccaataat gaaccttcac tctgagtaca ccaactcgtt cgaacagttc    5340
atcgatcgtg tcatctggga gaacttctac aagcccatcg tttacatcgg taccgactct    5400
gctgaagagg aggaaattct ccttgaagtt tccctggtgt tcaaagtaaa ggagtttgca    5460
ccagacgcac ctctgttcac tggtccggcg tattaaaaca cgatacattg ttattagtac    5520
atttattaag cgctagattc tgtgcgttgt tgatttacag acaattgttg tacgtatttt    5580
aataattcat taaatttata atctttaggg tggtatgtta gagcgaaaat caaatgattt    5640
tcagcgtctt tatatctgaa tttaaatatt aaatcctcaa tagatttgta aaataggttt    5700
cgattagttt caaacaaggg ttgttttttcc gaaccgatgg ctggactatc taatggattt    5760
tcgctcaacg ccacaaaact tgccaaatct tgtagcagca atctagcttt gtcgatattc    5820
gtttgtgttt tgttttgtaa taaaggttcg acgtcgttca aaatattatg cgcttttgta    5880
tttctttcat cactgtcgtt agtgtacaat tgactcgacg taaacacgtt aaataaagct    5940
tggacatatt taacatcggg cgtgttagct ttattaggcc gattatcgtc gtcgtcccaa    6000
ccctcgtcgt tagaagttgc ttccgaagac gattttgcca tagccacacg acgcctatta    6060
attgtgtcgg ctaacacgtc cgcgatcaaa tttgtagttg agcttttggg aattatttct    6120
gattgcgggc gttttgggc gggtttcaat ctaactgtgc ccgatttttaa ttcagacaac    6180 acgttagaaa gcgatggtgc aggcggtggt aacatttcag acggcaaatc tactaatggc    6240
ggcggtggtg gagctgatga taaatctacc atcggtggag gcgcaggcgg ggctggcggc    6300
ggaggcggag gcggaggtgg tggcggtgat gcagacggcg gtttaggctc aaatgtctct    6360
ttaggcaaca cagtcggcac ctcaactatt gtactggttt cgggcgccgt ttttggtttg    6420
accggtctga gacgagtgcg attttttttcg tttctaatag cttccaacaa ttgttgtctg    6480
tcgtctaaag gtgcagcggg ttgaggttcc gtcggcattg gtggagcggg cggcaattca    6540
gacatcgatg gtggtggtgg tggtggaggc gctggaatgt taggcacggg agaaggtggt    6600
ggcggcggtg ccgccggtat aatttgttct ggtttagttt gttcgcgcac gattgtgggc    6660
accggcgcag gcgccgctgg ctgcacaacg gaaggtcgtc tgcttcgagg cagcgcttgg    6720
ggtggtggca attcaatatt ataattggaa tacaaatcgt aaaaatctgc tataagcatt    6780
gtaatttcgc tatcgtttac cgtgccgata tttaacaacc gctcaatgta agcaattgta    6840
ttgtaaagag attgtctcaa gctcgccgca cgccgataac aagccttttc atttttacta    6900
cagcattgta gtggcgagac acttcgctgt cgtcgacgta catgtatgct ttgttgtcaa    6960
aaacgtcgtt ggcaagcttt aaaatattta aagaacatc tctgttcagc accactgtgt    7020
tgtcgtaaat gttgtttttg ataatttgcg cttccgcagt atcgacacgt tcaaaaaatt    7080
gatgcgcatc aattttgttg ttcctattat tgaataaata agattgtaca gattcatatc    7140
tacgattcgt catggccacc acaaatgcta cgctgcaaac gctggtacaa ttttacgaaa    7200
actgcaaaaa cgtcaaaact cggtataaaa taatcaacgg gcgctttggc aaaatatcta    7260
ttttatcgca caagcccact agcaaattgt atttgcagaa aacaatttcg gcgcacaatt    7320
ttaacgctga cgaaataaaa gttcaccagt taatgagcga ccacccaaat tttataaaaa    7380
```

-continued

```
tctattttaa tcacggttcc atcaacaacc aagtgatcgt gatggactac attgactgtc    7440
ccgatttatt tgaaacacta caaattaaag gcgagctttc gtaccaactt gttagcaata    7500
ttattagaca gctgtgtgaa gcgctcaacg atttgcacaa gcacaatttc atacacaacg    7560
acataaaact cgaaaatgtc ttatatttcg aagcacttga tcgcgtgtat gtttgcgatt    7620
acggattgtg caaacacgaa aactcactta gcgtgcacga cggcacgttg gagtatttta    7680
gtccggaaaa aattcgacac acaactatgc acgtttcgtt tgactggtac gcggcgtgtt    7740
aacatacaag ttgctaacgt aatcatggtc atagctgttt cctgtgtgaa attgttatcc    7800
gctcacaatt ccacacaaca tacgagccgg aagcataaag tgtaaagcct ggggtgccta    7860
atgagtgagc taactcacat taattgcgtt gcgctcactg cccgctttcc agtcgggaaa    7920
cctgtcgtgc cagctgcatt aatgaatcgg ccaacgcgcg gggagaggcg gtttgcgtat    7980
tgggcgctct tccgcttcct cgctcactga ctcgctgcgc tcggtcgttc ggctgcggcg    8040
agcggtatca gctcactcaa aggcggtaat acgttatcc acagaatcag gggataacgc    8100
aggaaagaac atgtgagcaa aaggccagca aaaggccagg aaccgtaaaa aggccgcgtt    8160
gctggcgttt ttccataggc tccgcccccc tgacgagcat cacaaaaatc gacgctcaag    8220
tcagaggtgg cgaaacccga caggactata aagataccag gcgtttcccc ctggaagctc    8280
cctcgtgcgc tctcctgttc cgaccctgcc gcttaccgga tacctgtccg cctttctccc    8340
ttcgggaagc gtggcgcttt ctcatagctc acgctgtagg tatctcagtt cggtgtaggt    8400
cgttcgctcc aagctgggct gtgtgcacga accccccgtt cagcccgacc gctgcgcctt    8460
atccggtaac tatcgtcttg agtccaaccc ggtaagacac gacttatcgc cactggcagc    8520
agccactggt aacaggatta gcagagcgag gtatgtaggc ggtgctacag agttcttgaa    8580
gtggtggcct aactacggct acactagaag gacagtattt ggtatctgcg ctctgctgaa    8640
gccagttacc ttcggaaaaa gagttggtag ctcttgatcc ggcaaacaaa ccaccgctgg    8700
tagcggtggt ttttttgttt gcaagcagca gattacgcgc agaaaaaaag gatctcaaga    8760
agatcctttg atcttttcta cggggtctga cgctcagtgg aacgaaaact cacgttaagg    8820
gattttggtc atgagattat caaaaaggat cttcacctag atcctttaa attaaaaatg    8880
aagttttaaa tcaatctaaa gtatatatga gtaaacttgg tctgacagtt accaatgctt    8940
aatcagtgag gcacctatct cagcgatctg tctatttcgt tcatccatag ttgcctgact    9000
ccccgtcgtg tagataacta cgatacggga gggcttacca tctggcccca gtgctgcaat    9060
gataccgcga gacccacgct caccggctcc agatttatca gcaataaacc agccagccgg    9120
aagggccgag cgcagaagtg gtcctgcaac tttatccgcc tccatccagt ctattaattg    9180
ttgccgggaa gctagagtaa gtagttcgcc agttaatagt ttgcgcaacg ttgttgccat    9240
tgctacaggc atcgtggtgt cacgctcgtc gtttggtatg gcttcattca gctccggttc    9300
ccaacgatca aggcgagtta catgatcccc catgttgtgc aaaaaagcgg ttagctcctt    9360
cggtcctccg atcgttgtca gaagtaagtt ggccgcagtg ttatcactca tggttatggc    9420
agcactgcat aattctctta ctgtcatgcc atccgtaaga tgcttttctg tgactggtga    9480
gtactcaacc aagtcattct gagaatagtg tatgcggcga ccgagttgct cttgcccggc    9540
gtcaatacgg gataataccg cgccacatag cagaactttt aaagtgctca tcattggaaa    9600
acgttcttcg gggcgaaaac tctcaaggat cttaccgctg ttgagatcca gttcgatgta    9660
acccactcgt gcacccaact gatcttcagc atcttttact ttcaccagcg tttctgggtg    9720
agcaaaaaca ggaaggcaaa atgccgcaaa aaagggaata agggcgacac ggaaatgttg    9780
```

-continued aatactcata ctcttccttt ttcaatatta ttgaagcatt tatcagggtt attgtctcat 9840
gagcggatac atatttgaat gtatttagaa aaataaacaa ataggggttc cgcgcacatt 9900
tccccgaaaa gtgccacctg acgtctaaga aaccattatt atcatgacat taacctataa 9960
aaataggcgt atcacgaggc cctttcgtct cgcgcgtttc ggtgatgacg gtgaaaacct 10020
ctgacacatg cagctcccgg agacggtcac agcttgtctg taagcggatg ccgggagcag 10080
acaagcccgt cagggcgcgt cagcgggtgt tggcgggtgt cggggctggc ttaactatgc 10140
ggcatcagag cagattgtac tgagagtgca ccatatgcgg tgtgaaatac cgcacagatg 10200
cgtaaggaga aaataccgca tcaggcgcca ttcgccattc aggctgcgca actgttggga 10260
agggcgatcg gtgcgggcct cttcgctatt acgccagctg gcgaaagggg gatgtgctgc 10320
aaggcgatta agttgggtaa cgccagggtt ttcccagtca cgacgttgta aaacgacggc 10380
cagtgcc 10387

<210> SEQ ID NO 9
<211> LENGTH: 20
<212> TYPE: PRT
<213> ORGANISM: Porcine circovirus

<400> SEQUENCE: 9

Ser Tyr Pro Arg Arg Arg Tyr Arg Arg Arg Arg His His Pro Pro Ser
1 5 10 15

His Leu Gly Gln
20

<210> SEQ ID NO 10
<211> LENGTH: 19
<212> TYPE: PRT
<213> ORGANISM: Porcine circovirus

<400> SEQUENCE: 10

Pro Arg His His Tyr Arg Pro Arg Arg Lys Asn Gly Ile Phe Asn Thr
1 5 10 15

Thr Leu Ser

<210> SEQ ID NO 11
<211> LENGTH: 233
<212> TYPE: PRT
<213> ORGANISM: Artificial Sequence
<220> FEATURE:
<223> OTHER INFORMATION: This is an amino acid sequence for porcine circovirus type 2, open reading frame 2.

<400> SEQUENCE: 11

Met Thr Tyr Pro Arg Arg Arg Tyr Arg Arg Arg Arg His Arg Pro Arg
1 5 10 15

Ser His Leu Gly Gln Ile Leu Arg Arg Arg Pro Trp Leu Val His Pro
20 25 30

Arg His Arg Tyr Arg Trp Arg Arg Lys Asn Gly Ile Phe Asn Thr Arg
35 40 45

Leu Ser Arg Thr Phe Gly Tyr Thr Val Lys Ala Thr Thr Val Arg Thr
50 55 60

Pro Ser Trp Ala Val Asp Met Met Arg Phe Asn Ile Asp Asp Phe Val
65 70 75 80

Pro Pro Gly Gly Gly Thr Asn Lys Ile Ser Ile Pro Phe Glu Tyr Tyr
85 90 95

Arg Ile Lys Lys Val Lys Val Glu Phe Trp Pro Cys Ser Pro Ile Thr

-continued

```
            100                 105                 110
Gln Gly Asp Arg Gly Val Gly Ser Thr Ala Val Ile Leu Asp Asp Asn
            115                 120                 125

Phe Val Thr Lys Ala Thr Ala Leu Thr Tyr Asp Pro Tyr Val Asn Tyr
            130                 135                 140

Ser Ser Arg His Thr Ile Pro Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ser Arg Asn
                180                 185                 190

Val Asp His Val Gly Leu Gly Thr Ala Phe Glu Asn Ser Ile Tyr Asp
            195                 200                 205

Gln Asp Tyr Asn Ile Arg Val Thr Met Tyr Val Gln Phe Arg Glu Phe
            210                 215                 220

Asn Leu Lys Asp Pro Pro Leu Lys Pro
225                 230
```